(12) United States Patent
Virgin et al.

(10) Patent No.: US 7,794,928 B2
(45) Date of Patent: Sep. 14, 2010

(54) NOROVIRUS DETECTION, METHODS AND COMPOSITIONS THEREFOR

(75) Inventors: Herbert W. Virgin, St. Louis, MO (US); Christiane Wobus, Dexter, MI (US); Stephanie Karst, Shreveport, LA (US)

(73) Assignee: Washington University, Saint Louis, MO (US)

( * ) Notice: Subject to any disclaimer, the term of this patent is extended or adjusted under 35 U.S.C. 154(b) by 148 days.

(21) Appl. No.: 12/025,327

(22) Filed: Feb. 4, 2008

(65) Prior Publication Data

US 2008/0254443 A1 Oct. 16, 2008

Related U.S. Application Data

(63) Continuation of application No. 11/122,944, filed on May 5, 2005, now abandoned.

(60) Provisional application No. 60/568,301, filed on May 5, 2004.

(51) Int. Cl.
*C12Q 1/70* (2006.01)
*C12P 21/04* (2006.01)
*C12N 5/00* (2006.01)
*C12N 7/00* (2006.01)
*G01N 33/567* (2006.01)

(52) U.S. Cl. .................. 435/5; 435/7.21; 435/70.3; 435/235.1; 435/239; 435/325

(58) Field of Classification Search .............. 435/6, 435/91.1, 29, 70.1, 235.1, 5, 7.21, 70.3, 239, 435/325; 436/503; 536/23.1, 24.32
See application file for complete search history.

(56) References Cited

U.S. PATENT DOCUMENTS

| | | | |
|---|---|---|---|
| 5,198,428 A | 3/1993 | Sivaramakrishnan et al. | |
| 6,117,674 A * | 9/2000 | Goodwin et al. | ............. 435/325 |
| 7,041,444 B2 | 5/2006 | Virgin | |
| 7,264,923 B2 * | 9/2007 | Virgin et al. | .................... 435/5 |
| 2006/0172287 A1 | 8/2006 | Virgin | |

OTHER PUBLICATIONS

Atmar et al., "Diagnosis of Noncultivatable Gastroenteritis Viruses, the Human Caliciviruses," Clinical Microbiology Reviews, 2001, pp. 15-37, vol. 14.
Darnell et al., "Jak-STAT Pathways and Transcriptional Activation in Response to IFNs and Other Extracellular Signaling Proteins," Science, 1994, pp. 1415-1421, vol. 264.
Dieu et al., "Selective Recruitment of Immature and Mature Dendritic Cells by Distinct Chemokines Expressed in Different Anatomic Sites," J. Exp. Med., 1988, pp. 373-386, vol. 188.
Duizer et al., "Laboratory Efforts to Cultivate Noroviruses," J. Gen. Virol., 2004, pp. 79-87, vol. 85.
Karst et al., "STAT1-Dependent Innate Immunity to a Norwalk-Like Virus," Science, 2003, pp. 1575-1578, vol. 299.
Langloss et al., "In Vitro Interaction of Alveolar Macrophages and Pneumocytes with Feline Respiratory Viruses," Infection Immun., 1978, pp. 836-841, vol. 20.
National Center for Research Resources, "Research Highlights—Escaping the Norwalk Virus," http://www.ncrr.nih.gov/newspub/oct03rpt/stories2.asp, 2004, 3 pages.
Reckess, "New Mouse Virus may Help Scientists Better Understand Cruise Ship Epidemics," http://mednews.wustl.edu/medadmin/PAnews.nsf/PrintView/AE60E8F4D53C2B8C86256CE0005DBB1, 2004, 2 pages.
Seal et al., "Isolation of Caliciviruses from Skunks That are Antigenically and Genotypically Related to San Miguel Sea Lion Virus," Virus Res., 1995, pp. 1-12, vol. 37.
Stuart et al., "Differential Induction of Bone Marrow Macrophage Proliferation by Mycoplasmas Involves Granulocyte-Macrophage Colony-Stimulating Factor," Infection Immun., 1990, pp. 3558-3563, vol. 58.
Virgin et al, "Monoclonal Antibodies to Reovirus Reveal Structure/Function Relationships between Capsid Proteins and Genetics of Susceptibility to Antibody Action," J Virol, 1991, pp. 6772-6781, vol. 65(12).
Wobus et al., "Replication of Norovirus in Cell Culture Reveals a Tropism for Dendritic Cells and Macrophages," PLOS Biology, 2004, pp. 2076-2084, vol. 2.

* cited by examiner

*Primary Examiner*—Jane Zara
(74) *Attorney, Agent, or Firm*—Zackson Law LLC; Saul L. Zackson

(57) ABSTRACT

A norovirus-permissive cell culture infected with a norovirus, and methods of culturing a norovirus, are disclosed. Norovirus-permissive cells include dendritic cell-lineage cells, and macrophage-lineage cells, such as dendritic cells, and macrophages having a deficiency in a cellular anti-viral pathway such as a STAT-1-dependent pathway, an interferon receptor-dependent pathway, or a PKR-dependent pathway. Also disclosed are methods of screening anti-viral compounds against norovirus-permissive cells infected with norovirus, and norovirus adapted to grow in fibroblasts as well as macrophages that are not deficient in a cellular anti-viral pathway. Methods of making a norovirus vaccine are also disclosed. A replicative form of norovirus as well as its use in the development of an anti-viral agent and a polypeptide expression system are also described. Further disclosed are methods of detecting norovirus in a sample.

12 Claims, 28 Drawing Sheets

FIG. 7A

<110> Washington University in St. Louis

Virgin, Herbert W.

<120> Norovirus Culture, Methods and Uses Therefor

<130> 7383H-000008/US

<160> 1

<170> PatentIn version 3.2

<210> 1

<211> 7382

<212> RNA

<213> Mouse norovirus

<400> 1
gugaauucua gaaggcaacg ccaucuucug cgcccucugu gcgcaacaca gagaaacgca 60
aaaacaagaa ggcuucgycu aaagcuagug ucuccuuuugg agcaccuagc cccucucuu 120 cggagagcga agacgaaruu aauuacauga ccccuccuga gcaggaagcu cagcccggcg 180
cccuugcggc ccuucaugcg gaagggccgc uugccgggcu cccgugacg cguagugaug 240 cacgcgugcu gaucuucaau gagugggagg agaggaagaa gucugauccg uggcuacggc 300
uggacauguc ugauaaggcu aucuuccgcc guuaccccca ucugcggccu aaggaggaua 360
ggccugacgc gcccucccau gcggaggacg cuauggaugc caaggagccu gugaucggcu 420
cuaucuugga gcaggaugau cacaaguuuu accauuacuc ugucuacauc gguggcggcc 480
uugugauggg ggucaacaac cccagugcug cggucugcca ggcaacgauu gauguggaga 540
agcuacaccu cuggugggcgg ccugucuggg agcccgccca wccccuugac ucggcugagu 600
ugaggaagug cgugggcaug acugucccccu acguggccac caccgucaac uguuaucagg 660

FIG. 7B ucugcugcug gauuguuggc aucaaggaca ccuggcugaa gagggcgaag aucucuagag 720
aucugcccuu cuacagcccc guccaggacu ggaacgucga cccccaggag cccuucauuc 780
cauccaagcu caggaugguc ucggauggca uccuggugge cuugucggca gugauuggcc 840
ggccaauuaa gaaccuacug gccucaguua agccgcucaa cauucucaac aucgugcuga 900
gcugugauug gaccuuuucg ggcauuguca augcccugau cuugcuugcu gagcucuuug 960
acaucuuuug gacccccccu gauguracca rcuggaugau cucuaucuuc ggggaauggc 1020
aggccgaagg gcccuucgac cyugcucuug acguggugcc cacccuguug ggcgggaucg 1080
ggauggcuuu uggccucrcc ucugagacca ucuggcgcaa gcucdcuucc accaacucgg 1140
cucucaaggc cgcccaagag augggcaagu ucgccauaga ggucuucaag caaauuaugg 1200
ccuggaucug gcccucugag gacccagugc cagcccucuu auccaacaug gagcaggcca 1260
ucauuaagaa ugagugucaa cudgagaacc aacucacggc cauguugcgg gaucgcaacg 1320
caggggcuga auuccuvagg ucccuugaug aggaggagca ggaaguccgc aagaucgcag 1380
cuaagugcgg caacucggcc accacuggaa ccaccaacgc ucugcuggcc aggaucagca 1440
uggcccgcgc ggccuuugag aaagcucgcg cugaacagac cucccgaguc cgcccuguggg 1500 ugducauggu cucaggcagg cccgggaucg ggaaaaccug cuuuugccaa aaccuagcca 1560
agaggauugc ugcgucccug ggugaugaga ccucuguugg caucauacca cgcgcugaug 1620
ucgaccacug ggaugcuuac aagggagcca gaguggnucu cuggaugau uucggcaugg 1680 acaacguggu gaaggaugca cugaggcuuc agaugcuugc cgacacgugc ccagugacac 1740
ucaauuguga caggauugag aacaagggaa agaugyuuga cucucagguc auuaucauca 1800
ccacaaauca acaaaccccc gygccccugg acuaugucaa ccuggaggcg gucugccgcc 1860
gcauagauuu ccuggnuuau grnugagagcc cuguuguuga ugaugcucgg gccagagccc 1920
cuggcgaugu gaaugcagug aaagcugcca ugaggcccga uuacagccac aucaauuuca 1980
ucuuggcacc gcagggcggc uuugaccguc gggaaacacc cccuacggua agggcgucac 2040

FIG. 7C caagaucauu ggcgccacug cucuuuugcgc gagagcgguu gcucuugucc augagcgcca 2100
ugaugauuuc ggccuccaga acaaggucya ugacuuuugau gcgcgcaarg ucaccgccuu 2160
caaagccaug gcggcugacg ccggcauucc augguacaaa auggcagcua uggggugcaa 2220
agcaaugggg gugcaccugu guagaggagg ccaugcauuu acuuaaggau uaugaggugg 2280 cuccccuguca ggugaucuac aaggugcca ccauaaaugu gagcugcauc aaggggugccc 2340 caauggutga aaaggucaag gagccugaau ugcccaaaac acuugucaac ugugucagaa 2400
ggauaaagga ggcccgccuc cgcugcuacu guaggauggc ugcugacguc aucacgucca 2460
uucugcaggc ggccggcacg gccuucucua uuuaccacca gauugagaag aggucuagac 2520
cauccuuuua uggggaucau ggauacaccu accgugacgg accuggaucc uuugacaucu 2580
uugaggauga cgaugauggg ugguaccacu cugagggaaa gaagggcaag aacaagaagg 2640
gccgggggcg acccggaguc uucagaaccc gugggcucac ggaugaggag uacgaugaau 2700
ucaagaagcg ccgcgagucu aggggcggca aguacuccau ugaugauuac cucgcugrcc 2760
gcgagcgaga agaagaacuc cuggagcggg acgaggagga ggcuaucuuc ggggayggcu 2820
ucggguugaa ggccacccgc cguuccegca aggcagagag agccaaacug ggccugguuu 2880 cuggugcga cauccgcgcc cgcaagccga ucgacuggaa uguggiuggc cccuccuggg 2940 cugacgauga ccgccaggiuc gcuacggcga gaagaucaac uuugaggccc caguyuccau 3000
cuggucccgu guugugcagu ucggcacggg gugggcuuu uggggugagc ggccacgucu 3060
ucaucaccgc caagcaugug gcgcccccca agggcacgga gaucuuuggg cgcaagcccg 3120
gggacuucac uguctcuucc agcggggacu ucuugaagua cuacuucacc agcgccguca 3180
ggccugacru ucccgccaug guccuggaga augggugcca ggagggcguc gucgccucgg 3240
uccuugucaa gagagccucc ggcgagaugc uugcccuggc ugucaggaug gguucacagg 3300
ccgccaucaa gauugguagu gccguugugc augggcaaac uggcauugcuc cugacuggcu 3360 cuaaugccaa ggcccaggac cucgggacca uccggggcga cuguggcugu cccauguuu 3420

FIG. 7D auaagaaggg uaacaccugg guugugauug gggugcacgu ggcggccacu aggucuggua 3480
acacagucau ugccgccacu cacggagaac ccacacuuga ggcucuggag uuccagggac 3540
cccccaugcu ucccgcccc ucaggcaccu augcaggccu cccaucgcc gauuacggcg 3600 acgcucccc cuugagcacc aagaccaugu ucuggcguac cucgccagag aagcuuccc 3660 cuggggcuug ggagccagcc uaucucggcu cuaaagauga gagggguggac gguccuuccc 3720 uucagcaggu caugcgagau cagcuuaagc ccuauucaga accacgcggu cugcuuccc 3780 cucaagaaau ccuugaugca gucugcgacg ccauugagaa ccgccuugag aacacccuug 3840
aaccacagaa gcccuggaca uuuaagaagg cuugugagag cuuggacaag aacaccagya 3900
gyggguaucc cuaucacaag cagaagagca aggacuggac ggggagcgcu uuuauuggcg 3960 rucuuggiiga ccaggccacc cacgccaaca acauguauga gaugggiiaaa uccaugcgac 4020 ccauuuauac agcugcccuc aaggaugaac ugguuaagcc agacaagauc uacgggaaga 4080
uaaagaagag gcuucucugg ggcucugacc uugrcaccau gauucgcgcu gcccgugcyu 4140
uuggcccuuu cugugaugcu cugaaagaau ccugcauuuu caaccccauc agagugggca 4200
ugucgaugaa cgaagauggc cccuucaucu ucgcaagaca cgccaauuuc agguaccaca 4260
uggaugcuga cuauaccagg ugggacucca cccaacagag agccauccua aagcgcgcug 4320
gygacaucau ggygcgccuc uccccugagc cagacuuggc ucggguuguc auggaugauc 4380
uccuggcccc cucgcugiiug gacgucggcg acuuaagau cguugucgag gaggggcucc 4440 caucggcug cccuugcacc acacagcuga auaguuuggc ucacuggauu uugacccuuu 4500 gugcaaugu ugagguaacc cgaguugacc cugacauugu gaugcaagaa ucgaguuyu 4560 ccuucuaugg ugaugacgag gugguuucga ccaaccucga guuggauaug guuaaguaca 4620
ccauggcuuu gaggcgguac ggucucccucc cgacucgcgc ggacaaggag gagggaccuc 4680
uggagcgucg ccagacgcug cagggcaucu ccuuccugcg ccgugcgaua guuggugacc 4740
aguuuggguc guacggucgu cuugaucgug ccagcaucga ccgccagcuc cucuggacua 4800

FIG. 7E aaggaccuaa ccaccagaac cccuuugaga cucucccugg acaugcucag agacccuccc 4860
aacuaauggc ccugcucggu gaggcugcca ugcaugguga aaaguauuac aggacugugg 4920
cuucccgugu cuccaaggag gccgcccaaa gugggauara aaugguaguc cccacgccac 4980
cgaucuguuu ugcgcugggu gcgcuuugga aaauggaugc ugagaccccg caggaacgcu 5040
cagcagucuu ugugaaugag gaugagugau ggcgcagcgc caaaagccaa uggcucugag 5100
gccagcggcc aggaucuugu uccugccgcc guugaacagg ccgucccay ucaacccgug 5160 gcuggcgcgg cucuugccgc ccccgccgcc gggcaaauua accaaauugr ccccuggauc 5220
uuccaaaauu uuguccagug ccccuuggu gaguuuucca uuucgccucg aaacacccca 5280
ggugaaauac uguuugauuu ggcccucggg ccagggcuua accccuaccu ugcccaccuc 5340
ucagccaugu acaccggcug gguuggggaac ruggaggiuc agcuggnccu cgccggcaau 5400
gccuuuacug cuggcaaggu gguguugcc cuuguaccac ccuauuucc caaggguca 5460 cucaccacug cccagaucac augcuuccca caugucaugu gugaugugcg cacccuggag 5520
cccauucaac ucccucuucu ugaugugcgu cgagucccuuu ggcaugcuac ccaggaucaa 5580
gaggaaucua ugcgccuggu uugcaugcug uacacgccac uccgcacaaa cagcccgggu 5640
gaugagucuu uuguggucuc uggccgcccuu cuuucuaage cggcggcuga uuucaauuuu 5700
gucuaccuaa cucccccccau agagagaacc aucaccgga uggucgacuu gcccgugaua 5760
cagccgcggc ugugcacgca cgcacguugg ccugccccgg ucuauggucu cuuggugggac 5820 ccauccucc cucaaauuc ccaguggcag aauggaaggg ugcacguuga ugggacccug 5880
cuuggnacca ccccaaucuc cgguucaugg guguccugcu uugcgkcgga ggcugccuau 5940
aaguuccaau cgggcaccgg ugagguggcg acauucaccc ugauugagca ggauggaucu 6000
gccuacgucc ccggugacag ggcagcacca cucggguuac cccgauuucu cugggcaacu 6060
ggagaucgag guccagaccg agaccaccaa gacuggagac aagcucaagg ucaccacuuu 6120
gagaugauuc uuggcccaac gaccaacgcg gaccaggccc ccuaccaggg caggguguuc 6180

FIG. 7F gccagcguca cugcugcggc cucucuugac uugguggaug gcaggguucg ugcgguccca 6240
agauccaucu acgguuuuca ggacaccauc ccugaauaca acgaugggcu acugguuccc 6300 cuugccccc caauuggucc cuuucucccc ggcgaggucc uccugagguu ccggaccuac 6360
augcgucaga ucgacaccgc ugacgccgca gcagaggcga uagacugugc acuccccag 6420 gaguuugucu ccugguucgc gucuaacgcg uucaccgugc agccgaggc ccugcucuu 6480 agauacagga acacccugac ugggcaacug cuguucgagu gcaagcucua aacgaaggu 6540 uacaucgccu ugucuuauuc cggcucagga ccccucaccu uccgaccga uggcaucuuu 6600 gaggucguca guuggguucc ucgccuuuac caauuggccu cugugggaag uuuggcaaca 6660
ggccgaaugc ucaaacaaua auggcuggug cucuuuuugg agcgauugga gguggccuga 6720
ugggcauaau uggcaauucc aucucaaaug uucaaaaccu ucaggcaaac aaacaauugg 6780
cagcucagca auuuggunau aauucuuccc ugcuugcaac gcaaauucaa gcccagaagg 6840
aucucacucu gauggggcag caauucaacc agcagcucca aaccaacucu uucaagcacg 6900
acuuggaaau gcuuggcgcu caggugcaag cccaggcgca ggcccaggag aacgccauca 6960
auaucaaaac ggcgcagcuc caggccgcag gcuuuucaaa gacagaugcc acacgccuug 7020
ccuuggggca gcagcccacg agggccgugg auuggucugg gacgcgguac uacaccgcua 7080
accagccagu cacgggcuuc ucggguggcu uuaccccaac cuacacucca gguaggcaag 7140
ugacaucccg cccuguggac acauccccuc uaccgaucuc gggguggacgc uugcccuccc 7200 uucguggagg uuccugguc ccgcgcgacc auacgccggc gacucaaggc accuacacga 7260
acggacgguu cguguccucuc ccuaagaucg ggaguagcag ggcauagguu ggaagagaaa 7320
ccuuuuguga aaaugauuuc ugcuuacugc uuucuuuucu uuguggaguaguaa uagaugcauu 7380 uc 7382

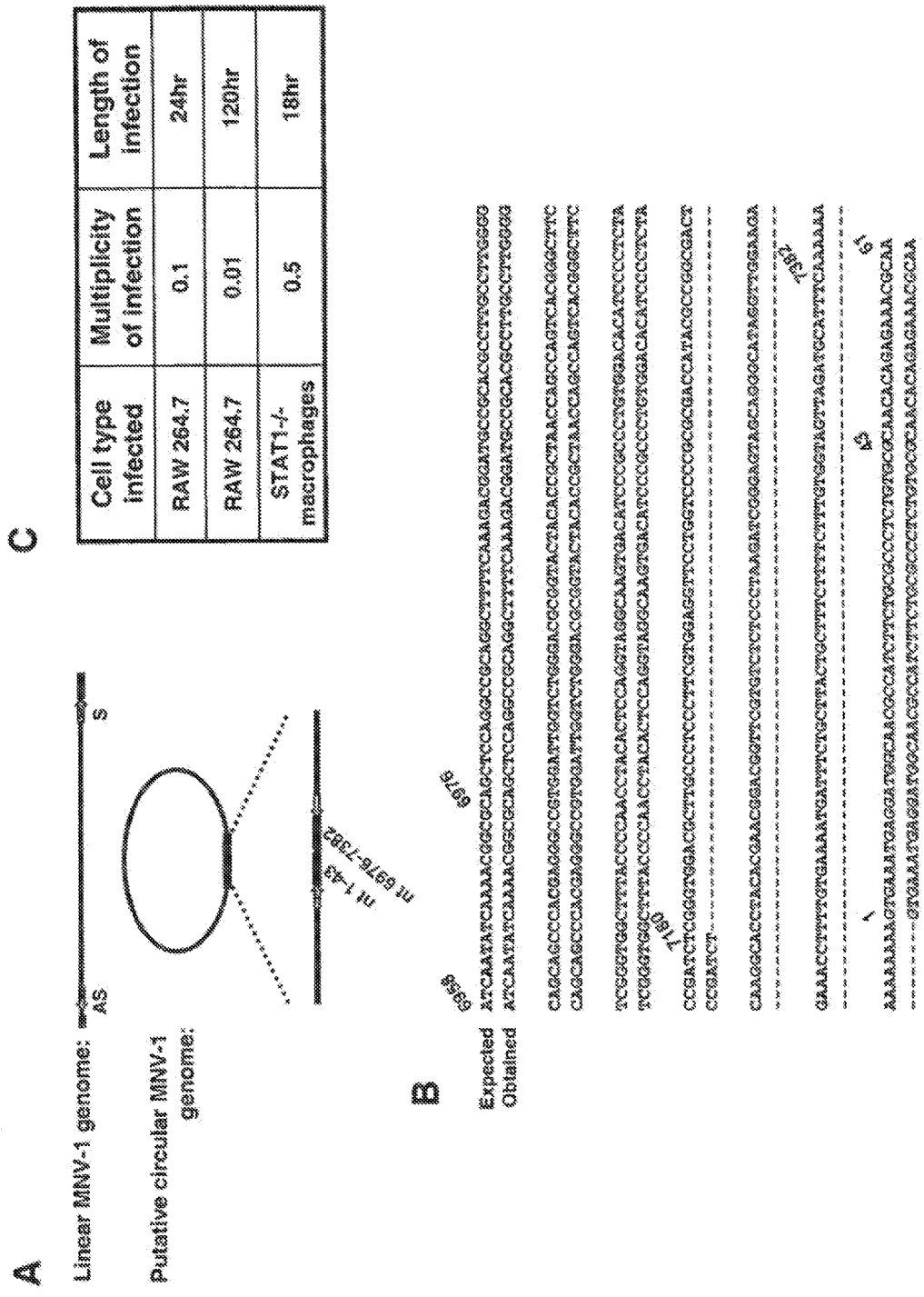

Sequence of PCR product without ligase

5' end of PCR product

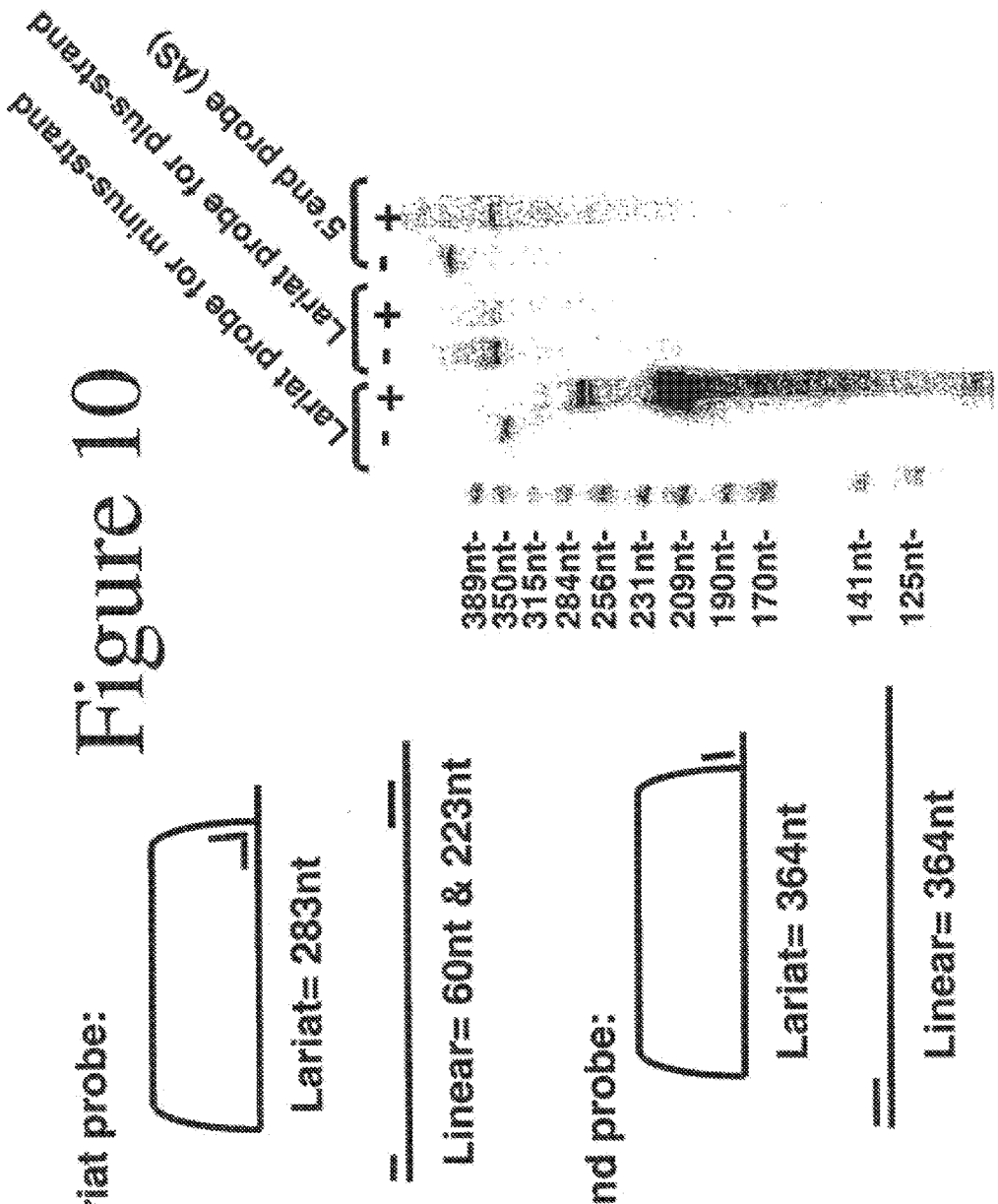

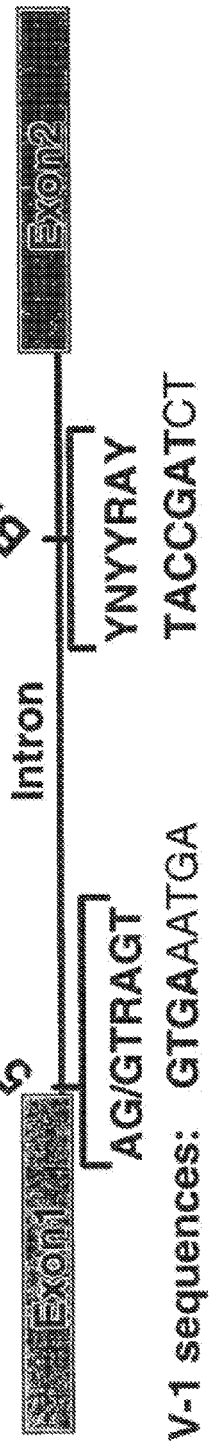
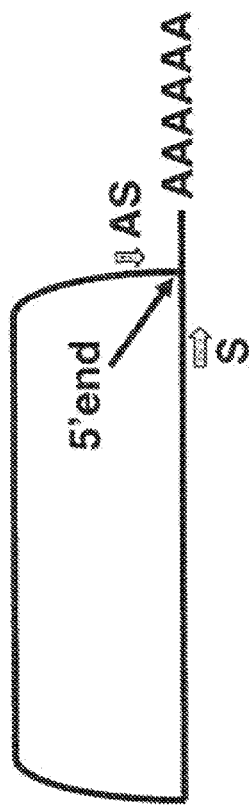
Splice site and branchpoint of MNV-1 genome
Figure 11
MNV-1 sequences: GTGAAATGA TACGATCT
R = A or G
Y = C or T

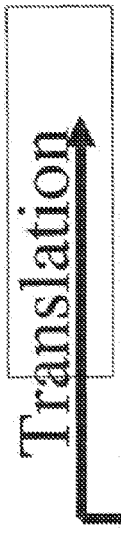
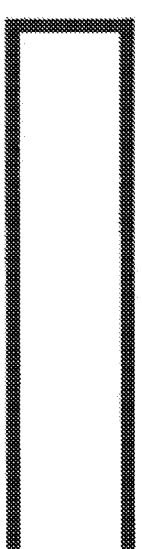
Figure 12

FIGURE 21

NOROVIRUS DETECTION, METHODS AND COMPOSITIONS THEREFOR

CROSS REFERENCE TO RELATED APPLICATIONS

This application is a Continuation of application Ser. No. 11/122,944 filed on May 5, 2005 now abandoned and claims priority to U.S. Provisional patent application No. 60/568, 301, filed May 5, 2004. These applications are incorporated in their entirety by reference.

GOVERNMENTAL INTEREST

This Invention was made with government support under U.S.P.H.S. Grant RO1 AI54483, awarded by the National Institute of Health. The U.S. Government has certain rights in the invention.

FIELD

This invention relates generally to the field of virology, and, more particularly, to methods and uses for norovirus culture and norovirus replicative forms.

BACKGROUND

Norovirus, which is a single-stranded, positive strand RNA virus belonging to the family calciviridae, causes over 90% of non-bacterial epidemic gastroenteritis worldwide. However, norovirus has been poorly understood because of a lack of a cell culture system supporting norovirus replication (Atmar, R. L. and Estes, M. K., Clinical Microbiology Reviews 14: 15-37, 2001). Norovirus, including human forms of norovirus (i.e., Norwalk virus), can be detected in stool specimens, sputum, blood or vomitus of diseased individuals. Norovirus can also be present in body tissues, such as brain tissue, in an infected mammalian organism. Previous attempts to culture norovirus have been unsuccessful (Duizer E, et al. J Gen Virol. 85(Pt 1): 79-87, 2004). There is thus a need to establish a norovirus culture system and to use such a system to identify the mechanisms of replication and translation of these important human viruses.

SUMMARY

Accordingly, the present inventors have succeeded in discovering methods for culturing norovirus and in developing norovirus-permissive host cells. The culture methods can be used for a variety of purposes, such as diagnostic methods, development of assays for viral replication, selection of mutant viruses with desirable properties, screening of potential anti-viral compounds, and development of vaccines.

The present inventors have also succeeded in identifying a replicative form of an RNA virus genome, such as a norovirus genome. The identification of this replicative form provides the basis for the development of new methods and agents for treating viral infection, as well as the development of new methods for expressing polypeptides. This replicative form has a close resemblance to RNA forms involved in the mammalian cell splicing machinery and as such provides insight into fundamental host cell processes emulated by a virus. In the lariat configuration, the 5' end of the genome is adjacent to, and downstream of, the highly active subgenomic RNA promoter of the virus. Hence, the virus can use the subgenomic RNA promoter to make both at least one single stranded subgenomic RNA and a full length genome. It therefore can comprise a eukaryotic expression system, wherein a heterologous gene is expressed under the control of a subgenomic RNA promoter.

The subgenomic RNA of the virus also has the potential to form a lariat. This is because the 5' end of the genome is highly conserved with the 5' end of the subgenomic RNA. That is, the sequences at the 5' end that are similar to splicing intermediates are highly related to the 5' end of the subgenomic RNA. Thus, an infected cell can comprise more than one viral-derived lariat.

In various embodiments, the present invention can comprise a norovirus-permissive cell culture infected with a norovirus. Such norovirus-permissive cell cultures can be comprised of vertebrate cells, in particular hematopoietic cells such as macrophage-lineage cells and dendritic cell-lineage cells. The macrophage-lineage cells can be, for example, bone marrow macrophages, umbilical cord macrophages, peripheral blood mononuclear cells, human leukocyte/mouse macrophage hybrid cells and embryonic stem cell macrophages.

In certain embodiments, the macrophages that can support norovirus replication can be macrophages deficient in one or more anti-viral pathways. The deficiency in a cellular anti-viral pathway can be a deficiency in a STAT-1-dependent anti-viral pathway (Darnell, J. E. et al., Science 264: 1415-1421, 1994) a deficiency in an interferon receptor-dependent anti-viral pathway, a deficiency in a double-stranded RNA-dependent serine/threonine protein kinase (PKR)-dependent anti-viral pathway (Hovanessian, A. G. Semin. Virol. 4, 237-245, 1993), or combinations thereof. Accordingly, macrophages which can support norovirus replication can be STAT-1-deficient macrophages, PKR-deficient macrophages, interferon receptor-deficient macrophages, or a combination thereof. The interferon receptor deficient macrophages can be deficient in an interferon-$\alpha\beta$ receptor, deficient in an interferon-$\gamma$ receptor, deficient in an interferon $\gamma$ receptor, or a combination thereof. Macrophages deficient in the PKR-dependent anti-viral pathway can be macrophages deficient in PKR.

In certain configurations, the macrophage lineage cells can be transformed macrophages. In some aspects, transformed macrophages can be established macrophage cell lines such as RAW 264.7 cells, J774A.1 cells or WBC264-9C cells (a human leukocyte/mouse macrophage hybrid cell line).

In certain configurations, the dendritic cell lineage cells can be bone marrow dendritic cells, peripheral blood dendritic cells, or transformed dendritic cells.

In some embodiments, the vertebrate cells can be murine cells, while in other embodiments, the vertebrate cells can be human cells or hybrid cells such as human-mouse fusion cells. In some configurations, a norovirus can be a murine norovirus, while in other configurations, a norovirus can be a human norovirus such as a Norwalk virus.

In various embodiments, the present invention can involve methods of replicating a norovirus in vitro. The methods can comprise inoculating norovirus-permissive cells with a norovirus, and culturing the cells. In these embodiments, inoculating norovirus-permissive cells can comprise infecting the cells with the norovirus, or transfecting the norovirus-permissive cells with a nucleic acid comprising a norovirus genome or a portion thereof comprising at least 25 nucleotides. In various configurations, the methods can comprise inoculating vertebrate cells which can be macrophage-lineage cells or dendritic cell-lineage cells. The macrophage-lineage cells which can be inoculated can be macrophage-lineage cells deficient in a cellular anti-viral pathway such as a STAT-1-dependent anti-viral pathway, an interferon receptor-dependent anti-viral pathway, a PKR-dependent anti-viral pathway, or a combination thereof. The macrophages deficient in an interferon-dependent pathway which can be inoculated can be deficient in an interferon-αβ receptor, an interferon-γ receptor, an interferon γ receptor or a combination thereof. The macrophages deficient in the PKR-dependent pathway which can be inoculated can be PKR-deficient macrophages. In some configurations, the macrophage-lineage cells which can be inoculated can be transformed macrophages such as RAW 264.7 cells, J774A.1 cells or WBC264-9C cells. In certain configurations, the norovirus-permissive cells which can be inoculated with norovirus can be dendritic cells such as bone marrow dendritic cells, peripheral blood dendritic cells, and transformed dendritic cells. In various embodiments of the invention, the cells that can be inoculated with norovirus can be vertebrate cells such as human cells, murine cells, or human-murine fusion cells, and the norovirus can be a murine norovirus or a human norovirus such as a Norwalk virus.

In various embodiments, the invention comprises methods of detecting norovirus in a biological sample. In one aspect, such methods can involve contacting a cell culture comprising norovirus-permissive cells with the sample, and detecting norovirus viral replication in the cell culture. The sample in some configurations can be a diagnostic sample, such as a diagnostic sample from a mammal suspected of infection with the norovirus. The mammal can be a human, a laboratory animal such as a rodent, a farm animal, or a companion animal. The diagnostic sample can be a tissue sample, a blood sample, a vomitus sample, a sputum sample or a stool sample. The norovirus-permissive cells in these embodiments can be dendritic cell-lineage cells or macrophage-lineage cells. The macrophage-lineage cells can be macrophages deficient in a cellular anti-viral pathway such a STAT-1-dependent anti-viral pathway, an interferon receptor-dependent anti-viral pathway, a PKR-dependent anti-viral pathway, or combinations thereof. In some configurations, the norovirus-permissive cells can be transformed macrophages selected from the group consisting of RAW 264.7 cells, J774A.1 cells and WBC264-9C cells.

In various configurations, methods of detecting norovirus in a biological sample can also involve performing a cytopathic assay, an antibody assay, a nucleic acid detection assay, or a protein detection assay. A cytopathic assay can be, in some configurations, a dye exclusion assay, an enzyme release assay, a necrosis assay or an apoptosis assay. In some configurations, an antibody assay can use a monoclonal or a polyclonal antibody, such as an antibody directed against a norovirus polypeptide and any antigen detection system known in the art, such as a Western blot assay, an ELISA assay, an immunofluorescence assay, an immunoprecipitation assay or a radioimmunoassay. In yet other configurations, a nucleic acid detection assay can be an assay such as a polymerase chain reaction assay, an RNase protection assay or a hybridization assay such as a Northern blot assay. In yet other configurations, a nucleic acid detection assay can be an assay such as a polymerase chain reaction assay, a Northern blot assay or an RNase protection assay that detects a lariat form of a viral genome.

In various embodiments, the invention can comprise methods of identifying a compound having anti-viral activity. In certain configurations, a method can comprise contacting the compound with a norovirus-permissive cell culture infected with a norovirus, and detecting inhibition of norovirus replication. Detecting inhibition of viral replication in these embodiments can comprise detecting inhibition of viral nucleic acid synthesis or viral protein synthesis. In some configurations, detecting inhibition of norovirus replication can comprise performing a plaque assay on the norovirus-permissive cell culture. In these configurations, the assays for identifying anti-viral compounds can be used for identifying compounds having anti-RNA virus activity, anti-single-stranded RNA virus activity, anti-positive strand single-stranded RNA virus activity, anti-positive strand single-stranded RNA, no DNA stage virus activity, anti-calicivirus activity, or anti-norovirus activity. A norovirus infecting a norovirus-permissive cell in these methods can be, in certain configurations, a norovirus comprising a nucleic acid consisting of from about 7200 to about 7700 nucleotides and wherein the norovirus nucleic acid hybridizes under high stringency conditions to a nucleic acid consisting of the sequence set forth in SEQ ID NO: 1.

In various embodiments, the invention can comprise a host range-modified norovirus. In some configurations, a host range-modified norovirus can be a norovirus adapted for growth in fibroblasts or macrophage-lineage cells which are not anti-viral pathway-deficient. In certain aspects, a host range-modified Norovirus can exhibit reduced virulence compared to non-adapted norovirus infecting the same host cells. A host range-modified norovirus of these embodiments can be, in certain aspects, a norovirus comprising an RNA of at least about 7200 to about 7700 nucleotides, wherein the RNA consists of a nucleotide sequence at least 80% identical to the RNA of the norovirus deposited on Apr. 27, 2004 with ATCC as Accession Number PTO-5935. A host range-modified norovirus can have a reduced virulence against a host organism compared to a non-adapted norovirus. In certain configurations, a host range-modified norovirus can be used for vaccination against norovirus infection. Hence, a norovirus vaccine can comprise a therapeutically effective amount of a host range-modified norovirus.

In various embodiments, the invention comprises methods of adapting norovirus to have a modified host range. The methods can also comprise serially passaging a norovirus population for three or more generations in norovirus-permissive cell cultures. The serially passaging can comprise plaque-purifying a norovirus and growing the plaque-purified norovirus in norovirus-permissive host cells for three or more serial passages.

In some embodiments, the invention includes cDNA of norovirus genomic RNA. A cDNA in these embodiments can be single-stranded or double-stranded, and can be comprised by a vector, such as a plasmid or viral vector. In some configurations, a cDNA of a norovirus genomic RNA can comprise an infectious clone. In certain aspects, a cDNA of a norovirus genomic RNA can comprise a partial cDNA, such as, for example, a subgenomic replicon. A vector comprising a subgenomic replicon can further comprise a reporter sequence, for example a reporter sequence encoding an enzyme or a green fluorescent protein. Such constructs can be used to test the efficacy of a candidate anti-viral compound. In some embodiments, a subgenomic portion can comprise, in non-limiting example, a sequence encoding a viral protein, a sequence involved in viral assembly, or a sequence involved in viral transcription or viral genome replication. A subgenomic portion can also be linked to an indicator sequence such as a sequence encoding a reporter polypeptide, for example a polypeptide encoding an enzyme or a fluorescent protein.

In some embodiments, a replicon can comprise an anti-viral agent. In some configurations of these embodiments, a replicon can comprise a viral RNA promoter. In some configurations a plasmid can comprise a promoter operably linked to a cDNA of viral sequence encoding an RNA promoter. In these configurations, the RNA promoter can be transcribed by the host cell to provide a negative sense copy of the viral RNA promoter. Upon infection or transfection or the cell with a virus, the negative sense copy of the promoter can act as a template molecule for a virally-encoded RNA-dependent RNA polymerase, thereby leading to the cell making RNA copies of subgenomic plus sense RNA. In some configurations, the amount of subgenomic RNA can be sufficiently great to compete with the viral RNA for cell or viral components used in viral replication, and thereby inhibit viral replication.

In some embodiments, the invention can comprise a replicon construct which can be used for viral detection. A replicon construct can, in these embodiments, be used, for example, to measure virus burden in a patient such as a human patient. In some configurations of these embodiments, a plasmid expresses a replicon under the control of a (DNA) promoter. A replicon can comprise a viral RNA promoter operably linked to a reporter sequence, for example a sequence encoding an enzyme or a fluorescent protein. In these configurations, the host cell accumulates negative sense viral RNA, although the RNA promoter is not expressed in a host cell in the absence of a stimulus such as an infecting virus. A sequence encoding a reporter molecule can be operably linked to this sequence, in frame with the initiation codon. In the absence of infection, the replicon can be transcribed by the host cell to provide a negative sense copy of the viral RNA promoter. Upon infection or transfection of the cell with a virus, the negative sense copy of the promoter can act as a template molecule for a virally-encoded RNA-dependent RNA polymerase, thereby leading to a host cell making RNA copies of subgenomic plus sense RNA, including a plus-sense copy of the sequence encoding a reporter. Reporter amount can be monotonically related to amount of infecting virus. Measurement of reporter amount, for example through measurement of enzyme activity or fluorescence of a fluorescent protein, can be used to measure viral burden. In some configurations of these embodiments, a plasmid can comprise a 5' end of an RNA virus genome, such as a norovirus genome, through a translation initiation codon (ATG) such as the initiation codon most proximal to the 5' end, or the initiation codon that is comprises by the second or additional open reading frame of the norovirus genome.

In some embodiments, the invention includes methods of inhibiting RNA virus replication based upon the inventors' discovery of a novel replicative form. This replicative form is topologically a lariat, akin to a splicing intermediate formed during eukaryotic messenger RNA processing (Patel and Steitz, Nature Reviews Molecular Cell Biology 4: 960-970, 2003). In a lariat form of a virus such as a norovirus, a 5'-2' linkage is formed between the 5' terminal nucleotide and an internal nucleotide. In addition, 5' sequences and sequences near the linkage site resemble those of known intervening sequences that are involved in forming lariat structures during intron splicing. Thus, it is believed that an RNA virus such as a norovirus uses a host cell's splicing "machinery" during its life cycle. This machinery involves a large number of molecular components, including over 100 polypeptides as well as RNA molecules such as snRNAs (Patel and Steitz, supra). Hence, viral gene expression and/or viral RNA replication can involve the lariat structure, and, accordingly, interfering or blocking the formation of the lariat, functioning of the lariat, or disassembly of the lariat can interfere with virus life cycle. The lariat, as well as the biomolecules involved in its formation, use, or disassembly, therefore provide targets for anti-viral agents. These biomolecules can be components of a spliceosome or a small nuclear ribonucleoprotein molecule (snRNP). Hence, in some embodiments, the invention provides methods of inhibiting RNA virus replication. A method of these embodiments can comprise contacting an RNA virus-infected cell with a compound that inhibits or interferes with the function of spliceosome component such as, for example, a debranching enzyme.

In some embodiments, the invention can be a method of inhibiting RNA virus replication, wherein the method comprises contacting an RNA virus-infected cell with an inhibitor of lariat formation, wherein the cell comprises an RNA virus nucleic acid replicative form comprising at least one 5'-2' phosphodiester bond. The RNA virus nucleic acid replicative form comprising at least one 5'-2' phosphodiester bond can comprise a lariat. The inhibitor of lariat formation can be, in some configurations, an inhibitor of an enzyme that catalyzes one or more steps in lariat formation. In some configurations, an inhibitor of lariat formation can comprise a nucleobase polymer. The nucleobase polymer can comprise one or more sequences sharing sequence identity with viral sequences expected to participate in lariat formation or function. The nucleobase polymer can comprise, for example, a sequence found in a norovirus or a norovirus replicative form, such as GTGAAATGA (SEQ ID NO: 2), GTGAAATGAGG (SEQ ID NO: 3), TACCGATCT (SEQ ID NO: 4), CTACCGATCTCGGG (SEQ ID NO: 5), GTGAAATGAGGTACCGAT (SEQ ID NO: 6) or a complement thereof. In some configurations, an inhibitor of lariat formation can comprise a nucleobase polymer which is topologically a Y-shaped nucleobase polymer or a lariat-shaped nucleobase polymer. In various configurations, the nucleobase polymer can be an RNA or a DNA, and comprise at least one internal L-2'-O-methyl ribopyrimidine subunit, a 3'-terminal L-2'-deoxycytidine subunit, and/or an arabino-adenosine branch point. In various embodiments, the inhibitor of lariat formation can comprise a nucleobase polymer comprising a sequence of at least about 10 contiguous nucleobases of a sequence of a lariat branch point of the RNA virus nucleic acid replicative form or the complement thereof, such as, for example, the sequence TACCGATCG (SEQ ID NO: 7); a nucleobase polymer comprising a sequence of at least about 10 contiguous nucleobases of a sequence 5' to a lariat branch point of the RNA virus nucleic acid replicative form or the complement thereof, such as, for example, the sequence GTGAAATGA (SEQ ID NO: 2), or a nucleobase polymer comprising a sequence of at least about 10 nucleobases of a sequence 3' to a lariat branch point of the RNA virus nucleic acid replicative form or the complement thereof, such as, for example, all or part of the sequence (SEQ ID NO: 8)
ATCAATATCAAAACGGCGCAGCTCCAGGCCGCAGGCTTTTCAAAGAC.

In some embodiments, the invention can be a method of inhibiting RNA virus replication, wherein the method comprises contacting an RNA virus-infected cell with an inhibitor of lariat debranching, wherein the cell comprises an RNA virus nucleic acid replicative form comprising at least one 5'-2' phosphodiester bond. The RNA virus nucleic acid replicative form comprising at least one 5'-2' phosphodiester bond can comprise a lariat. The inhibitor of lariat debranching can be, in some configurations, a debranching enzyme inhibitor.

In some configurations, an inhibitor of lariat debranching such as, for example, an inhibitor of a debranching enzyme can comprise a nucleobase polymer. The nucleobase polymer can comprise one or more sequences sharing sequence identity with viral sequences expected to participate in lariat formation or function. The nucleobase polymer can comprise, for example, a sequence found in a norovirus or a norovirus replicative form, such as GTGAAATGA (SEQ ID NO: 2), GTGAAATGAGG (SEQ ID NO: 3), TACCGATCT (SEQ ID NO: 4), CTACCGATCTCGGG (SEQ ID NO: 5), GTGAAATGAGGTACCGAT (SEQ ID NO: 6) or a complement thereof. In some configurations, an inhibitor of lariat debranching can comprise a nucleobase polymer which is topologically a Y-shaped nucleobase polymer or a lariat-shaped nucleobase polymer. In various configurations, the nucleobase polymer can be an RNA or a DNA, and comprise at least one internal L-2'-O-methyl ribopyrimidine subunit, a 3'-terminal L-2'-deoxycytidine subunit, and/or an arabino-adenosine branch point. In various embodiments, the debranching enzyme inhibitor can comprise a nucleobase polymer comprising a sequence of at least about 10 contiguous nucleobases of a sequence of a lariat branch point of the RNA virus nucleic acid replicative form or the complement thereof, such as, for example, the sequence TACCGATCG (SEQ ID NO: 7); a nucleobase polymer comprising a sequence of at least about 10 contiguous nucleobases of a sequence 5' to a lariat branch point of the RNA virus nucleic acid replicative form or the complement thereof, such as, for example, the sequence GTGAAATGA (SEQ ID NO: 2), or a nucleobase polymer comprising a sequence of at least about 10 nucleobases of a sequence 3' to a lariat branch point of the RNA virus nucleic acid replicative form or the complement thereof, such as, for example, all or part of the sequence

```
                                        (SEQ ID NO: 8)
ATCAATATCAAAACGGCGCAGCTCCAGGCCGCAGGCTTTTGAAAGAC.
```

In various embodiments, the RNA virus that forms a lariat structure upon infection of a permissive cell can be a single-stranded RNA virus; a positive strand single-stranded RNA virus; a positive strand single-stranded RNA virus, no DNA stage; a calicivirus; or a norovirus such as a human norovirus or a murine norovirus such as MNV-1.

In some embodiments, the invention provides a method of translating a nucleic acid encoding a polypeptide. In these embodiments, the method can comprise inoculating an RNA virus-permissive cell with a viral nucleic acid which forms a lariat structure operatively linked to a sequence encoding the polypeptide, and incubating the cell. In these methods, the RNA virus translation initiation sequence can comprise a lariat branch point sequence, such as, for example, GTGAAATGAG (SEQ ID NO: 9). Alternatively, the RNA virus translation initiation sequence can be an RNA virus ribosome binding site, such as, for example, an RNA virus internal ribosome entry site (IRES). In some configurations, the RNA virus translation initiation sequence, including an ATG translation initiation codon, can comprise a sequence including an ATG start codon, such as, for example, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO:26, or SEQ ID NO: 27, as follows:

```
                                        (SEQ ID NO: 10)
CAGCTCCAGGCCGCAGGCTTTTCAAAGACGGATGCCGCACGCCTTGCCTT

GGGGCAGCAGCCCACGAGGGCCGTGGATTGGTCTGGGACGCGGTACTACA

CCGCTAACCAGCCAGTCACGGGCTTCTCGGGTGGCTTTACCCCAACCTAC

ACTCCAGGTAGGCAAGTGACATCCCGCCCTGTGGACACATCCCCTCTACC

GATCTGTGAAATG;
```

-continued

```
                                        (SEQ ID NO: 11)
CCGCAGGCTTTTCAAAGACGGATGCCGCACGCCTTGCCTTGGGGCAGCAG

CCCACGAGGGCCGTGGATTGGTCTGGGACGCGGTACTACACCGCTAACCA

GCCAGTCACGGGCTTCTCGGGTGGCTTTACCCCAACCTACACTCCAGGTA

GGCAAGTGACATCCCGCCCTGTGGACACATCCCCTCTACCGATCTGTGAA

ATG;

(SEQ ID NO: 12)
TTCAAAGACGGATGCCGCACGCCTTGCCTTGGGGCAGCAGCCCACGAGGG

CCGTGGATTGGTCTGGGACGCGGTACTACACCGCTAACCAGCCAGTCACG

GGCTTCTCGGGTGGCTTTACCCCAACCTACACTCCAGGTAGGCAAGTGAC

ATCCGGCCCTGTGGACACATCCCCTCTACCGATCTGTGAAATG;

(SEQ ID NO: 13)
GATGCCGCACGCCTTGCCTTGGGGCAGCAGCCCACGAGGGCCGTGGATTG

GTCTGGGACGCGGTACTACACCGCTAACCAGCCAGTCACGGGCTTCTCGG

GTGGCTTTACCCCAACCTACACTCCAGGTAGGCAAGTGACATCCCGCCCT

GTGGACACATCCCCTCTACCGATCTGTGAAATG;

(SEQ ID NO: 14)
GCCTTGCCTTGGGGCAGCAGCCCACGAGGGCCGTGGATTGGTCTGGGACG

CGGTACTACACCGCTAACCAGCCAGTCACGGGCTTCTCGGGTGGCTTTAC

CCCAACCTACACTCCAGGTAGGCAAGTGACATCCCGCCCTGTGGACACAT

CCCCTCTACCGATCTGTGAAATG;

(SEQ ID NO: 15)
GGGGCAGCAGCCCACGAGGGCCGTGGATTGGTCTGGGACGCGGTACTACA

CCGCTAACCAGCCAGTCACGGGCTTCTCGGGTGGCTTTACCCCAACCTAC

ACTCCAGGTAGGCAAGTGACATCCCGCCCTGTGGACACATCCCCTCTACC

GATCTGTGAAATG;

(SEQ ID NO: 16)
CCCACGAGGGCCGTGGATTGGTCTGGGACGCGGTACTACACCGCTAACCA

GCCAGTCACGGGCTTCTCGGGTGGCTTTACCCCAACCTACACTCCAGGTA

GGCAAGTGACATCCCGCCCTGTGGACACATCCCCTCTACCGATCTGTGAA

ATG;

(SEQ ID NO: 17)
CCGTGGATTGGTCTGGGACGCGGTACTACACCGCTAACCAGCCAGTCACG

GGCTTCTCGGGTGGCTTTACCCCAACCTACACTCCAGGTAGGCAAGTGAC

ATCCCGCCCTGTGGACACATCCCCTCTACCGATCTGTGAAATG;

(SEQ ID NO: 18)
GTCTGGGACGCGGTACTACACCGCTAACCAGCCAGTCACGGGCTTCTCGG

GTGGCTTTACCCCAACCTACACTCCAGGTAGGCAAGTGACATCCCGCCCT

GTGGACACATCCCCTCTACCGATCTGTGAAATG;

(SEQ ID NO: 19)
CGGTACTACACCGCTAACCAGCCAGTCACGGGCTTCTCGGGTGGCTTTAC

CCCAACCTACACTCCAGGTAGGCAAGTGACATCCCGCCCTGTGGACACAT

CCCCTCTACCGATCTGTGAAATG;
```

```
                                                  (SEQ ID NO: 20)
CCGCTAACCAGCCAGTCACGGGCTTCTCGGGTGGCTTTACCCCAACCTAC

ACTCCAGGTAGGCAAGTGACATCCCGCCCTGTGGACACATCCCCTCTACC

GATCTGTGAAATG;

(SEQ ID NO: 21)
GCCAGTCACGGGCTTCTCGGGTGGCTTTACCCCAACCTACACTCCAGGTA

GGCAAGTGACATCCCGCCCTGTGGACACATCCCCTCTACCGATCTGTGAA

ATG;

(SEQ ID NO: 22)
GGCTTCTCGGGTGGCTTTACCCCAACCTACACTCCAGGTAGGCAAGTGAC

ATCCCGCCCTGTGGACACATCCCCTCTACCGATCTGTGAAATG;

(SEQ ID NO: 23)
GTGGCTTTACCCCAACCTACACTCCAGGTAGGCAAGTGACATCCCGCCCT

GTGGACACATCCCCTCTACCGATCTGTGAAATG;

(SEQ ID NO: 24)
CCCAACCTACACTCCAGGTAGGCAAGTGACATCCCGCCCTGTGGACACAT

CCCCTCTACCGATCTGTGAAATG;

(SEQ ID NO: 25)
ACTCCAGGTAGGCAAGTGACATCCCGCCCTGTGGACACATCCCCTCTACC

GATCTGTGAAATG;

(SEQ ID NO: 26)
GGCAAGTGACATCCCGCCCTGTGGACACATGCCCTCTACCGATCTGTGAA

ATG;

(SEQ ID NO: 27)
GTGGACACATCCCCTCTACCGATCTGTGAAATG.
```

In some embodiments, the invention provides a method of translating a nucleic acid encoding a polypeptide. In these embodiments, the method can comprise inoculating a eukaryotic cell with a nucleic acid comprising an RNA lariat-forming sequence of an RNA virus linked to a sequence encoding the polypeptide wherein the polypeptide is heterologous to the virus, and incubating the cell. In these embodiments, the eukaryotic cell can be, for example, an animal cell, which can be, for example, a mammalian cell, which can be, for example, an RNA virus-permissive cell, which can be, for example, a norovirus-permissive cell. In these methods, the RNA virus translation initiation sequence can comprise viral translation initiation sequence, including an ATG translation initiation codon, can comprise a sequence such as, for example, SEQ ID NO: 28, SEQ ID NO: 29, SEQ ID NO: 30, SEQ ID NO: 31, SEQ ID NO: 32, SEQ ID NO: 33, as follows.

```
                                                  (SEQ ID NO: 28)
TAGTCCCCACGCCACCGATCTGTTTTGCGCTGGGTGCGCTTTGGAAAATG

GATGCTGAGACCCCGCAGGAACGCTCAGCAGTCTTTGTGAATG;

(SEQ ID NO: 29)
GCCACCGATGTGTTTTGCGCTGGGTGCGGTTTGGAAAATGGATGCTGAGA

CCCCGCAGGAACGCTCAGCAGTGTTTGTGAATG;

(SEQ ID NO: 30)
TGTTTTGCGCTGGGTGCGCTTTGGAAAATGGATGCTGAGACCCCGCAGGA

ACGCTCAGCAGTCTTTGTGAATG;

(SEQ ID NO: 31)
TGGGTGCGCTTTGGAAAATGGATGCTGAGACCCCGCAGGAACGCTCAGCA

GTCTTTGTGAATG;

(SEQ ID NO: 32)
TTGGAAAATGGATGCTGAGACCCCGCAGGAACGCTCAGCAGTCTTTGTGA

ATG;

(SEQ ID NO: 33)
GATGCTGAGACCCCGCAGGAACGCTCAGCAGTCTTTGTGAATG.
```

In certain embodiments, the lariat junction can be located downstream of a subgenomic promoter. The subgenomic promoter can be a highly active promoter which is believed to support transcription at a rate at least that of a beta-actin promoter. Therefore it is believed that a subgenomic RNA comprising a lariat structure exists and can transcribe genes. Hence, a subgenomic RNA can be used to transcribe heterologous genes, such as genes encoding polypeptides which are useful, for example medically useful polypeptides.

In certain embodiments, the RNA virus-permissive cell can be a single stranded RNA virus-permissive cell, a positive strand single stranded RNA virus-permissive cell, a positive strand single stranded RNA virus, no DNA stage-permissive cell, a calicivirus-permissive cell, or a norovirus-permissive cell. For example, a norovirus-permissive cell can be a macrophage-lineage cell, a dendritic cell-lineage cell, or any other norovirus-permissive cell discussed herein.

In various configurations, the RNA virus translation initiation sequence can be a single-stranded RNA virus translation initiation sequence, a positive strand single-stranded RNA virus translation initiation sequence, a positive strand single-stranded RNA virus, no DNA stage translation initiation sequence, a calicivirus translation initiation sequence, or a norovirus translation initiation sequence. In certain configurations, the translation initiation sequence can have at least about 80% sequence identity with SEQ ID NO: 10. In certain configurations, the translation initiation sequence can have the sequence designated SEQ ID NO: 10.

In various configurations, the nucleic acid can be an RNA or a DNA.

BRIEF DESCRIPTION OF THE DRAWINGS

FIG. 7 illustrates the 7382 nucleotide consensus sequence of an MNV-1, designated SEQ ID NO: 1.

FIG. 8 illustrates detection of the lariat form of the viral genome by PCR and sequencing.

FIG. 10 illustrates proof that the lariat exists by RNase protection showing the presence of a 283 nt specific for the lariat form of the viral genome.

FIG. 11 illustrates the sequence of the MNV-1 lariat site with a comparison to consensus sequences used in mammalian splicing.

FIG. 12 illustrates that the 5' end of norovirus and calicivirus genomes contain sequences that match the consensus sites for mammalian splicing. The same is true of the 5' ends of subgenomic RNAs derived from the same viruses.

FIG. 21 illustrates changes in virulence of plaque-purified MNV-1.

DETAILED DESCRIPTION

Figure 1:
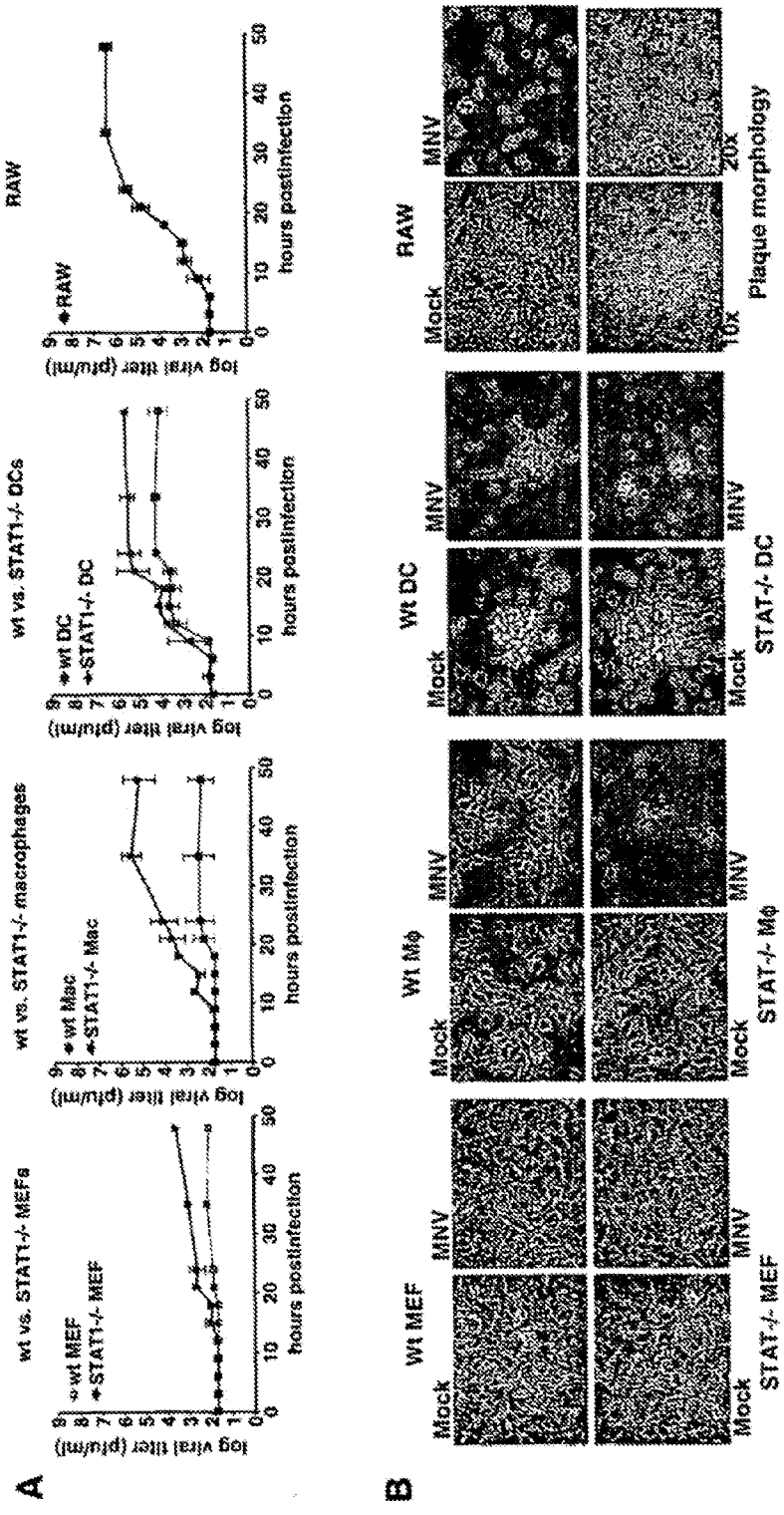
FIG. 1 illustrates productive infection in vitro by brain-derived norovirus of STAT-deficient macrophages, RAW 264.7 cells and dendritic cells.

Methods and compositions for culturing norovirus are described herein. The methods and compositions described herein utilize laboratory techniques well known to skilled artisans and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999. As used herein, in nucleic acid sequences a "T" represents a thymine if the sequence refers to a DNA sequence, or a uracil if the sequence refers to an RNA sequence. Similarly, a "U" represents a uracil if the sequence refers to an RNA sequence, or a thymine if the sequence refers to a DNA sequence.

The present inventors have succeeded in discovering a cell culture system for a norovirus. Development of their methods involved the discovery of norovirus-permissive host cells. As used herein, a "norovirus-permissive cell" is a cell in which a norovirus replicates following infection with a norovirus or transfection with norovirus genome RNA. As used herein, "norovirus replication" can be understood to include various stages in norovirus life cycle, such as, for example, binding of a norovirus to a host cell, entry into the host cell, trafficking, processing, genome release, translation, transcription, assembly, and release. In some embodiments, norovirus replication can be detected by measuring norovirus protein activity, for example polyprotein protease activity, viral RNA polymerase activity, VPG activity or NTPase activity. In some configurations, measurement of an increased accumulation of viral RNA or viral protein in infected cells can be considered an indication of viral replication, although an increase in virus particle production is not measured. Hence, in certain configurations, in a test of a candidate anti-viral agent, anti-viral activity can be detected by detecting inhibition of viral nucleic acid synthesis, or by detecting inhibition of a norovirus protein activity, such as inhibition of polyprotein protease activity, viral RNA polymerase activity, VPG activity or NTPase activity. Furthermore, in certain configurations, in a test of a candidate anti-viral agent, anti-viral activity can be detected by detecting inhibition of formation, disassembly or degradation of a viral RNA replicative intermediate such as a viral lariat structure. In other configurations, in a test of a candidate anti-viral agent, anti-viral activity can be detected by detecting inhibition of a norovirus protein accumulation, such as inhibition of polyprotein protease accumulation, viral RNA polymerase accumulation, VPG accumulation or NTPase accumulation.

The norovirus-permissive culture and the accompanying methods can be used for a variety of purposes, such as diagnostic methods, development of assays for viral replication, selection of mutant viruses with desirable properties, identification of mutant viruses, screening of potential anti-viral compounds, and development of vaccines.

As used herein, the term "norovirus" can refer to unmodified, wild-type norovirus, e.g., norovirus obtained from an individual with viral gastroenteritis, unless specified otherwise. As used herein, the term "host range-modified norovirus" refers to norovirus modified, with regard to its host range, using laboratory methods, e.g., norovirus grown in vitro for multiple passages.

In various embodiments, the present invention can comprise a norovirus-permissive cell culture infected with a norovirus. A norovirus permissive cell culture can be maintained using routine cell culturing techniques well known to skilled artisans. A norovirus-permissive cell culture can comprise vertebrate cells, such as macrophage-lineage cells and dendritic cell-lineage cells. As used herein, the term "macrophages" refers to mononuclear phagocytes found in tissues, and the term "dendritic cells" refers to reticular, immunocompetent antigen presenting cells of the lymphoid and haemopoietic systems and skin. Macrophage-lineage cells and dendritic cell-lineage cells can comprise hematopoietic-lineage cells that can be either mature in their differentiation state as macrophages or dendritic cells, respectively, or partially mature, i.e., macrophage or dendritic cell-like cells which exhibit some of the known characteristics of macrophages and dendritic cells. Macrophage-lineage cells and dendritic cell-lineage cells can also comprise precursor cells to mature macrophages or dendritic cells, such as, for example, peripheral blood monocytes or circulating dendritic cell-lineage precursor cells. Because treatment of macrophage-lineage cells or dendritic cell-lineage cells with cytokines, interleukins, chemokines, or other reagents (for example, CSF-1, GM-CSF, TNF-α, lipopolysaccharide (LPS) or CD40 Ligand) can influence the differentiation state of cells (e.g., Sapi E., Exp. Biol. Med. 229:1-11 2004; Dieu, M.-C. et al., J. Exp. Med. 188: 373-386, 1988) the differentiation state of many hematopoietic lineage cells can be altered by such treatments to become norovirus-permissive. Hence, macrophage-lineage cells can be, for example, macrophages or dendritic cells such as bone marrow macrophages or dendritic cells, umbilical cord macrophages or dendritic cells, and peripheral blood mononuclear cells. Norovirus-permissive cells can therefore include, for example, cytokine-stimulated macrophage-lineage cells such as, for example, cytokine-stimulated macrophages such as bone marrow macrophages, cytokine-stimulated umbilical cord macrophages, cytokine-stimulated peripheral blood mononuclear cells, and cytokine-stimulated peripheral blood macrophages or dendritic cells.

For example, mature, wild type macrophages harvested from peripheral blood but otherwise untreated may not be norovirus-permissive. However, treatment of such cells with an appropriate stimulus, such as, for example, a cytokine such as CSF-1, may alter the macrophages to become norovirus-permissive. In certain configurations, norovirus-permissive cells can be macrophages or dendritic cells derived from embryonic stem cells. The embryonic stem cells can be stimulated to become macrophages or dendritic cells using methods well known in the art (e.g., Senju, S. et al., Blood 101: 3501-3508, 2003).

In certain embodiments, macrophages and dendritic cells support norovirus replication. The macrophages which can support norovirus replication can be macrophages deficient in one or more anti-viral pathways. The deficiency in a cellular anti-viral pathway can be a deficiency in a STAT-1-dependent anti-viral pathway, a deficiency in an interferon receptor-dependent anti-viral pathway, a deficiency in a double-stranded RNA-dependent serine/threonine protein kinase (PKR) anti-viral pathway (Hovanessian, A. G. Semin. Virol. 4, 237-245, 1993), or combinations thereof. Accordingly, macrophages which can support norovirus replication can be, in some configurations, STAT-1-deficient macrophages, PKR-deficient macrophages, or interferon receptor-deficient macrophages. The interferon receptor deficient macrophages can be deficient in a Type I interferon response. In some configurations, a norovirus-permissive macrophage can be deficient for an interferon-αβ receptor, deficient for an interferon-γ receptor, deficient for an interferon λ receptor, or a combination thereof. Macrophages deficient in the PKR-dependent anti-viral pathway can be macrophages deficient in PKR.

In certain configurations, the macrophage lineage cells can be transformed macrophages. In some aspects, transformed macrophages can be established macrophage cell lines such as, for example, RAW 264.7 cells and J774A.1 cells, both of which are available from the American Type Culture Collection, P.O. Box 1549, Manassas Va. 20108.

In certain configurations, the dendritic cell lineage cells can be bone marrow dendritic cells, peripheral blood dendritic cells, or transformed dendritic cells. The dendritic cells can be from any stage or substage of dendritic cell development or differentiation (e.g., Herbst, B., et al., Br. J. Haematol. 99: 490-499, 1997).

In some embodiments, the vertebrate cells can be murine cells, while in other embodiments, the vertebrate cells can be human cells. Human cells can be, for example, human bone marrow macrophages or dendritic cells. In some configurations, a norovirus can be a murine norovirus, while in other configurations, a norovirus can be a human norovirus, such as a Norwalk virus.

In various embodiments, the present invention can involve methods of replicating a norovirus in vitro. The methods can comprise inoculating norovirus-permissive cells with a norovirus, and culturing the cells. In these embodiments, inoculating norovirus-permissive cells can comprise infecting the cells with the norovirus, or transfecting the norovirus-permissive cells with a nucleic acid comprising a norovirus genome or a portion thereof comprising at least 25 contiguous nucleotides. In some embodiments, inoculating norovirus-permissive cells with a norovirus can comprise inoculating the cells with DNA such as a cDNA of a norovirus genome or a portion thereof comprising at least 25 contiguous nucleotides. The cDNA of a norovirus can be comprised by a vector, such as, in non-limiting example, a bacteriophage or a plasmid. In certain aspects, the cDNA can comprise a replicon, or a sequence encoding a viral polypeptide. A vector can further comprise a promoter, which can be operatively linked to a sequence encoding a reporter polypeptide. In certain embodiments, a cDNA of a norovirus genome can be comprised by an infectious clone. In various configurations, the methods can comprise inoculating vertebrate cells which can be macrophage-lineage cells or dendritic cell-lineage cells. The macrophage-lineage cells which can be inoculated can be macrophage-lineage cells deficient in a cellular anti-viral pathway such as a STAT-1-dependent anti-viral pathway, an interferon receptor-dependent anti-viral pathway, a PKR-dependent anti-viral pathway, or a combination thereof. The macrophages deficient in an interferon pathway which can be inoculated can be deficient in an interferon-αβ receptor, an interferon-γ receptor, an interferon-λ) receptor or a combination thereof. The macrophages deficient in the PKR-dependent pathway which can be inoculated can be PKR-deficient macrophages. In some configurations, the macrophage-lineage cells which can be inoculated can be transformed macrophages such as RAW 264.7 cells and J774A.1 cells. Other macrophage-lineage cells, for example macrophage-lineage cells available from the American Type Culture Collection, can also be used to practice the methods of the invention. In certain configurations, the norovirus-permissive cells which can be inoculated with norovirus can be dendritic cells such as bone marrow dendritic cells, peripheral blood dendritic cells, and transformed dendritic cells.

In various embodiments of the invention, cells that can be inoculated with norovirus can be vertebrate cells such as human or murine cells, and the norovirus can be a murine norovirus or a human norovirus such as a Norwalk virus.

In some embodiments, detection of the lariat itself, using, for example, RT-PCR (real time polymerase chain reaction) provides a method for detecting the presence of the virus. Because the lariat is found in a host cell when the virus is replicating its RNA, detection of the lariat's presence can indicate that the virus is replicating, and hence the lariat's presence can serve as an indicator of viral replication. Accordingly, a reduction or elimination of a viral lariat from infected cells can serve as an indication of viral inhibition, for example in a test of a candidate anti-viral compound.

In various embodiments, the invention comprises methods of detecting norovirus in a biological sample. The methods can comprise contacting a cell culture comprising norovirus-permissive cells with the sample, and detecting norovirus viral replication in the cell culture. The sample in some configurations can be a diagnostic sample, such as a diagnostic sample from a mammal suspected of infection with the norovirus. The mammal can be a human, a laboratory animal such as a rodent, for example a mouse, a rat, or a guinea pig, a farm animal such as a cow or a sheep, or a companion animal such as a cat or dog. The diagnostic sample can be a tissue sample, a blood sample, or a stool sample. A tissue sample can be from any tissue or body fluid that is suspected of infection with a norovirus, such as, for example, liver, kidney, brain, blood, or saliva. The norovirus-permissive cells in these embodiments can be dendritic cell-lineage cells or macrophage-lineage cells. The macrophage-lineage cells can be macrophages deficient in a cellular anti-viral pathway such a STAT-1-dependent anti-viral pathway, an interferon receptor-dependent anti-viral pathway, a PKR-dependent anti-viral pathway, or combinations thereof. In some configurations, the macrophage-lineage cells can be transformed macrophages The transformed macrophages can be, for example, transformed macrophages selected from the group consisting of RAW 264.7 cells and J774A.1 cells. In various configurations, a method of detecting norovirus in a biological sample can comprise detecting a host cell change that results from norovirus infection. A host cell change can be, for example, a change in morphology, molecular composition, or cytopathicity. Hence, a method for detecting norovirus in a biological sample can comprise performing a cytopathic assay, an antibody assay, a protein detection assay or a nucleic acid detection assay. A cytopathic assay can be, in some configurations, a dye exclusion assay, an enzyme release assay, a necrosis assay, or an apoptosis assay. A dye exclusion assay can be, in non-limiting example, a trypan blue exclusion assay, or a fluorescent dye exclusion assay such as a propidium iodide exclusion assay. In some configurations, an antibody assay can use a monoclonal or a polyclonal antibody, such as a monoclonal antibody directed against a norovirus polypeptide, such as, for example, monoclonal antibody A6.2. Any antigen detection system known in the art, such as a Western blot assay, an ELISA assay, an immunofluorescence assay, an immunoprecipitation assay or a radioimmunoassay, can be used to detect the presence and/or quantity of a norovirus. In some configurations, a protein detection assay can comprise, in non-limiting example, a gel electrophoresis assay, a column chromatography assay, and an enzyme assay. In yet other configurations, a nucleic acid detection assay can be an assay such as a polymerase chain reaction assay or a hybridization assay such as a Northern blot assay, or an RNase protection assay. In a PCR assay, primers can be selected such that their target sequences are located on opposite sides of a lariat branch point. PCR amplification of a sample comprising a branch point can lead to synthesis of a DNA molecule of predicted size, which can be detected by standard methods such as agarose gel electrophoresis. In an RNase protection assay, a lariat in a sample can be detected by forming a mixture comprising the sample and a nucleic acid probe such as a single stranded RNA or DNA which is complementary to a branch point-spanning sequence of a lariat. The mixture can then be exposed to nuclease which selectively digests single-stranded nucleic acids compared to double-stranded nucleic acids. The nuclease can be an RNase, such as, for example, S1 nuclease. Protection of a double-stranded structure from nuclease digestion can be used for detection of the presence of a lariat in a sample. Similarly, Northern blot analysis can be used to detect the presence of a lariat. For example, a probe which hybridizes under high stringency conditions (as defined in Sambrook et al., supra) to the lariat can be used to detect the lariat.

In various embodiments, the invention comprises methods of identifying a compound having anti-viral activity. "Anti-viral activity," as used herein, can comprise inhibiting viral activity at any stage in a virus' life cycle. Hence, anti-viral activity can comprise, in non-limiting example, inhibition of viral replication, inhibition of viral gene expression, or inhibition of a viral protein accumulation or activity. Inhibition of a viral protein accumulation or activity can comprise, in non-limiting example, inhibition of norovirus polyprotein protease accumulation, inhibition of norovirus RNA polymerase accumulation, inhibition of norovirus VPG accumulation, inhibition of norovirus NTPase accumulation, inhibition of norovirus polyprotein protease activity, inhibition of norovirus RNA polymerase activity, inhibition of norovirus VPG activity inhibition of norovirus NTPase activity, inhibition of lariat formation, or inhibition of lariat degradation. Standard methods well known in the for measuring or detecting norovirus protein accumulation or activity can be used, for example, enzyme assays and antibody assays.

In certain configurations, a method for identifying a compound having anti-viral activity can comprise contacting a candidate anti-viral compound with a norovirus-permissive cell culture infected with a norovirus, and detecting inhibition of norovirus replication. In certain aspects, a candidate anti-viral compound can be added to an infected norovirus-permissive culture at a concentration of from about 1 picomolar to about 100 millimolar, or from about 1 nanomolar to about 100 micromolar. Detecting inhibition of viral replication in some embodiments can thus comprise detecting inhibition of viral nucleic acid synthesis or viral protein synthesis. In some configurations, detecting inhibition of norovirus replication can comprise performing a plaque assay on the norovirus-permissive cell culture. A plaque assay can comprise determining a titer of virus accumulated in a plaque formed by infected cells in the presence of the candidate anti-viral molecule. In these configurations, assays for identifying anti-viral compounds can be used for identifying compounds having anti-RNA virus activity, anti-single-stranded RNA virus activity, anti-positive strand single-stranded RNA virus activity, anti-positive strand single-stranded RNA, no DNA stage virus activity, anti-calicivirus activity, or anti-norovirus activity. A norovirus infecting a norovirus-permissive cell in these methods can be, in certain configurations, a norovirus comprising a nucleic acid consisting of from about 7200 to about 7700 nucleotides and wherein the norovirus nucleic acid hybridizes under high stringency conditions to a nucleic acid consisting of the sequence set forth in SEQ ID NO: 1. In some configurations, anti-viral activity can be detected by detecting differences between infected norovirus-permissive cells contacted with a candidate anti-viral agent and control infected norovirus-permissive cells. Such differences can comprise, in non-limiting example, gene expression differences, antigenic differences, enzyme activity differences, dye-staining differences, or morphological differences (as revealed by light microscopy or electron microscopy). In some configurations, anti-viral activity can be detected by performing a cytopathic effects (CPE) inhibition assay in which the anti-viral activity reduces or prevents norovirus-induced CPE.

In some embodiments, the invention includes cDNA of norovirus genomic RNA. A cDNA in these embodiments can be single-stranded or double-stranded, and can be comprised by a vector, such as a plasmid or viral vector. In some configurations, a cDNA of a norovirus genomic RNA can comprise an infectious clone. A partial or complete cDNA can be produced using a reverse transcription techniques well known to skilled artisans. In certain aspects, a cDNA of a norovirus genomic RNA can comprise a partial cDNA, such as, for example, an identified viral gene, a viral promoter, or a viral lariat branch point.

A subgenomic portion can comprise, in non-limiting example, a sequence encoding a viral protein, a sequence involved in viral assembly, or a sequence involved in viral transcription or viral genome replication. A subgenomic portion can also be linked to an indicator sequence such as a sequence encoding a reporter polypeptide, for example a polypeptide encoding an enzyme or a fluorescent protein.

In some embodiments, a replicon can comprise an anti-viral agent. In some configurations of these embodiments, a replicon can comprise a viral RNA promoter. In some configurations a plasmid can comprise a promoter operably linked to a cDNA of viral sequence encoding an RNA promoter. In these configurations, the RNA promoter can be transcribed by the host cell to provide a negative sense copy of the viral RNA promoter. Upon infection or transfection of the cell with a virus, the negative sense copy of the promoter can act as a template molecule for a virally-encoded RNA-dependent RNA polymerase, thereby leading to the cell making RNA copies of subgenomic plus sense RNA. In some configurations, the amount of subgenomic RNA can be sufficiently great to compete with the viral RNA for cell or viral components used in viral replication, and thereby inhibit viral replication.

In some embodiments, the invention can comprise a replicon construct which can be used for viral detection. A replicon construct can, in these embodiments, be used, for example, to measure virus burden in a patient such as a human patient. In some configurations of these embodiments, a plasmid expresses a replicon under the control of a (DNA) promoter. A replicon can comprise a viral RNA promoter operably linked to a reporter sequence, for example a sequence encoding an enzyme or a fluorescent protein. In these configurations, the host cell accumulates negative sense viral RNA, although the RNA promoter is not expressed in a host cell in the absence of a stimulus such as an infecting virus. A sequence encoding a reporter molecule can be operably linked to this sequence, in frame with the initiation codon. In the absence of infection, the replicon can be transcribed by the host cell to provide a negative sense copy of the viral RNA promoter. Upon infection or transfection of the cell with a virus, the negative sense copy of the promoter can act as a template molecule for a virally-encoded RNA-dependent RNA polymerase, thereby leading to a host cell making RNA copies of subgenomic plus sense RNA, including a plus-sense copy of the sequence encoding a reporter. Reporter amount can be monotonically related to amount of infecting virus. Measurement of reporter amount, for example through measurement of enzyme activity or fluorescence of a fluorescent protein, can be used to measure viral burden. In some configurations of these embodiments, a plasmid can comprise a 5' end of an RNA virus genome, such as a norovirus genome, through a translation initiation codon (ATG) such as the initiation codon most proximal to the 5' end, or the initiation codon that is comprises by the second or additional open reading frame of the norovirus genome.

In some configurations, a subgenomic replicon can comprise a viral lariat junction. In some configurations, a subgenomic replicon can comprise a viral RNA promoter. Hence, a subgenomic replicon can comprise a contiguous sequence of about at least ten to about 500 nucleotides, about at least ten to about 200 nucleotides, or about at least ten to about 1000 nucleotides, of viral sequence comprising an RNA promoter A vector comprising a subgenomic replicon can further comprise a reporter sequence, for example a reporter sequence encoding a polypeptide such as an enzyme or a green fluorescent protein. The enzyme can be, for example, a phosphatase such as an alkaline phosphatase, for example a secreted alkaline phosphatase. Such vectors can further comprise a DNA promoter operatively linked to the reporter. Such constructs can be transfected or transformed into a host cell, and used to test the efficacy of a candidate anti-viral compound. In some aspects, testing the efficacy of a candidate anti-viral compound can comprise contacting cells comprising a norovirus replicon with the candidate anti-viral compound, and detecting inhibition of replicon replication. The inhibition detection, in some configurations, can comprise detecting a reduction in reporter gene expression. The host cell, in these embodiments, can be, for example, a norovirus-permissive cell. In addition, such constructs can be used to measure the virus content of a biological sample, such as, for example, a stool or vomitus sample from a patient. For example, a cell line comprising a subgenomic replicon and a reporter gene can be contacted with a vomitus, blood, serum, or stool sample from a human patient, and the viral burden can be quantified by measuring the level of reporter gene expression.

In various embodiments, the invention comprises a host range-modified norovirus. In some configurations, a host range-modified norovirus can be a norovirus adapted for growth in fibroblasts or macrophage-lineage cells which are not anti-viral pathway-deficient. In certain aspects, a host range-modified norovirus can exhibit reduced virulence compared to non-adapted norovirus infecting the same host cells. A host range-modified norovirus of these embodiments can be, in certain aspects, a norovirus comprising an RNA of at least about 7200 to about 7700 nucleotides, wherein the RNA consists of a nucleotide sequence at least 80% identical to the RNA of the norovirus deposited with ATCC on Apr. 27, 2004 as Accession Number PTO-5935.

In some embodiments, the invention can comprise a viral form which lacks the capacity to make a lariat. This form can be a non-virulent form, i.e., can be harmless to a cell or an organism. Such forms can be used, for example, as vectors for expression of heterologous genes, or for production of a vaccine.

A host range-modified norovirus can have reduced virulence against a host cell or organism compared to a non-adapted norovirus. In certain configurations, a norovirus vaccine can comprise a therapeutically effective amount of a host range-modified norovirus. A therapeutically effective amount of a host range-modified norovirus for use as a vaccine can comprise, for example, from 1 to about 1,000,000 plaque forming units of a host range-modified norovirus. In certain configurations, a host range-modified norovirus can be a norovirus adapted to grow in a host cell that is approved by a government regulatory agency such as the US Food and Drug Administration for the production of a vaccine. An approved host cell can be, for example, Vero cells such as cells having an ATCC designation of No. CCL-81.

In various embodiments, the invention comprises methods of adapting norovirus to have a modified host range. The methods can comprise serially passaging a norovirus population for three or more generations in norovirus-permissive cell cultures. The serially passaging can comprise plaque-purifying a norovirus and growing the plaque-purified norovirus in norovirus-permissive host cells for two serial passages, three serial passages, or more serial passages. Hence, examples of host cells for a norovirus adapted to a modified host cell range can include not only RAW 264.7 cells, J774A.1 cells, anti-viral pathway-deficient macrophages and dendritic cells, but also fibroblasts such as embryonic fibroblasts, and wild type macrophages (i.e., macrophages that are not deficient in a cellular anti-viral pathway). In some configurations, adapting the host range-modified norovirus to growth in a vaccine production-approved cell line can comprise infecting the approved cell line with host range-modified norovirus, and growing the virus. Methods for producing a vaccine against a virus using a virus exhibiting reduced virulence through serial passage adaptation (Sabin, A. B., Ann. NY Acad. Sci. 61: 924-938, 1955) or through genetic engineering (e.g., by altering codons) are well known to skilled artisans.

In some embodiments, the invention includes methods of inhibiting RNA virus replication based upon the inventors' discovery of a novel replicative form. As used herein, the term "replicative form" refers to a viral nucleic acid form that appears in an infected cell. The use of the term does not imply that the form is necessarily a replication intermediate. A replicative form can also be, for example, a viral nucleic acid form that provides an active template for transcription. A replicative form can also be, for example, a viral nucleic acid form that provides an active template for translation of one or more polypeptides. The replicative form observed in a virus-permissive cell herein is topologically a lariat akin to a splicing intermediate formed during messenger RNA processing (Patel and Steitz, Nature Reviews Molecular Cell Biology 4: 960-970, 2003). In a lariat form of a virus such as a norovirus, a 5'-2' linkage is formed between the 5' terminal nucleotide and an internal nucleotide. In addition, 5' sequences and sequences near the branch point site can exhibit sequence similarity with sequences of introns which are involved in forming lariat structures during intron splicing. Thus, an RNA virus such as a norovirus uses its host cell's splicing 'machinery' during its life cycle. This 'machinery' involves a large number of molecular components, including over 100 polypeptides as well as RNA molecules such as snRNAs, (e.g., U1, U2, U4, U4atac, U5, U6, U6atac, U11 and U12; Patel and Steitz, supra). Hence, viral gene expression and/or viral RNA replication can involve the lariat structure. Accordingly, interfering or blocking the formation of the lariat, functioning of the lariat, or disassembly of the lariat can interfere with virus life cycle. The lariat, as well as the biomolecules involved in its formation, use, or disassembly, therefore provide targets for anti-viral agents. These biomolecules can be components of a spliceosome or a small nuclear ribonucleoprotein molecule (snRNP). Hence, in some embodiments, the invention provides methods of inhibiting RNA virus replication. A method of these embodiments can comprise contacting an RNA virus-infected cell with a compound that inhibits or interferes with the function of spliceosome component such as, for example, a debranching enzyme (Carriero and Damha, Nucleic Acids Research 31: 6157-6167, 2003). The compound can be, for example, an antibody directed against the lariat itself, against an snRNA, or a spliceosome polypeptide such as, for example, a branch point-binding protein such as SF1 (Arning et al., RNA 2, 794-810, 1996). In some configurations, the compound can be a sense or antisense nucleobase polymer such as, for example, an antisense RNA, an antisense DNA, or an antisense peptide nucleic acid (PNA). In some configurations, the compound can hybridize across a lariat junction. The antisense RNA or DNA oligonucleotide can, for example, hybridize to a branch point of the lariat form of the viral RNA. The sense or antisense nucleobase polymer can comprise from about 5 to about 100 bases, from about 10 to about 70 base, from about 15 to about 50 bases, or from about 20 to about 30 bases. The compound can also take the form of a short RNA or DNA, such as, for example, an interfering RNA (siRNA), a microRNA (miRNA), an snRNA or a complement thereof. In this connection, RNase protection assays show that a nucleic acid probe can anneal across the lariat junction.

It is believed that other RNA viruses, in addition to noroviruses can use a similar strategy in their life cycle. Other RNA viruses can be, for example, other single stranded RNA viruses, other positive sense single stranded RNA viruses, such as, for example, retroviruses, other positive sense single stranded RNA no DNA stage viruses, such as, for example, poliovirus, or other caliciviruses. Viruses using a similar strategy can be any virus that utilizes a subgenomic promoter, such as, for example, alphaviruses.

In some embodiments, the invention is a method of inhibiting RNA virus replication, wherein the method comprises contacting an RNA virus-infected cell with an inhibitor of the formation, function, or debranching of the lariat form of the viral genome. In non-limiting example, a method can comprise contacting an RNA virus-infected cell with a debranching enzyme inhibitor, wherein the cell comprises an RNA virus nucleic acid replicative form comprising at least one 5'-2' phosphodiester bond. The RNA virus nucleic acid replicative form comprising at least one 5'-2' phosphodiester bond can comprise a lariat.

In some configurations, an anti-viral agent can be a debranching enzyme inhibitor. Because the lariat branch point in the viral genome uses a T rather than an A as a donor nucleotide in a splicing reaction, this implies that there are novel activities encoded in the virus that alter the specificity of host splicing. Hence, in certain embodiments, and RNA virus such as a norovirus, a viral RNA such as a norovirus RNA, or a viral polypeptide such as a norovirus polypeptide can be used to alter host cell biology via alteration of the host splicing machinery. By altering host cell biology, a norovirus or a norovirus component can be used as a toxic protein or protein that alters the gene expression pattern of the cell.

Because the lariat branch point in the viral genome uses a T rather than an A as a nucleophile nucleotide in a splicing reaction, (although sequences close to the nucleophile nucleotide are similar or identical to sequences known to be involved in splicing) there can be novel activities encoded in the virus that alter the specificity of host splicing. Because there is a 5'-2' linkage in the lariat, and this linkage can be comprised by a branch point which also comprises a 5'-3' linkage, in some configurations, a ribosome encountering a lariat branch point comprising both a 5'-2' linkage and a 5'-3' linkage can face a choice of RNA sequence as template for translation. In some configuration, a ribosome encountering a lariat branch point comprising both a 5'-2' linkage and a 5'-3' linkage can 'jump' to the 5'-2' linkage. Hence, in certain embodiments, an RNA virus such as a norovirus, a norovirus RNA, or a norovirus polypeptide can be used to alter host cell biology. Because of these novel alterations in cell metabolism during norovirus infection, a norovirus or a norovirus component can be useful as a toxic protein or protein that alters the gene expression pattern of the cell. Hence, viral components which are used in the formation, utilization or disassembly of the lariat structure can be used to stimulate or inhibit the production of a host cell polypeptide, or be used to interfere with host cell RNA processing in therapeutic applications.

In some embodiments, an inhibitor of viral replication can be an inhibitor of the formation, function, or debranching of the lariat form of the viral genome. In certain configurations, an inhibitor of viral replication can comprise a nucleobase polymer. In some configurations, the nucleobase polymer can be a debranching enzyme inhibitor. In these configurations, the nucleobase polymer can comprise one or more sequences sharing sequence identity with viral sequences expected to participate in lariat formation or function. The nucleobase polymer can be an RNA, a DNA, a hybrid molecule, or an unnatural polymer such as, for example, a peptide nucleic acid (PNA). The sequence can be in a sense or an antisense configuration. One or more subunits of a nucleobase polymer of the invention can comprise a non-ribose sugar such as an arabinose. Linkages between nucleobases can include, in addition to 5'-3' linkages, linkages such as 5'-2' linkages, and linkages to non-ribose sugars such as arabinose. In some configurations, an inhibitor can comprise one or more non-standard bases, such as, for example, L-2'-deoxycytidine or 2'-O-ribopyrimidine. Since the 5' end of the MNV-1 and other viral genomes contains consensus sequences for mammalian splicing machinery and since the same sequences are present at the 5' end of the subgenomic and predicted subgenomic RNAs of viruses, a lariat form of viral RNA can comprise a subgenomic lariat or a full (genomic) length.

The nucleobase polymer can comprise, for example, a sequence found in a norovirus or a norovirus replicative form, such as GTGAAATGA (SEQ ID NO: 2), GTGAAATGAGG (SEQ ID NO: 3), TACCGATCT (SEQ ID NO: 4), CTAC-CGATCTCGGG (SEQ ID NO: 5), GTGAAATGAGGTAC-CGAT (SEQ ID NO: 6) or a complement thereof. In some configurations, a debranching enzyme inhibitor can comprise a nucleobase polymer which is topologically a Y-shaped nucleobase polymer or a lariat-shaped nucleobase polymer. In various configurations, the nucleobase polymer can be an RNA or a DNA, and comprise at least one internal L-2'-O-methyl ribopyrimidine subunit, a 3'-terminal L-2'-deoxycytidine subunit, and/or an arabino-adenosine branch point (Carriero and Damha, Nucleic Acids Research 31: 6157-6167, 2003). In various embodiments, the debranching enzyme inhibitor can comprise a nucleobase polymer comprising a sequence of at least about 10 contiguous nucleobases of a sequence of a lariat branch point of the RNA virus nucleic acid replicative form or the complement thereof, such as, for example, the sequence SEQ ID NO: 2; a nucleobase polymer comprising a sequence of at least about 10 contiguous nucleobases of a sequence 5' to a lariat branch point of the RNA virus nucleic acid replicative form or the complement thereof, such as, for example, the sequence SEQ ID NO: 3, or a nucleobase polymer comprising a sequence of at least about 10 nucleobases of a sequence 3' to a lariat branch point of the RNA virus nucleic acid replicative form or the complement thereof, such as, for example, the sequence SEQ ID NO: 4. In methods of the present invention, a debranching enzyme inhibitor can be one described in Carriero and Damha (supra). In some embodiments, these same sequences, or sequences sharing at least about 50%, sharing at least about 60%, sharing at least about 70%, sharing at least about 80% or sharing at least about 90% sequence similarity can inhibit lariat formation.

In certain configurations, an inhibitor of viral replication can comprise a nucleobase polymer. In some configurations, the nucleobase polymer can be an inhibitor of lariat formation. In these configurations, the nucleobase polymer can comprise one or more sequences sharing sequence identity with viral sequences expected to participate in lariat formation or function. The nucleobase polymer can be an RNA, a DNA, a hybrid molecule, or an unnatural polymer such as, for example, a peptide nucleic acid (PNA). The sequence can be in a sense or an antisense configuration. One or more subunits of a nucleobase polymer of the invention can comprise a non-ribose sugar such as an arabinose. Linkages between nucleobases can include, in addition to 5'-3' linkages, linkages such as 5'-2' linkages, and linkages to non-ribose sugars such as arabinose. In some configurations, an inhibitor can comprise one or more non-standard bases, such as, for example, L-2'-deoxycytidine or 2'-O-ribopyrimidine. Since the 5' end of the MNV-1 and other viral genomes contains consensus sequences for mammalian splicing machinery and since the same sequences are present at the 5' end of the subgenomic and predicted subgenomic RNAs of viruses, a lariat form of viral RNA can comprise a subgenomic lariat or a full (genomic) length.

The nucleobase polymer can comprise, for example, a sequence found in a norovirus or a norovirus replicative form, such as GTGAAATGA (SEQ ID NO: 2), GTGAAATGAGG (SEQ ID NO: 3), TACCGATCT (SEQ ID NO: 4), CTAC-CGATCTCGGG (SEQ ID NO: 5), GTGAAATGAGGTAC-CGAT (SEQ ID NO: 6) or a complement thereof. In some configurations, an inhibitor of lariat formation can comprise a nucleobase polymer which is topologically a Y-shaped nucleobase polymer or a lariat-shaped nucleobase polymer. In various configurations, the nucleobase polymer can be an RNA or a DNA, and comprise at least one internal L-2'-O-methyl ribopyrimidine subunit, a 3'-terminal L-2'-deoxycytidine subunit, and/or an arabino-adenosine branch point (Carriero and Damha, Nucleic Acids Research 31: 6157-6167, 2003). In various embodiments, the an inhibitor of lariat formation can comprise a nucleobase polymer comprising a sequence of at least about 10 contiguous nucleobases of a sequence of a lariat branch point of the RNA virus nucleic acid replicative form or the complement thereof, such as, for example, the sequence SEQ ID NO: 2; a nucleobase polymer comprising a sequence of at least about 10 contiguous nucleobases of a sequence 5' to a lariat branch point of the RNA virus nucleic acid replicative form or the complement thereof, such as, for example, the sequence SEQ ID NO: 3, or a nucleobase polymer comprising a sequence of at least about 10 nucleobases of a sequence 3' to a lariat branch point of the RNA virus nucleic acid replicative form or the complement thereof, such as, for example, the sequence SEQ ID NO: 4. In methods of the present invention, an inhibitor of lariat formation can be a molecule described in Carriero and Damha (supra). In some embodiments, these same sequences, or sequences sharing at least about 50%, sharing at least about 60%, sharing at least about 70%, sharing at least about 80% or sharing at least about 90% sequence similarity can inhibit lariat formation.

In certain configurations, an inhibitor of viral replication can comprise a nucleobase polymer. In some configurations, the nucleobase polymer can be an inhibitor of viral function such as lariat function. In these configurations, the nucleobase polymer can comprise one or more sequences sharing sequence identity with viral sequences expected to participate in lariat formation or function. The nucleobase polymer can be an RNA, a DNA, a hybrid molecule, or an unnatural polymer such as, for example, a peptide nucleic acid (PNA). The sequence can be in a sense or an antisense configuration. One or more subunits of a nucleobase polymer of the invention can comprise a non-ribose sugar such as an arabinose. Linkages between nucleobases can include, in addition to 5'-3' linkages, linkages such as 5'-2' linkages, and linkages to non-ribose sugars such as arabinose. In some configurations, an inhibitor can comprise one or more non-standard bases, such as, for example, L-2'-deoxycytidine or 2'-O-ribopyrimidine. Since the 5' end of the MNV-1 and other viral genomes contains consensus sequences for mammalian splicing machinery and since the same sequences are present at the 5' end of the subgenomic and predicted subgenomic RNAs of viruses, a lariat form of viral RNA can comprise a subgenomic lariat or a full (genomic) length.

The nucleobase polymer can comprise, for example, a sequence found in a norovirus or a norovirus replicative form, such as GTGAAATGA (SEQ ID NO: 2), GTGAAATGAGG (SEQ ID NO: 3), TACCGATCT (SEQ ID NO: 4), CTAC-CGATCTCGGG (SEQ ID NO: 5), GTGAAATGAGGTAC-CGAT (SEQ ID NO: 6) or a complement thereof. In some configurations, an inhibitor of lariat function can comprise a nucleobase polymer which is topologically a Y-shaped nucleobase polymer or a lariat-shaped nucleobase polymer. In various configurations, the nucleobase polymer can be an RNA or a DNA, and comprise at least one internal L-2'-O-methyl ribopyrimidine subunit, a 3'-terminal L-2'-deoxycytidine subunit, and/or an arabino-adenosine branch point (Carriero and Damha, *Nucleic Acids Research* 31: 6157-6167, 2003). In various embodiments, the an inhibitor of lariat function can comprise a nucleobase polymer comprising a sequence of at least about 10 contiguous nucleobases of a sequence of a lariat branch point of the RNA virus nucleic acid replicative form or the complement thereof, such as, for example, the sequence SEQ ID NO: 2; a nucleobase polymer comprising a sequence of at least about 10 contiguous nucleobases of a sequence 5' to a lariat branch point of the RNA virus nucleic acid replicative form or the complement thereof, such as, for example, the sequence SEQ ID NO: 3, or a nucleobase polymer comprising a sequence of at least about 10 nucleobases of a sequence 3' to a lariat branch point of the RNA virus nucleic acid replicative form or the complement thereof, such as, for example, the sequence SEQ ID NO: 4. In methods of the present invention, an inhibitor of lariat function can be a molecule described in Carriero and Damha (supra). In some embodiments, these same sequences, or sequences sharing at least about 50%, sharing at least about 60%, sharing at least about 70%, sharing at least about 80% or sharing at least about 90% sequence similarity can inhibit lariat function.

In certain configurations, an inhibitor of viral replication can comprise an antibody. For example, a virus inhibitor can be an antibody directed against a structure comprising a nucleotide having 2'- and 3'-linkages. The antibody can be, for example, an antibody directed against a thymine nucleotide having 2'- and 3'-linkages.

In various embodiments, the RNA virus that forms a lariat structure upon infection of a permissive cell can be a single-stranded RNA virus; a positive strand single-stranded RNA virus; a positive strand single-stranded RNA virus, no DNA stage; a calicivirus; or a norovirus such as a human norovirus (i.e., a Norwalk virus) or a murine norovirus such as MNV-1 (Karst, S. M. et al., *Science* 299: 1575-1578, 2003).

In some embodiments, the invention provides a method of translating a nucleic acid encoding a polypeptide. In these embodiments, the method can comprise inoculating an RNA virus-permissive cell with a viral nucleic acid which forms a lariat structure operatively linked to a sequence encoding a polypeptide; and incubating the cell. The cell can be an RNA virus-permissive cell, such as a norovirus-permissive cell described supra. In some configurations, a cell in which a lariat can form upon introduction of lariat-forming sequences of can be a eukaryotic cell, such as, for example, an animal cell, a plant cell, or a cell of a eukaryotic microorganism such as a yeast. In non-limiting example, the virus can be a norovirus, and the cell can be a macrophage-lineage cell or a dendritic cell-lineage cell, such as a STAT-1 deficient macrophage, a macrophage-like cell of an established cell line such as a RAW cell, or a dendritic cell. In these methods, the RNA virus translation initiation sequence can comprise a lariat branch point sequence, or a sequence in which the 3' end is located up to about 10 nucleotides upstream or downstream from the branch point sequence, up to about 20 nucleotides upstream or downstream from the branch point sequence, up to about 50 nucleotides upstream or downstream from the branch point sequence, up to about 100 nucleotides upstream or downstream from the branch point sequence, or up to about 200 nucleotides upstream or downstream from the branch point sequence. The RNA virus translation sequence can comprise from at least about 10 nucleotides up to about 200 contiguous nucleotide, from at least about 15 nucleotides up to up to about 150 contiguous nucleotides, or from at least about 20 nucleotides up to up to about 100 contiguous nucleotides. T In some configurations, a lariat branch point sequence can comprise, for example, the sequence CTACCGATCTGTGAAATGAG (SEQ ID NO: 34). Alternatively, the RNA virus translation initiation sequence can be an RNA virus ribosome binding site, such as, for example, an RNA virus internal ribosome entry site (IRES). In some configurations, the RNA virus translation initiation sequence can comprise the sequence ATGAAGATGGC (SEQ ID NO: 35). In some configurations, the presence of an IRES or IRES-like activity implies that a norovirus or a vector comprising a norovirus lariat, a norovirus subgenomic RNA can be used to express heterologous genes in cells other than norovirus-permissive cells or RNA virus-permissive cells.

In various embodiments, an RNA virus-permissive cell can be a single stranded RNA virus-permissive cell, a positive strand single stranded RNA virus-permissive cell, a positive strand single stranded RNA virus, no DNA stage-permissive cell, a calicivirus-permissive cell, or a norovirus-permissive cell. For example, a norovirus-permissive cell can be a macrophage-lineage cell or a dendritic cell-lineage cell.

In various configurations, the RNA virus translation initiation sequence can be a single-stranded RNA virus translation initiation sequence, a positive strand single-stranded RNA virus translation initiation sequence, a positive strand single-stranded RNA virus, no DNA stage translation initiation sequence, a calicivirus translation initiation sequence, or a norovirus translation initiation sequence. In certain configurations, the translation initiation sequence can have at least about 80% sequence identity with SEQ ID NO: 35. In certain configurations, the translation initiation sequence can have the sequence designated SEQ ID NO: 35.

In various configurations, the nucleic acid can be an RNA or a DNA.

Various aspects of the present teachings accordingly include:

Aspect 1. A method of inhibiting RNA virus replication, the method comprising contacting an RNA virus-infected cell with an inhibitor of lariat formation, wherein the RNA virus nucleic acid comprises a replicative form comprising at least one 5'-2' phosphodiester bond.

Aspect 2. The method of aspect 1, wherein the inhibitor of lariat formation comprises a nucleobase polymer.

Aspect 3. The method of aspect 2, wherein the nucleobase polymer comprises a sequence selected from the group consisting of GTGAAATGA (SEQ ID NO: 36), GTGAAATGAGG (SEQ ID NO: 37), TACCGATCT (SEQ ID NO: 38), CTACCGATCTCGGG (SEQ ID NO: 39), GTGAAATGAGGTACCGAT (SEQ ID NO: 40) and a complement thereof.

Aspect 4. The method of aspect 2, wherein the nucleobase polymer is a Y-shaped nucleobase polymer.

Aspect 5. The method of aspect 4, wherein the nucleobase polymer comprises at least one internal L-2'-O-methyl ribopyrimidine subunit.

Aspect 6. The method of aspect 4, wherein the nucleobase polymer comprises a 3'-terminal L-2'-deoxycytidine subunit.

Aspect 7. The method of aspect 4, wherein the nucleobase polymer comprises an arabino-adenosine branch point.

Aspect 8. The method of aspect 1, wherein the RNA virus nucleic acid replicative form comprising at least one 5'-2' phosphodiester bond further comprises a lariat.

Aspect 9. The method of aspect 1, wherein the inhibitor comprises a nucleobase polymer comprising a sequence of at least about 10 contiguous nucleobases of a lariat branch point of the RNA virus nucleic acid replicative form or the complement thereof.

Aspect 10. The method of aspect 9, wherein the nucleobase polymer comprises the sequence SEQ ID NO: 1.

Aspect 11. The method of aspect 1, wherein the inhibitor comprises a nucleobase polymer comprising a sequence of at least about 10 contiguous nucleobases of a sequence 5' to a lariat branch point of the RNA virus nucleic acid replicative form or the complement thereof.

Aspect 12. The method of aspect 11, wherein the nucleobase polymer comprises the sequence SEQ ID NO: 2.

Aspect 13. The method of aspect 1, wherein the inhibitor comprises a nucleobase polymer comprising a sequence of at least about 10 nucleobases of a sequence 3' to a lariat branch point of the RNA virus nucleic acid replicative form or the complement thereof.

Aspect 14. The method of aspect 13, wherein the nucleobase polymer comprises the sequence SEQ ID NO: 3.

Aspect 15. The method of aspect 1, wherein the RNA virus is a single-stranded RNA virus.

Aspect 16. The method of aspect 15, wherein the single-stranded RNA virus is a positive strand single-stranded RNA virus.

Aspect 17. The method of aspect 16, wherein the positive strand single-stranded RNA virus is a positive strand single stranded RNA virus, no DNA stage.

Aspect 18. The method of aspect 17, wherein the positive strand single-stranded RNA virus, no DNA stage is a calicivirus.

Aspect 19. The method of aspect 17, wherein the calicivirus is a norovirus.

Aspect 20. The method of aspect 19, wherein the norovirus is selected from the group consisting of a human norovirus and a murine norovirus.

Aspect 21. A method of translating a nucleic acid encoding a polypeptide, the method comprising:
 inoculating an RNA virus-permissive cell with a viral nucleic acid which forms a lariat structure operatively linked to a sequence encoding the polypeptide; and
 incubating the cell.

Aspect 22. The method of aspect 21, wherein the RNA virus translation initiation sequence comprises a lariat branch point sequence.

Aspect 23. The method of aspect 21, wherein the RNA virus translation initiation sequence is an RNA virus ribosome binding site.

Aspect 24. The method of aspect 23, wherein the RNA virus ribosome binding site is an RNA virus internal ribosome entry site.

Aspect 25. The method of aspect 21, wherein the RNA virus translation initiation sequence is comprised by a sequence is selected from the group consisting of SEQ ID NO: 28, SEQ ID NO: 29, SEQ ID NO: 30, SEQ ID NO: 31, SEQ ID NO: 32, and SEQ ID NO: 33.

Aspect 26. The method of aspect 21, wherein the RNA virus-permissive cell is a single stranded RNA virus-permissive cell.

Aspect 27. The method of aspect 26, wherein the single stranded RNA virus-permissive cell is a single stranded RNA virus, no DNA stage-permissive cell.

Aspect 28. The method of aspect 27, wherein the single stranded RNA virus, no DNA stage-permissive cell is a calicivirus-permissive cell.

Aspect 29. The method of aspect 28, wherein the calicivirus-permissive cell is a norovirus-permissive cell.

Aspect 30. The method of aspect 29, wherein the norovirus permissive cell is selected from the group consisting of a macrophage-lineage cell and a dendritic cell-lineage cell.

Aspect 31. The method of aspect 21, wherein the RNA virus translation initiation sequence is a single-stranded RNA virus translation initiation sequence.

Aspect 32. The method of aspect 31, wherein the single-stranded RNA virus translation initiation sequence is a single-stranded RNA virus, no DNA stage translation initiation sequence.

Aspect 33. The method of aspect 32, wherein the single-stranded RNA virus, no DNA stage translation initiation sequence is a calicivirus translation initiation sequence.

Aspect 34. The method of aspect 33, wherein the calicivirus translation initiation sequence is a norovirus translation initiation sequence.

Aspect 35. The method of aspect 21, wherein the translation initiation sequence has at least about 80% sequence identity with SEQ ID NO: 10.

Aspect 36. The method of aspect 21, wherein the translation initiation sequence is SEQ ID NO: 11.

Aspect 37. The method of aspect 21, wherein the nucleic acid is an RNA.

Aspect 38. The method of aspect 21, wherein the nucleic acid is a DNA.

Aspect 39. A replicon comprising an RNA virus translation initiation site, an RNA virus branch point and a sequence encoding a heterologous polypeptide.

Aspect 40. A replicon comprising an RNA virus branch point and a sequence encoding a heterologous polypeptide.

Aspect 41. The replicon of aspect 40, further comprising an RNA virus promoter.

Aspect 42. The replicon of aspect 40, wherein the RNA virus branch point is a single-stranded RNA virus branch point.

Aspect 43. The replicon of aspect 42, wherein the single-stranded RNA virus branch point is a single-stranded RNA virus no DNA stage branch point.

Aspect 44. The replicon of aspect 43, wherein the single-stranded RNA virus no DNA stage branch point is a calicivirus branch point.

Aspect 45. The replicon of aspect 44, wherein the calicivirus branch point is a norovirus branch point.

Aspect 46. The replicon of aspect 45, wherein the norovirus branch point is an MNV-1 branch point.

Aspect 47. The replicon of aspect 40 wherein the RNA virus branch point comprises a sequence comprising at least 20 nucleotides and hybridizes under high stringency conditions to a complement of a sequence selected from the group consisting of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO:20, SEQ ID NO:21, SEQ ID NO:22, SEQ ID NO:23, SEQ ID NO:24, SEQ ID NO:25, SEQ ID NO:26 and SEQ ID NO:27.

Aspect 48. The replicon of aspect 40, wherein the RNA virus branch point comprises a sequence comprising at least 20 contiguous nucleotides having at least about 70% sequence identity with a sequence selected from the group consisting of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO:20, SEQ ID NO:21, SEQ ID NO:22, SEQ ID NO:23, SEQ ID NO:24, SEQ ID NO:25, SEQ ID NO:26, SEQ ID NO:27 and portions thereof.

Aspect 49. A method for transcribing an RNA sequence, the method comprising:
 inoculating a eukaryotic cell with a replicon comprising an RNA virus branch point and the sequence; and
 growing the cell.

Aspect 50. The method of aspect 49, wherein the RNA virus branch point comprises a sequence comprising at least 20 contiguous nucleotides having at least about 70% sequence identity with a sequence selected from the group consisting of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27 and portions thereof.

Aspect 51. The method of aspect 49, wherein the RNA virus branch point is a norovirus branch point.

Aspect 52. The method of aspect 49, wherein the eukaryotic cell is an animal cell.

Aspect 53. The method of aspect 52, wherein the animal cell is a vertebrate cell.

Aspect 54. The method of aspect 53, wherein the vertebrate cell is a mammalian cell.

Aspect 55. The method of aspect 54, wherein the mammalian cell is selected from the group consisting of a human cell and a murine cell.

Aspect 56. The method of aspect 54, wherein the mammalian cell is a norovirus-permissive cell.

Aspect 57. A method for synthesizing a polypeptide, the method comprising:

inoculating a eukaryotic cell with a nucleic acid comprising an RNA lariat-forming sequence of an RNA virus linked to a sequence encoding the polypeptide, wherein the polypeptide is heterologous to the virus; and incubating the cell.

Aspect 58. The method of aspect 57, wherein the nucleic acid further comprises an RNA virus promoter.

Aspect 59. The method of aspect 57, wherein the nucleic acid further comprises an RNA virus translation initiation sequence.

Aspect 60. The method of aspect 57, wherein the nucleic acid further comprising an RNA virus internal ribosome entry site.

Aspect 61. The method of aspect 57, wherein the RNA virus branch point is a single-stranded RNA virus branch point.

Aspect 62. The method of aspect 61, wherein the single-stranded RNA virus branch point is a single-stranded RNA virus no DNA stage branch point.

Aspect 63. The method of aspect 62, wherein the single-stranded RNA virus no DNA stage branch point is a calicivirus branch point.

Aspect 64. The method of aspect 63, wherein the calicivirus branch point is a norovirus branch point.

Aspect 65. The method of aspect 64, wherein the norovirus branch point is an MNV-1 branch point.

Aspect 66. The method of aspect 57, wherein the RNA virus branch point comprises a sequence comprising at least 20 nucleotides and hybridizes under high stringency conditions to a complement of a sequence selected from the group consisting of SEQ ID NO: 28, SEQ ID NO: 29, SEQ ID NO: 30, SEQ ID NO: 31, SEQ ID NO: 32, SEQ ID NO: 33.

Aspect 67. The method of aspect 57, wherein the RNA virus branch point comprises a sequence comprising at least 20 contiguous nucleotides having at least about 70% sequence identity with a sequence selected from the group consisting of SEQ ID NO: 28, SEQ ID NO: 29, SEQ ID NO: 30, SEQ ID NO: 31, SEQ ID NO: 32, SEQ ID NO: 33 and portions thereof.

Aspect 68. A method for forming an attenuated RNA virus, the method comprising altering lariat involved cis acting sequences.

Aspect 69. A method for altering host cell splicing by expressing a viral RNA sequence.

Aspect 70. The method of aspect 69, wherein the viral RNA sequence is a single-stranded RNA virus viral RNA sequence.

Aspect 71. The method of aspect 70, wherein the single-stranded RNA virus is a single-stranded RNA, no DNA stage virus.

Aspect 72. The method of aspect 71, wherein the single-stranded RNA, no DNA stage virus is a calicivirus.

Aspect 73. The method of aspect 72, wherein the calicivirus is a norovirus.

Aspect 74. The method of aspect 73, wherein the norovirus is a human norovirus or a murine norovirus.

Aspect 75. A method for forming an attenuated RNA virus, the method comprising altering an RNA virus viral polypeptide that utilizes a thymine as a viral lariat-forming donor nucleotide.

Aspect 76. The method of aspect 75, wherein the RNA virus is a single-stranded RNA virus.

Aspect 77. The method of aspect 76, wherein the single-stranded RNA virus is a single-stranded RNA, no DNA stage virus.

Aspect 78. The method of aspect 77, wherein the single-stranded RNA, no DNA stage virus is a calicivirus.

Aspect 79. The method of aspect 78, wherein the calicivirus is a norovirus. Aspect 80. The method of aspect 79, wherein the norovirus is a human norovirus or a murine norovirus.

Aspect 81. A method for identifying an antiviral molecule, the method comprising:

contacting a cell comprising an RNA comprising a lariat-forming sequence of an RNA virus with a candidate antiviral molecule; and detecting inhibition of lariat formation, function, or stability in the cell.

Aspect 82. A method of expressing a polypeptide in a cell, the method comprising:

introducing into the cell a nucleic acid comprising a genomic sequence encoding the polypeptide and further comprising at least one intron comprising a branch point sequence comprising a uridine nucleotide; and expressing at least one viral polypeptide which regulates intron processing in the cell.

Aspect 83. The method of aspect 82, wherein the at least one viral polypeptide which regulates intron processing in the cell is a viral polypeptide which causes the uridine nucleotide to be a 2' hydroxyl nucleophilic nucleotide in an RNA splicing reaction.

Aspect 84. The method of aspect 82, wherein the expressing at least one viral polypeptide comprises inoculating the cell with an RNA virus.

Aspect 85. The method of aspect 84, wherein the at least one viral polypeptide is a viral polypeptide of an RNA virus.

Aspect 86. The method of aspect 85, wherein the RNA virus is a single-stranded RNA virus.

Aspect 87. The method of aspect 86, wherein the single-stranded RNA virus is a single-stranded RNA virus, no DNA stage.

Aspect 88. The method of aspect 87, wherein the single-stranded RNA virus is a single-stranded RNA virus, no DNA stage is a calicivirus.

Aspect 89. The method of aspect 88, wherein the calicivirus is a norovirus.

Aspect 90. The method of aspect 89, wherein the norovirus is selected from a human norovirus and a murine norovirus.

Aspect 91. The method of aspect 83, wherein the branch point sequence comprising a nucleophilic 2' hydroxyl uridine residue comprises the sequence UACCGAUCU.

Aspect 92. A method of inhibiting expression of a polypeptide in a eukaryotic cell, the method comprising expressing in the eukaryotic cell at least one viral polypeptide of an RNA virus, wherein the at least one viral polypeptide alters host cell RNA splicing.

Aspect 93. The method of aspect 92, wherein the at least one viral polypeptide is a viral polypeptide which causes an intronic uridine nucleotide to act as a nucleophile in an RNA splicing reaction.

Aspect 94. The method of aspect 93, wherein the expressing at least one viral polypeptide comprises inoculating the cell with an RNA virus.

Aspect 95. The method of aspect 94, wherein the at least one viral polypeptide is a viral polypeptide of an RNA virus.

Aspect 96. The method of aspect 95, wherein the RNA virus is a single-stranded RNA virus.

Aspect 97. The method of aspect 96, wherein the single-stranded RNA virus is a single-stranded RNA virus, no DNA stage.

Aspect 98. The method of aspect 97, wherein the single-stranded RNA virus is a single-stranded RNA virus, no DNA stage is a calicivirus.

Aspect 99. The method of aspect 98, wherein the calicivirus is a norovirus.

Aspect 100. The method of aspect 99, wherein the norovirus is selected from a human norovirus and a murine norovirus.

Aspect 101. The method of aspect 92, the RNA virus comprises a branch point sequence comprising a nucleophilic 2' hydroxyl group uridine residue.

Aspect 102. The method of aspect 101, wherein the branch point sequence comprises the sequence UACCGAUCU.

The invention can be further understood by reference to the examples which follow.

Example 1

This example illustrates methods for growth and harvesting of cells and cell lines used for investigating norovirus growth in vitro.

In this example, murine embryo fibroblasts were obtained and cultured as described in Pollock et al., Virology 227: 168-179, 1997, or according to instructions provided by the supplier. RAW 264.7 cells were purchased from the American Type Culture Collection and maintained in Dulbecco's Modified Eagle's Medium (DMEM) supplemented with 10% low-endotoxin fetal calf serum (FCS, HyClone, Logan, Utah, cat #SH30070.03), 100 U penicillin/ml, 100 µg/ml streptomycin, 10 mM N-2-hydroxyethylpiperazine-N'-2-ethanesulfonic acid (HEPES), and 2 mM L-glutamine (Biosource, Camarillo, Calif.). Macrophages were harvested from bone marrow and cultured as described in Heise et al., Virology 241: 331-344, 1998. Dendritic cells were obtained by suspending bone marrow cells in RPMI 1640 medium containing 10% low endotoxin FCS, 2 mM L-glutamine, 1 mM sodium pyruvate (Biosource), 100 U penicillin/ml, 100 µg/ml streptomycin, 1% non-essential amino acids (Biosource) and 20 ng/ml recombinant mouse GM-CSF (BD Biosciences, San Jose, Calif.), and plating the cells at a concentration of $3 \times 10^5$ cells/ml in 6 well plates (3 ml/well). The percentage of CD11c$^+$ dendritic cells was determined by FACS analysis after culturing cells for seven days at 37° C. and 5% $CO_2$. Around 70% of the cells were CD11c-positive. 129 wild-type and STAT 1–/– mice were purchased from Taconic (Germantown, N.Y.). Interferon (IFN) αβ receptor (R)–/– mice, IFNγR–/– mice, and IFN αβγR–/– mice (Muller et al., Science 264, 1918-1921, 1994), protein kinase R–/– mice (Yang et al., EMBO J. 14, 6095-6106, 1995), and inducible nitric oxide (iNOS)–/– mice (MacMicking et al., Cell 81, 641-650, 1995) were bred and housed at Washington University in accordance with all federal and university policies.

Example 2

This example illustrates methods for infection of cells with norovirus.

In this example, as shown in FIG. 1, Panel A, adherent cells were plated in 12 well plates at $2 \times 10^5$ or $5 \times 10^5$ cells per well and allowed to attach for several hours. Infections were carried out at an M.O.I. of 0.05 (for multi-step growth curves, FIG. 1) or M.O.I. of 2.0 (for single-step growth curves and other timecourse experiments, FIG. 3) for 30 min on ice in a volume of 0.5 ml per well. dendritic cells were infected in bulk. Cells were then washed extensively with 2×2 ml of ice-cold PBS per well. To allow viral entry, 1 ml of media was added to each well and cells were incubated at 37° C. and 5% $CO_2$ for different time periods. Growth curve samples were subjected to two or three cycles of freeze/thawing before titering. These data show that MNV-1 replicates in macrophages, dendritic cell's, and RAW cells.

Example 3

This example illustrates a mouse norovirus-1 plaque assay.

In this example, as illustrated in FIG. 1, Panels A and B, RAW 264.7 cells were seeded into 6 well plates at a density of $2 \times 10^6$ viable cells. On the following day, 10-fold dilutions of virus inoculum were prepared in complete DMEM and plated in duplicate wells. Plates were incubated for one hour at room temperature on a rocking apparatus before aspirating the inoculum and overlaying the cells with 2 ml of 37-40° C. 1.5% SeaPlaque® agarose (CBM Intellectual Properties, Inc.) in MEM supplemented with 10% low-endotoxin FCS, 1% HEPES, 1% penicillin/streptomycin, and 2% glutamine (complete MEM). Plates were incubated at 37° C. and 5% $CO_2$ for 2 days. To visualize plaques, cells were stained with 2 ml of 56° C. 1.5% SeaKem® agarose (FMC Corporation) in complete MEM containing 1% Neutral Red for 6-8 hours. These data show that MNV-1 replication can be quantified using a plaque assay.

Example 4

This example illustrates a mouse norovirus-1 plaque neutralization assay method.

Figure 2:
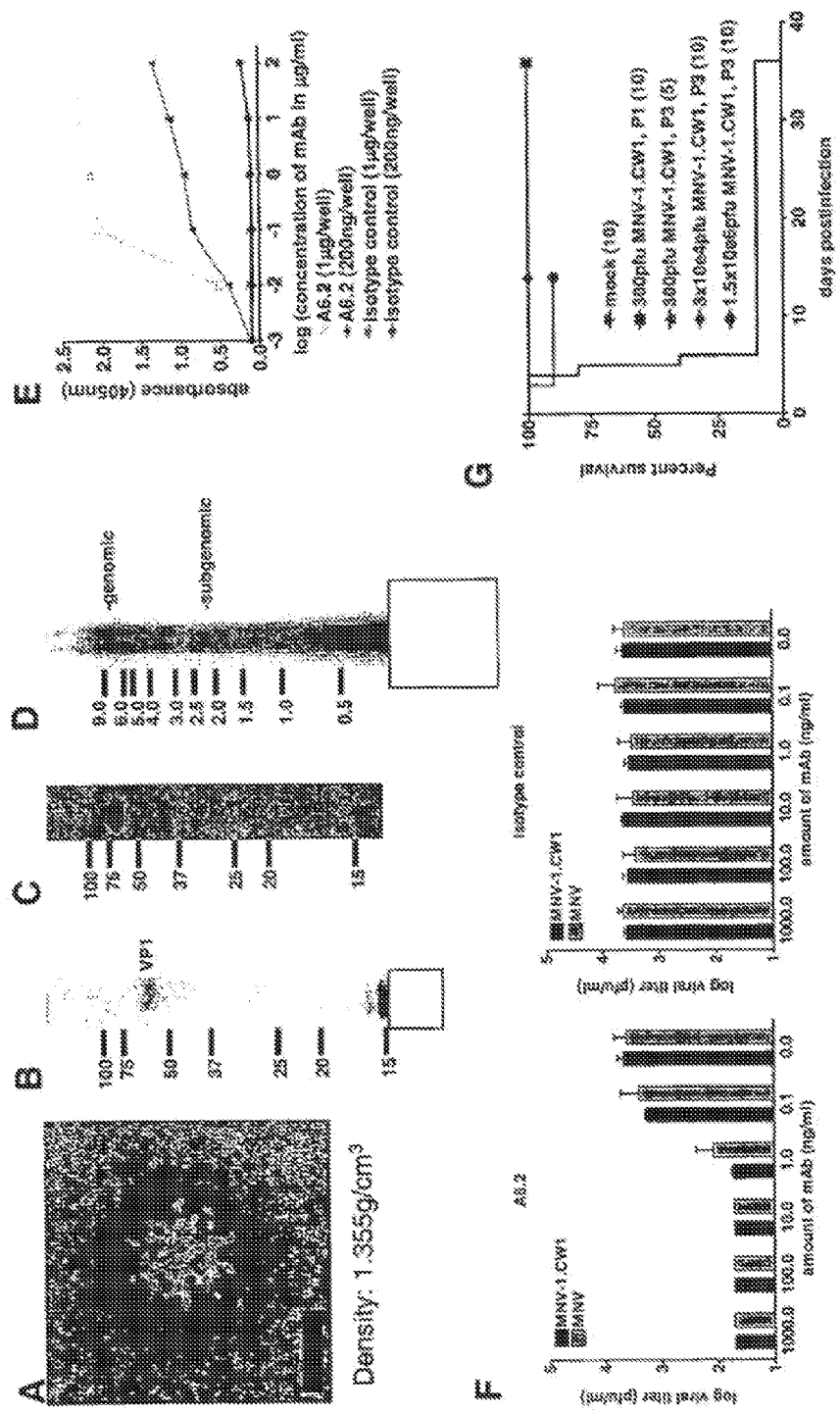
FIG. 2 illustrates virus grown from plaques from the culture system infected with MNV-1.

In this example, as shown in FIG. 2, Panels E and F, differing concentrations of purified monoclonal antibody (A6.2=anti-MNV-1 capsid, isotype control=10H2, anti-µ1c reovirus) were incubated with 2000 pfu of either MNV-1.CW1 or MNV-1 brain homogenate for 30 min at 37° C. prior to performing the MNV-1 plaque assay as described in Example 3. These data show that the plaques are due to MNV-1 and that an antibody can block infection with MNV-1.

Example 5

This example illustrates methods for Cesium Chloride purification of mouse norovirus-1.

In this example, as shown in FIG. 2, Panels A, B, C and D, RAW cells were infected with MNV-1.CW1 for 2 days with an MOI=0.05. Cellular debris was removed from the freeze/thaw lysate by low speed centrifugation. The supernatants were layered on top of a 5 ml 30% sucrose cushion and centrifuged at 4° C. for 2.5 hours at 27,000 rpm (90,000×g) in a SW32 rotor. The cell pellets were then resuspended in PBS and mixed with CsCl to a final density of 1.33 g/cm$^3$ and centrifuged for at least 18 hours at 35,000 rpm (115,000×g) in a SW55 rotor. A wide lower and narrow upper band were typically seen in the gradient. The lower band was collected by puncturing the side of the tube with a needle before overnight dialysis against PBS at 4° C. These data show that the virus growing is MNV-1 and is a norovirus.

Example 6

This example illustrates methods for protein analysis using SDS-polyacrylamide gel electrophoresis and Coomassie blue staining.

In this example, as illustrated in FIG. 2, Panel B, CsCl-purified virions were separated by SDS-PAGE using standard procedures (Laemmli, U.K., Nature, 227: 680-685, 1970). Proteins were visualized by Coomassie staining using the Simply Blue™ safe stain (Invitrogen, Carlsbad, Calif.) according to manufacturer's instructions. These data, together with data shown in FIG. 2, Panel C, show that the virus growing in the cells contains the MNV-1 capsid protein.

Example 7

This example demonstrates Western blot analysis methods.

In this example, as shown in FIG. 2, Panel C, proteins were transferred to a nitrocellulose membrane and incubated with a rabbit polyclonal antibody directed against MNV-1 capsid protein, followed by a peroxidase-labeled secondary antibody. Antibody binding was visualized using ECL™ chemiluminescence (Amersham Biosciences, Piscataway, N.J.) according to the manufacturer's instructions. The data show that the capsid in the growing virus is the MNV-1 capsid protein.

Example 8

This example illustrates Northern blot analysis methods.

In this example, as shown in FIG. 2, Panel D, probes for Northern blot analysis were generated by linearizing and gel purifying plasmid DNA containing portions of the MNV-1 genome (nt 5617-7039) digested with restriction endonuclease NcoI (for a positive-sense probe) or restriction endonuclease SpeI (for a negative-sense probe). Labeled probes were generated by performing a standard $P^{32}$ radioactive transcription assay using SP6 or T7 RNA polymerase (Roche, Germany) according to manufacturer's recommendations. Total RNA from virus-infected or mock-infected cells were isolated using Trizol (Invitrogen, Carlsbad, Calif.) according to manufacturer's recommendations. Northern blotting was performed using standard protocols. Probes were hybridized overnight at 68° C. The data show that the RNA in the growing virus is MNV-1 RNA.

Example 9

This example illustrates ELISA analysis methods.

In this example, as illustrated in FIG. 2, Panel E, ELISA was performed as described in Karst, S. M. et al., Science 299: 1575-1578, 2003, with the following modifications. ELISA plates were coated overnight at 4° C. with CsCl-purified MNV-1 particles at 0.2 or 1.0 mg/well. Diluted, purified anti-MNV-1 capsid monoclonal antibody A6.2 and anti-reovirus isotype control monoclonal antibody 10H2 were applied to coated wells, followed by a peroxidase-labeled secondary antibody. Antibodies were incubated in wells for 60 min. at 37° C. These data show that the A6.2 monoclonal antibody binds specifically to MNV-1.

Example 10

This example illustrates electron microscopy methods used to image mouse MNV-1.

In this example, as shown in FIG. 2, Panel A, samples of CsCl-purified MNV-1 virions were negatively stained and observed using an electron microscope, as described in Karst et al., supra. The morphology of the observed particles is consistent with that of a virus. The data show that the growing virus is a norovirus.

Example 11

This example illustrates lytic growth of a norovirus, MNV-1 (Karst, S. M. et al., Science 299: 1575-1578, 2003; U.S. Patent Application 60/440,016 of Virgin, "Murine Calicivirus" filed Jan. 14, 2003), in murine macrophage-lineage cells.

In this example, as shown in FIG. 3, macrophage-lineage cells, including primary murine STAT1−/− bone marrow derived macrophages and the murine macrophage cell lines RAW 264.7 and J774A.1, were infected with mouse norovirus MNV-1. As shown in FIG. 3, Panel A, each of these macrophage-lineage cell types supported viral replication and lytic growth. Using RAW 264.7 cells, a MNV-1 plaque assay was developed and used to study the viral life cycle (FIGS. 1A, 1B). While a cytopathic effect was visible in productively infected cells 24 hours postinfection (h.p.i.), virions were detected between 9 and 12 h.p.i. Virion production was preceded by the production of genomic and subgenomic RNAs as detected by Northern blot analysis (FIG. 3, Panel B). Growth in RAW cells for a single passage did not dramatically alter the virulence of MNV-1, as a plaque purified strain (MNV-1.CW) still caused lethal disease in STAT−/− mice after peroral inoculation (FIG. 2, Panel G MNV-1.CW1 passage 1). However, growth in RAW cells for three passages generated a virus stock with significantly decreased virulence towards STAT−/− mice (FIG. 2, Panel G, MNV-1.CW1 passage 3). This example demonstrates that MNV-1 can be cultured in macrophage-lineage cells, that macrophage-lineage cells can be norovirus-permissive cells, and that MNV-1 can lose its virulence upon serial passage in norovirus-permissive cells. Furthermore, this example shows that replication of viral RNA can be detected by Northern Blot analysis.

Example 12

This example illustrates that MNV-1 productively infects STAT-deficient macrophages, RAW 264.7 cells and dendritic cells, and causes cytopathic effects in these cells.

In this example, as shown in FIG. 1, wild-type murine embryonic fibroblasts, STAT−/− embryonic fibroblasts, wild-type primary mouse macrophages, STAT−/− macrophages, wild-type dendritic cells, STAT−/− dendritic cells, and RAW 264.7 cells were examined for their permissiveness towards norovirus infection. In these experiments, the cells were initially obtained and grown under conditions described in Example 1, and contacted for 30 minutes on ice with an MNV-1-containing brain homogenate at a multiplicity of infection (M.O.I.) of 0.05. (A) Cells were subjected to freezing and thawing at various time intervals following contact with the MNV-1 brain homogenate. Virus production was the measured by titering using the plaque assay as described in Example 3. Each time point was repeated 2-3 times to generate standard errors of the mean. The data indicate that STAT−/− macrophages support significantly more virus production than wild type macrophages, while wild type dendritic cells, STAT−/− dendritic cell's, and RAW cells all support significant amounts of virus production. (B) MNV-1 causes cytopathic effect in permissive cells. Cells contacted with MNV-1-containing brain homogenate as above, or mock infected with an uninfected brain homogenate, were cultured for two days and observed by light microscopy. Cytopathic effects of MNV-1 infection are evident in STAT-1−/− macrophage cultures, dendritic cell cultures (both wild type and STAT−/−), and RAW cell cultures, but not in mouse embryonic fibroblast cultures (either wild type or STAT−/−) nor wild type macrophage cultures.

Example 13

This example illustrates that virus grown from plaques from norovirus-permissive cell cultures infected with MNV-1 is MNV-1.

In these experiments, MNV-1 was plaque purified three times in RAW 264.7 cells. The resulting virus strain was designated MNV-1.CW1. The MNV-1.CW1 was purified by CsCl buoyant density gradient centrifugation, then analyzed as shown in FIG. 2: (A) MNV-1.CW1 visualized by negative staining electron microscopy. CsCl gradient-purified MNV-1.CW1 particles show typical norovirus morphology. (B) SDS-polyacrylamide gel electrophoresis analysis of CsCl gradient-purified MNV-1.CW1 particles. A gel stained with Coomassie Brilliant Blue reveals that the virus particles comprise a large amount of a protein with the appropriate molecular weight for the MNV-1 capsid. (C) Western Blot analysis of CsCl gradient-purified MNV-1.CW1 particles. A polyacrylamide gel prepared similar to that shown in (B) was transferred to a membrane and probed with an antibody directed against recombinant MNV-1 capsid protein. The single prominent band corresponding to the protein band labeled "VP1" in (A) bound the antibody probe. Because of its reactivity with the antibody, the polypeptide comprising the band was deemed to be MNV-1 capsid protein. (D) Northern Blot analysis of RNA obtained from infected RAW 264.7 cells. Following separation according to size by gel electrophoresis, the RNA was transferred to a membrane and probed under high stringency conditions (Sambrook et al., supra) using a probe specific for the MNV-1 genome. The hybridization was much stronger for RNA from infected cells compared to uninfected control cells (data not shown). (E) ELISA analysis of CsCl gradient-purified MNV-1.CW1 particles. Virus particles were distributed to wells in an ELISA plate, and probed with monoclonal antibodies directed against either MNV-1 capsid protein (MAb A6.2) or a reovirus protein (MAb 10H2). Binding of the primary antibodies to the virus samples was detected using an enzyme-conjugated secondary antibody. The data indicate that MAb A6.2 specifically bound to the norovirus. (F) Plaque neutralization assay. Samples of MNV-1 brain homogenate or MNV-1.CW1 were incubated with increasing concentrations of MAb A6.2 or MAb 10H2 before performing a plaque assay. The data indicate that MAb A6.2 neutralizes the virus, while control, isotype-matched MAb 10H2 did not. Thus, a monoclonal antibody can be used as an anti-viral agent for inhibiting viral infection.

Example 14

This example illustrates that bone marrow-derived macrophages and RAW 264.7 cells, are permissive for growth of MNV-1.CW1 virus, and that passaging of the norovirus increases its host cell range.

Figure 3:
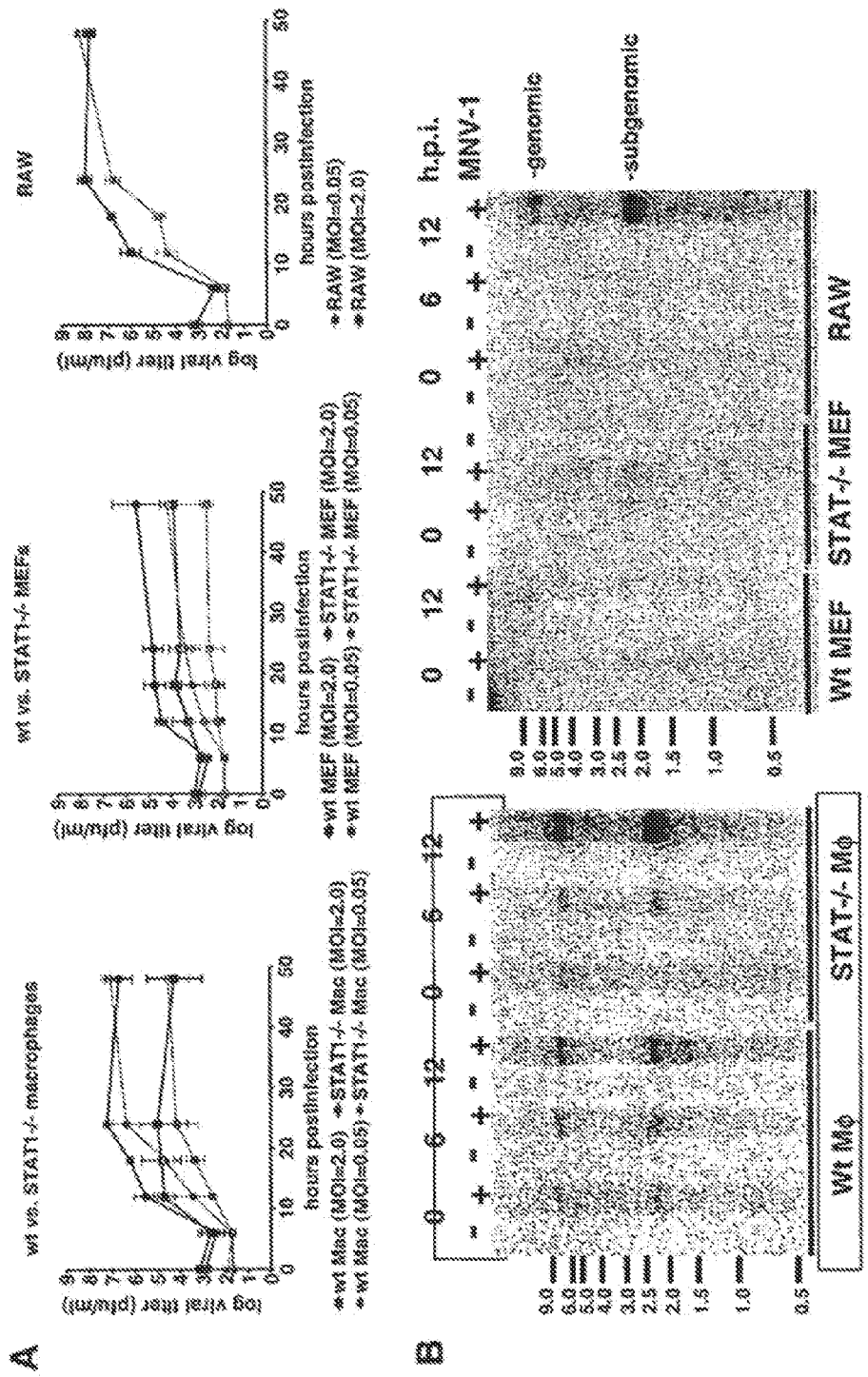
FIG. 3 illustrates growth of plaque-derived MNV-1.CW1 virus in bone marrow-derived macrophages, and RAW 264.7 cells.

In these experiments, MNV-1.CW1 virus, as described above, was expanded three times in RAW 264.7 cells, yielding MNV-1.CW1 P3 virus, as shown in FIG. 3. Multi-step (M.O.I. 0.05) and single-step (M.O.I. 2.0) growth curves were generated using MNV-1.CW1 P3 virus on indicated cells. While the thrice-passaged virus stock retained the capacity to grow to high titers in the RAW 264.7 cells, it showed an increase in host range, in that it replicated in STAT-1−/− embryonic fibroblasts. Nonetheless, some selective permissiveness of the virus for viral growth in macrophages over fibroblasts was still retained, as shown by the higher titers obtained in macrophages versus murine embryonic fibroblasts. FIG. 3, Panel B shows Northern blot analysis of timecourse of viral RNA infection from cells infected with MNV-1.CW 1 at an M.O.I. of 2.0, or mock-infected. h.p.i.=hours post infection. Analysis of the levels of viral RNA over time reveal that viral RNA synthesis was greater in macrophages than fibroblasts and greater in STAT-1−/− macrophages than in wild type macrophages. Together, these data indicate that noroviruses can adapt to grow in normally non-permissive cells in culture, while retaining sensitivity to STAT1-dependent antiviral effects.

Example 15

This example illustrates mechanisms of MNV-1 growth control.

Figure 4:
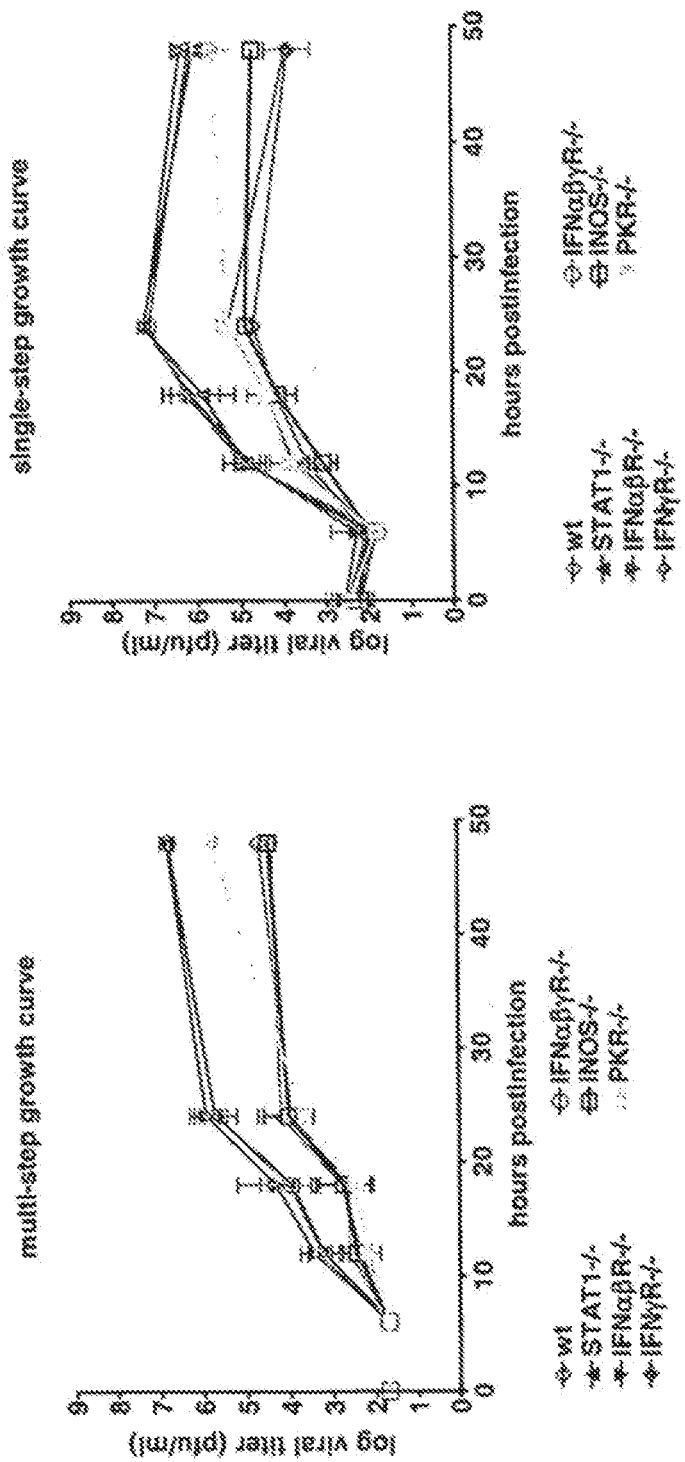
FIG. 4 illustrates mechanisms of plaque-derived MNV-1 growth control.

In these experiments, macrophages lacking specific components of the antiviral machinery were tested for their MNV-1 permissiveness. As shown in FIG. 4, MNV-1 growth in macrophages is controlled by STAT-1, type I interferon receptors and PKR. Multi-step (M.O.I.=0.05, left panel) and single-step (M.O.I.=2.0, right panel) growth curves of MNV.CW1 in bone marrow-derived murine macrophages are shown. Macrophages from mice lacking the interferon-αβ receptor, STAT-1, or PKR all showed increased permissiveness for MNV-1 growth, demonstrating that these three molecules are part of the cellular response that limits norovirus growth. In contrast, deletion of other antiviral molecules, including iNOS and RNaseL, had no effect on MNV-1 growth.

Example 16

This example illustrates that a Type I interferon response and STAT-1 are required to prevent MNV-1 replication in bone marrow macrophages in vitro, as measured by viral RNA production.

Figure 5:
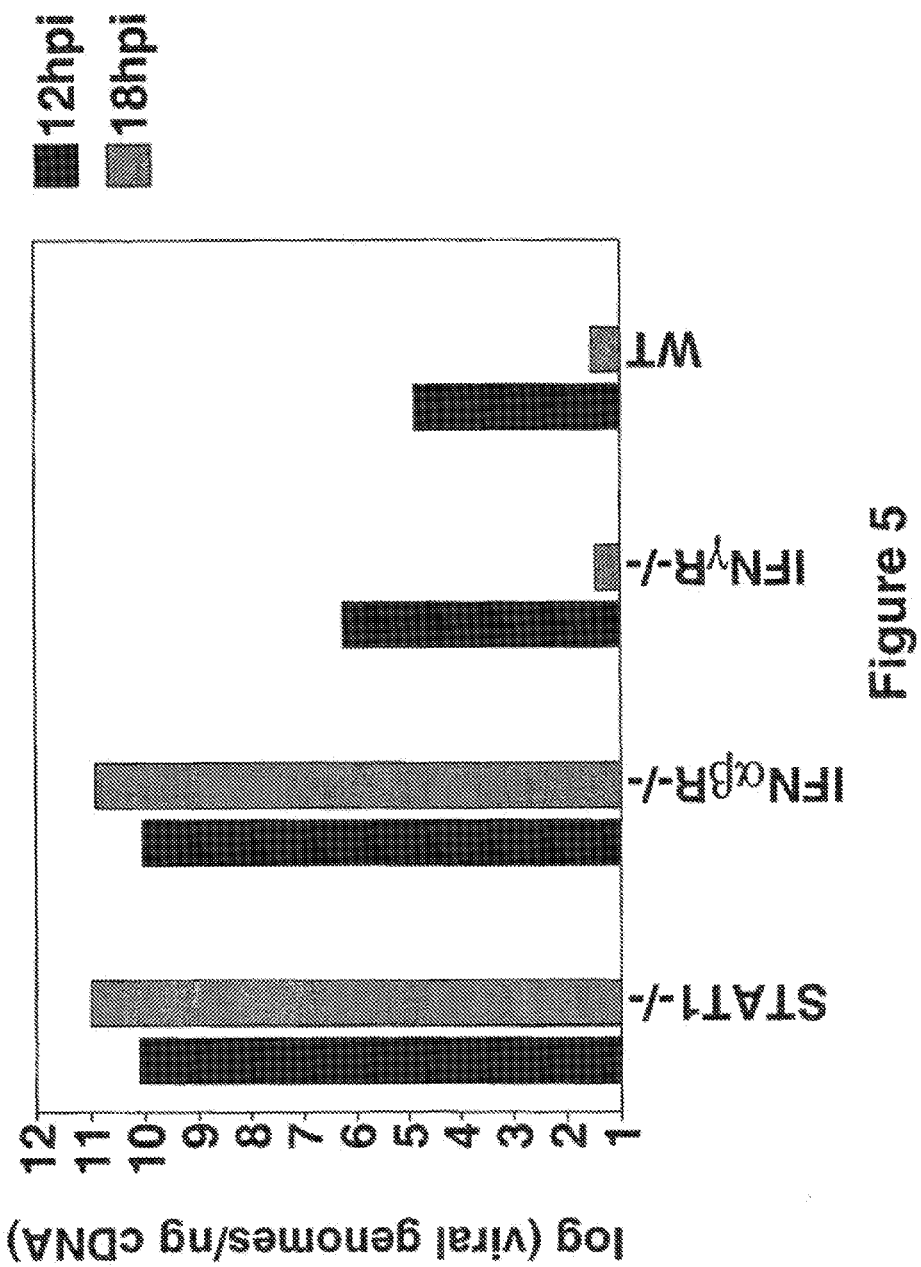
FIG. 5 illustrates a multi-step growth curve in norovirus-permissive cells infected with plaque-derived norovirus.

In these experiments, as shown in FIG. 5, accumulation of viral genomes in infected macrophages was measured using quantitative real time PCR (Karst, S. M. et al., Science 299: 1575-1578, 2003). STAT-1-deficient (STAT-1−/−), interferon-αβ receptor-deficient (IFN-αβR−/−), interferon-γ receptor-deficient (IFN-γR−/−), or wild type bone marrow macrophages were infected with MNV-1, as discussed supra. At 12 hr and 18 hr post infection (h.p.i.), cells were lysed and cDNA prepared from cellular RNA. The number of viral genomes as normalized to cDNA levels was then determined. The results show that viral RNA expression can be measured to assess replication, and that bone marrow macrophages can support norovirus replication when deficient for STAT-1 or an interferon-αβ receptor.

Example 17

This example illustrates that MNV-1 productively infects established macrophage cell lines including a human-murine fusion cell line.

Figure 6:
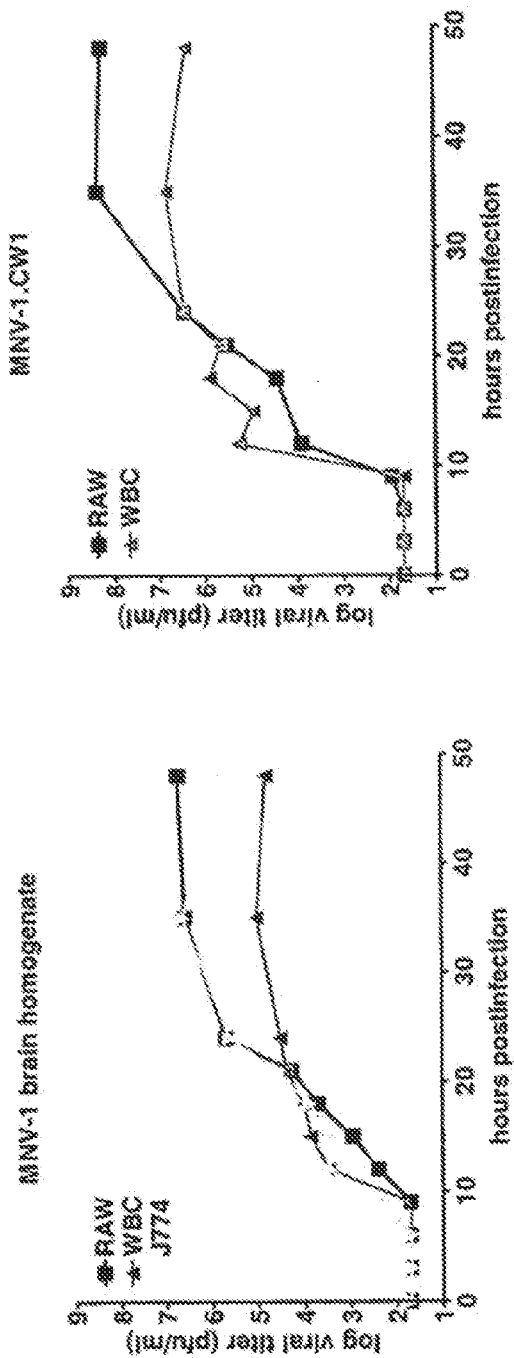
FIG. 6 illustrates MNV-1 infection in established macrophage cell lines.

In this example, as shown in FIG. 6, RAW 264.7, J774A.1 and WBC264-9C cells (a human leukocyte/murine macrophage hybrid, ATCC catalog number HB-8902) were examined for their permissiveness towards norovirus infection. In these experiments, the cells were infected as described in example 12 with an MOI of 0.05 with MNV-1 containing brain homogenate or plaque-purified MNV-1.CW1. Cells were subjected to freezing and thawing at various time intervals after infection. Virus production was the measured by titering using the plaque assay described in Example 3. The data in FIG. 8 is from a single experiment. The data indicate that MNV-1 productively infects each of these macrophage cell lines.

Example 18

This example illustrates a consensus sequence of a murine norovirus.

This sequence, as shown in FIG. 7, consists of 7382 nucleotides of a single stranded (positive strand) RNA molecule which can serve as a murine norovirus genome.

Example 19

This example illustrates a screen for an anti-viral compound.

In this example, a candidate anti-viral compound is added to a culture comprising RAW cells inoculated with MNV-1. Twelve hours after infection, a plaque assay as described in Example 3 is performed on virus released by the culture. A reduction in the number of plaques formed in the plaque assay, compared to the number of plaques formed in a plaque assay on a control culture in which the candidate anti-viral compound was not added, indicates that the candidate compound has anti-viral activity. Further investigation can indicate the viral protein or stage of viral life cycle targeted by the candidate anti-viral compound.

Example 20

This example illustrates a screen for an anti-viral compound.

In this example, a candidate anti-viral compound is added to a culture comprising RAW cells inoculated with MNV-1. Eight hours after infection, cells are harvested and lysed, and lysate samples are applied to wells of an ELISA plate. ELISAs are performed on the lysate samples using, for primary antibodies, mouse monoclonal antibodies directed against norovirus polyprotein protease, norovirus RNA polymerase, norovirus VPG, norovirus NTPase or norovirus capsid protein (such as monoclonal antibody MAb A6.2 illustrated in Example 13 and FIG. 2). Antibody binding is revealed using a goat anti-mouse secondary antibody conjugated with horseradish peroxidase and a chromogenic HRP substrate. Signal is quantified by measuring light absorbance using an ELISA plate reader. A reduction in the light absorbance of an ELISA well probed with an antibody compared to the light absorbance of a well coated with lysate from a parallel control sample in which the candidate anti-viral compound was not added, indicates that the candidate compound caused a reduction in accumulation of the antibody's target antigen. This observation indicates that the candidate molecule merits further investigation as an anti-viral compound directed against the accumulation of the target antigen.

Example 21

Cells, mice, and virus. This example illustrates RAW 264.7 cells which were purchased from ATCC and maintained in DMEM (Cellgro) supplemented with 10% low-endotoxin fetal calf serum (FCS, HyClone), 100 U penicillin/ml, 100 µg/ml streptomycin, 10 mM N-2-hydroxyethylpiperazine-N'-2-ethanesulfonic acid (HEPES), and 2 mM L-glutamine. Bone marrow was harvested from STAT1−/− mice (Taconic) and primary macrophages were cultured as previously described (Heise et al., 1998, Virology v. 241, p. 331). Mice were housed at Washington University in accordance with all federal and university policies. In vitro virus infections were performed as described above with either the original stock of MNV-1 consisting of brain homogenate from infected IFNαβγR−/− mice (as in FIG. 1) or the plaque purified stock of MNV-1 passaged 3 times on RAW 264.7 cells (referred to in this work as MNV-1.CW1) (as in FIGS. 2 and 3). The virus stock, multiplicity of infection (MOI), and length of infection are indicated in individual experiments.

Example 22

RT-PCR amplification of the 5' end of MNV-1. This example illustrates total RNA which was isolated from infected cells or tissue using the TRIzol reagent. One microgram of RNA was used as template in RT-PCR reactions performed with the Titanium One-Step RT-PCR kit (Clontech), following the manufacturer's protocol, and viral-specific PCR primers (sense=cgacttggaaatgcttggcgctca; antisense=ttgcgtttctctgtgttg). Two microliters of the RT-PCR product were then used as template in nested PCR (sense=atcaatatcaaaacggcg; antisense=ttgcgtttctctgtgttg). The nested PCR product was gel-purified, cloned into pGEM-T Easy (Promega), and sequenced by the Massachusetts General Hospital DNA Core Facility. Sequences were aligned to the MNV-1 genomic sequence with the VectorNTI contig program. The 5' end of the genome is homologous to other norovirus and calicivirus 5' genomic ends and to the ends of subgenomic RNAs as well (FIG. 12).

Example 23

Ribonuclease protection assays. This example illustrates ribonuclease protection assays (FIGS. 10, 13, 14) which were performed with the Multi-Probe RNase Protection Assay System (BD RiboQuant) following manufacturer's protocols. The marker probe was generated by in vitro transcription of 1 microliter of the mCK-5 probe template set (BD RiboQuant). A plasmid containing the MNV-1 lariat nested PCR product adjacent to the T7 promoter was linearized with SalI and in vitro transcribed with T7 in the presence of $^{32}$P-UTP to generate the lariat probe. A plasmid containing nucleotides 1-1699 of the MNV-1 genome adjacent to the SP6 promoter was linearized with Bsu361 and in vitro transcribed with SP6 to generate the 5' end positive control probe. One microgram of linearized plasmid was used in each labeling reaction. A parallel amount of probe (between $10^5$-$10^6$ cpm, depending on the labeling efficiency of individual probe preparations) was hybridized with 1-5 micrograms of template RNA from either MNV-1 infected or mock infected RAW 264 cells prior to RNase digestion. Reactions were run out on 4.75% polyacrylamide sequencing gels. Also included on the gels were 5000-10,000 cpm of markers and undigested probes.

Example 24

Figure 14:
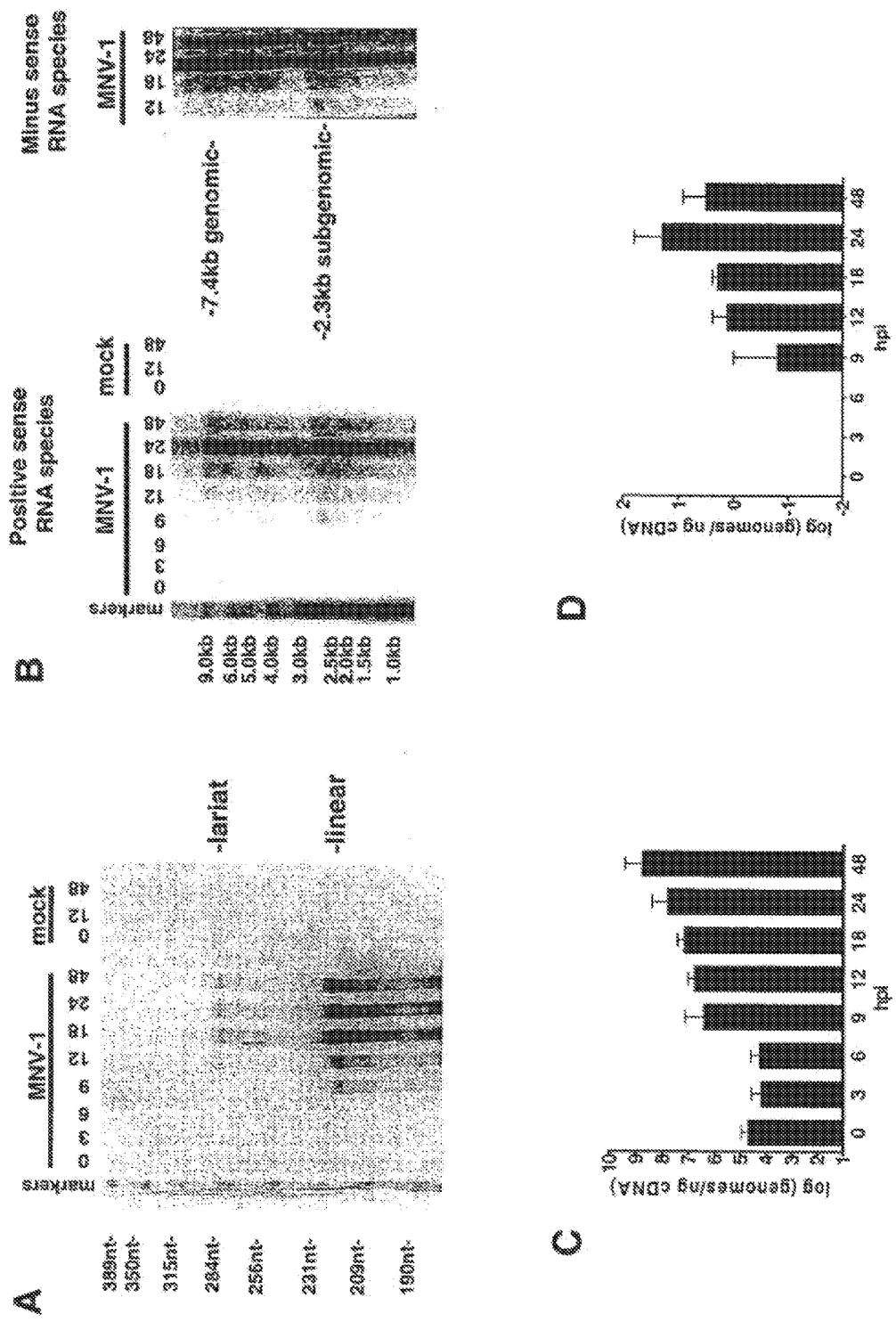
FIG. 14 illustrates detection of the lariat form during replication of the virus by both RNase protection assays and real time PCR assay.

Northern hybridization of viral RNA. This example illustrates Northerns to detect MNV-1 RNA species which were performed using techniques well known in the art (FIGS. 3, 14). Briefly, a portion of the MNV-1 genome containing nucleotides 5618-7040 was cloned into pGEM-T Easy (Promega) between the T7 and SP6 promoters. This plasmid was linearized with Bsu361 and in vitro transcribed with the SP6 RNA polymerase to generate the sense-specific probe, or with the T7 RNA polymerase to generate the antisense-specific probe. 1-2 micrograms of total RNA from MNV-1 infected or mock infected RAW 264 cells were run on 1.0% agarose/formaldehyde gels. RNA Millennium Size Markers (Ambion) were used on each gel for size determination.

Example 25

FIG. 14. Real-time RT-PCR analysis of viral RNA linear and lariat species. This example illustrates equivalent amounts of total RNA which were used to generate single-stranded cDNA using ImProm-II reverse transcriptase (Promega), and triplicate quantitative RT-PCR reactions were performed. Primers specific to a 93 nucleotide region of MNV-1 ORF3 (sense=gttcaaaaccttcaggcaa; antisense=gatccttctgggcttgaa) were used in the assay to detect linear genomes. Primers specific to a 98 nucleotide region of MNV-1 surrounding the lariat branch point (sense=ggtaggcaagtgacatcccgc; antisense=gtgttgcgcacagagggc) were used in the assay to detect lariat genomes. The number of genomes in each case was determined by comparison to a standard curve. In addition, triplicate reactions were also performed with primers specific to cellular 18S rRNA to normalize overall levels of cDNA in each sample. The data is reported as genomes/ng cDNA on a logarithmic scale.

Example 26

FIG. 8. This example illustrates RT-PCR amplification across the 5' end of the MNV-1 genome suggests that the MNV-1 genome adopts an unexpected lariat conformation. A) The experimental design to amplify, and thus sequence, the 5' end of the MNV-1 genome consisted of an RT-PCR across a putative branch point between the 5' end and the poly(A) tail. Shown are the 5' end and the poly(A) tail (in black), and the sense and antisense nested PCR primers (in gray) on both a linear and a lariat genome. B) The sequence of the RT-PCR product shows the 5' end adjacent to nucleotide (nt) 7180 of the genome, instead of the poly(A) tail. The expected sequence (5' end-poly(A) tail junction) is shown in the top line and the obtained sequence (5' end-nt7180) is shown in the bottom line. The primer sequences are in gray and the 5' end sequence is in italics. C) The same sequence has been obtained from multiple independent sources of RNA from cells under various infection conditions with MNV-1. Together the data show that a novel form of viral RNA which unites the 5' end of the genome with an internal T present near the 3' end of the genome exists in infected cells.

Example 27

Figure 9A:
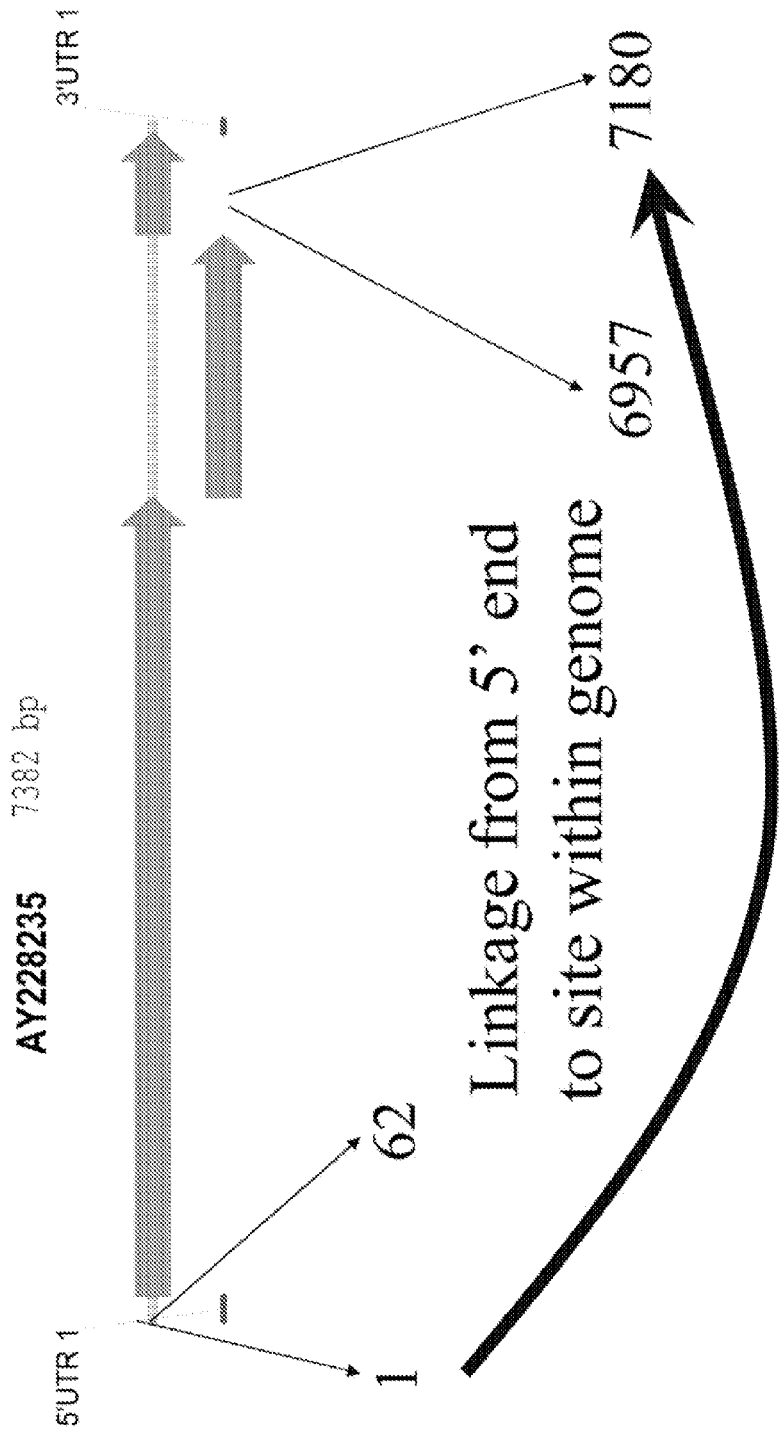
FIG. 9 illustrates the location of the lariat insertion within the entire genome of the virus.
Figure 9C:
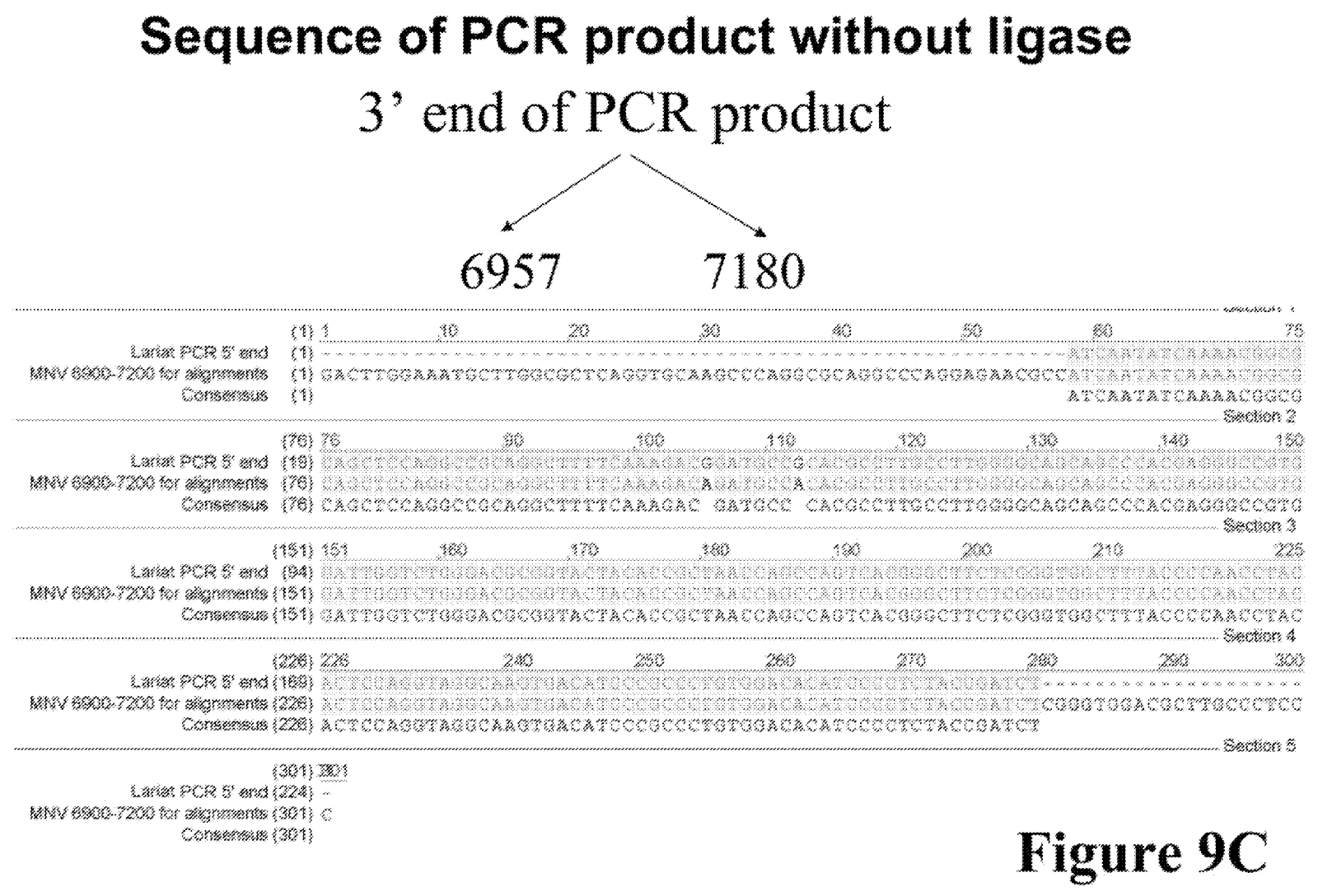

FIG. 9. This example illustrates the sequence of a PCR product without ligase. FIG. 9A is a schematic representation of the viral lariat. Shown is a schematic of the viral genome with coordinates of the sequences joined in the lariat. FIG. 9B illustrates nucleotides 1-62 of the viral genome revealed using the methods presented in example 26, united with nucleotides 6957 to 7180 of the viral genome. FIG. 9C illustrates nucleotides 6957 to 7180 of the viral genome revealed using the methods presented in example 26, united with nucleotides 1-62 of the viral genome. This covalent linkage between the 5' end of the genome and an internal nucleotide defines the lariat form of the genome.

Example 28

FIG. 10. This example illustrates, using RNase protection, that the viral lariat exists in infected cells. An RNase protection probe was generated that spans the lariat junction between the 5' end of the genome and the internal NT defined in FIGS. 8 and 9. If the lariat exists than a 283 nt portion of the probe should be protected. Such a band is observed, demonstrating that the lariat exists. Hence, a method other than PCR confirms that the lariat exists in infected cells.

Example 29

FIG. 11. This example illustrates the sequences of the lariat junction and the 5' end of the MNV-1 genome closely match consensus sequences for mammalian splicing. As lariats are formed as an intermediate in mammalian splicing, the sequences of the MNV-1 genome in the region of the viral lariat were compared to the sequences used in host splicing. The 5' end of the MNV-1 genome (and not shown the 5' end of the MNV-1 subgenomic RNA) closely match the 5' intronic sequences involved in cellular splicing. Furthermore, while the MNV-1 lariat utilized a T rather than an A as is characteristic of host cell splicing, the internal sequences surrounding the MNV-1 lariat site contain a consensus match to the sequences internal to the host intron that is used to initiate lariat formation. These data show that the MNV-1 lariat formation occurs in regions showing complete matches to the sequences used in host cell lariat formation as it occurs during the splicing reaction.

Example 30

FIG. 12. This example illustrates comparison of the viral genomes of noroviruses and other caliciviruses and shows that the consensus sequences described in example 29 are conserved across many viruses. This shows that these sequences are common to many viruses consistent with involvement of viral lariats and lariat formation playing a role in infection for a range of viruses.

Example 31

Figure 13:
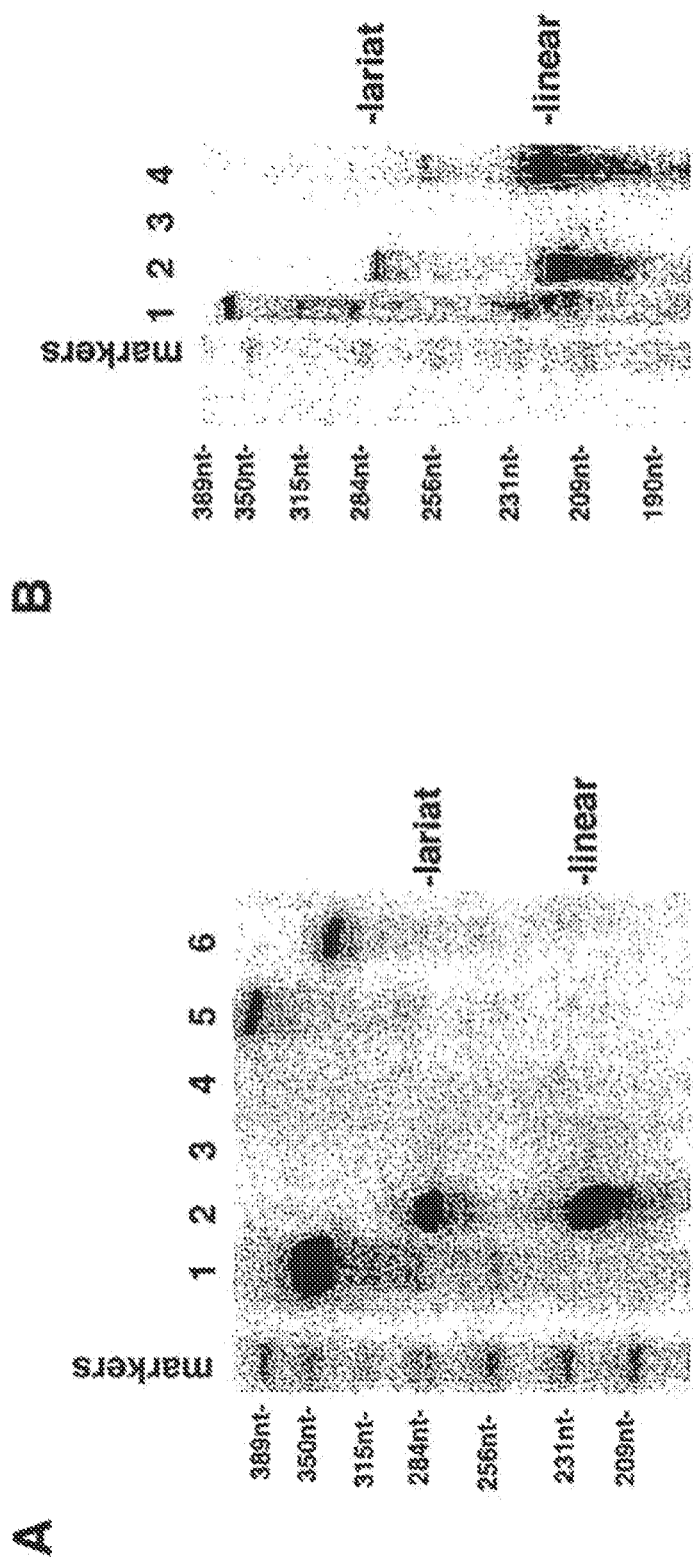
FIG. 13 illustrates demonstration of the lariat form of the MNV-1 genome.

FIG. 13. This example illustrates, by ribonuclease protection assay (RPA), the lariat conformation of the MNV-1 genome can be detected in infected cells, but not in viral particles. A) Products corresponding to both linear and lariat viral genomes are detected with an RPA probe designed to anneal across the putative lariat branch point. Undigested lariat probe was run in lane 1 to verify the size of the labeled probe (373 nt). Lariat probe was hybridized with RNA from MNV-1 infected cells (lane 2), RNA from mock infected cells (lane 3), or tRNA (lane 4) prior to RNase digestion. The expected size for lariat probe annealed to linear genomes is 223 nt, while the expected size for lariat probe annealed to lariat genomes is 284 nt. A positive control probe to the 5' end of the genome was either run undigested (lane 5; expected size of 435 nt) or hybridized with RNA from MNV-1 infected cells prior to digestion (lane 6; expected size of 364 nt annealed to either linear or lariat genomes). RNA for this experiment was isolated from RAW 264.7 cells either infected with MNV-1 at an MOI of 0.25 or mock infected for 3 days. B) The lariat-specific product is detected in infected cells but not in purified viral particles by RPA. Lane 1=undigested lariat probe; lane 2=lariat probe+2 micrograms of total RNA from MNV-1 infected cells 18 hpi; lane 3=lariat probe+2 micrograms of total RNA from mock infected cells 18 hpi; and lane 4=lariat probe+250 nanograms of RNA from MNV-1 virions. RNA for this experiment was isolated from RAW 264.7 cells either infected with MNV-1.CW1 at an MOI of 10.0 or mock infected (lanes 2 and 3, respectively), or from MNV-1.CW1 virions purified 3 times on cesium chloride gradients (lane 4). These data show that the lariat is present in infected cells but not the viral particle. This proves that the lariat is formed during viral infection in a process that occurs in the infected cell.

Example 32

FIG. 14. This example illustrates the lariat conformation of the MNV-1 genome is present in infected cells during the period of viral RNA replication. A) Ribonuclease protection assay shows lariat genomes are detected only after newly synthesized linear genomes are detectable. 2 micrograms of total RNA from MNV-1 or mock infected cells at each time point (hours post-infection, hpi, listed above the lanes) was hybridized with an equivalent amount of lariat probe prior to RNase digestion. B) One microgram of total RNA from the same samples as in Panel A was run on denaturing gels and probed for either positive or minus sense viral RNA species in Northern hybridization. The expected migrations of genomic and subgenomic species are indicated. The hpi are listed above each lane. The data shown in panels A and B are representative of three independent experiments. One microgram of total RNA from the same samples used in Panels A and B was used in first strand cDNA synthesis, followed by quantitative real time PCR with primers specific for linear genomes (C), or for lariat genomes (D). Levels of viral genomes in both cases were normalized to levels of cellular 18S RNA determined in parallel real time assays. All mock samples were negative in these assays. For Panels C and D, data from three independent experiments was averaged to generate error bars. In all experiments in this figure, RNA was isolated from RAW 264.7 cells infected with MNV-1.CW1 at an MOI of 10.0, or mock infected. These data show that the lariat is formed concurrent with viral RNA synthesis of positive and negative strands of the viral genome. Two independent methods were used. These data also demonstrate that the lariat form of the genome can be quantitatively measured as a readout for viral replication in a permissive cell.

Example 33

Figure 15:
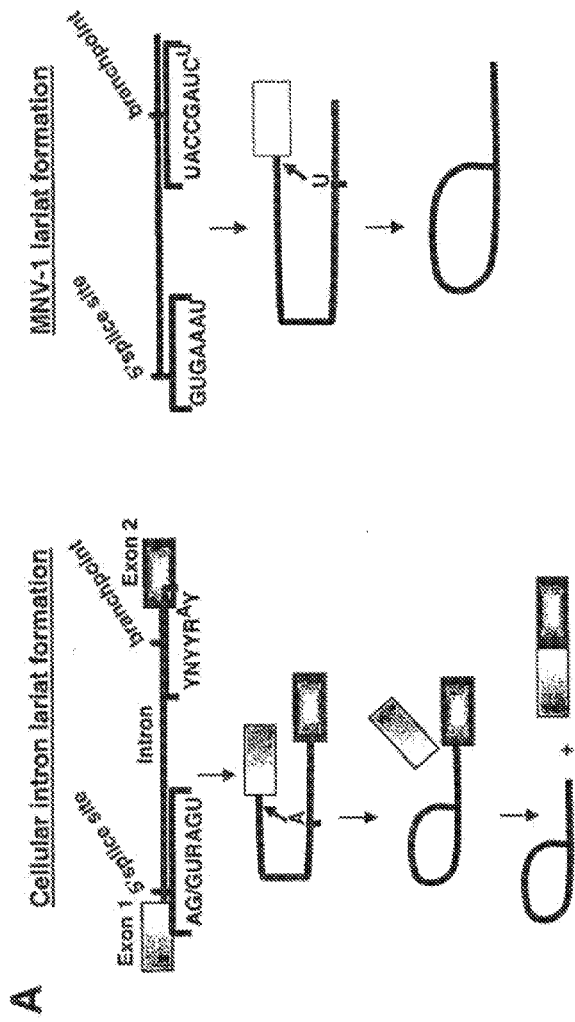
FIG. 15 illustrates implications of the MNV1 lariat conformation.

FIG. 15. This example illustrates a model of lariat formation in the MNV-1 genome. The model is based on similarities to cellular intron lariat formation. The basic steps of cellular splicing are depicted on the left side of Panel A. The sequences required for intron lariat formation, the 5' splice site and the branch point sequences, are indicated. The adenosine residue of the branch point attacks the first guanidine residue of the intron, generating a 2'-5' phosphodiester bond between the two residues. This reaction results in the formation of a lariat in the intronic sequence and brings the 2 exons into proximity. Splicing is then completed by a second attack, specifically the 3' end of exon 1 attacking the 5' end of exon 2 and generating a new phosphodiester bond between the 2 exons. This also results in release of the lariat intron. In the case of the MNV-1 genome, the parallel sequences involved in lariat formation are shown on the right side of Panel A; based on the sequence analysis presented in this work, a uridine residue acts as the branch point residue.

Example 34

FIG. 15. This example illustrates alignment of the genomic and subgenomic 5' ends of calicivirus genomes. B) The alignment shows conservation of the 5' splice site across the family and suggests that lariat formation may be a common event in calicivirus replication. FIG. 15 thus illustrates the implication of the demonstration of the novel lariat form of the viral genome, the conservation of sequences in the viral genome involved in host cell splicing, and the use of T rather than an A as the branch point in the lariat.

Example 35

This example illustrates cell cultures and mice used in experiments presented herein.

In these experiments, mouse embryo fibroblasts were generated and cultured as described previously (Pollock J L, et al., Virology 227, 168-179, 1997). RAW 264.7 cells were purchased from ATCC (Manassas, Va., United States) and maintained in DMEM (Cellgro, Mediatech, Herndon, Va., United States) supplemented with 10% low-endotoxin fetal calf serum (SH30070.03, HyClone, Logan, Utah, United States), 100 U penicillin/ml, 100 µg/ml streptomycin, 10 mM HEPES (N-2-hydroxyethylpiperazine-N'-2-ethanesulfonic acid), and 2 mM L-glutamine (Biosource, Camarillo, Calif., United States). Bone marrow was harvested and macrophages were cultured as described previously (Heise M. T., et al., Virology 241, 331-344, 1998). To culture dendritic cells, bone marrow cells were resuspended in RPMI1640 containing 10% low endotoxin fetal calf serum, 2 mM L-glutamine, 1 mM sodium pyruvate (Biosource), 100 U penicillin/ml, 100 µg/ml streptomycin, 1% nonessential amino acids (Biosource), and 20 ng/ml recombinant mouse GM-CSF (BD Biosciences, San Jose, Calif., United States) and plated at a concentration of 3×105 cells/ml in six-well plates in a total volume of 3 ml per well. The percentage of CD11c-positive dendritic cells was determined by FACS staining after culturing cells for 7 d at 37° C. and 5% CO2. Approximately 70% of the cells were CD11c positive.

Wt 129 and STAT1−/− mice were purchased from Taconic (Germantown, N.Y., United States). IFNαβR−/−, IFNγR−/−, and IFNαβγR−/− (Muller et al., Science 264: 1918-1921, 1994), PKR−/− (Yang et al., EMBO J 14: 6095-6106, 1995), and iNOS−/− (MacMicking et al., Cell 81: 1-10, 1995). Mice were bred and housed at Washington University in accordance with all federal and university policies.

Example 36

This example illustrates methods of preparation of rabbit anti-MNV-1 serum.

In these experiments, rabbits were immunized subcutaneously with 140 µg of MNV-1 VLPs in complete Freunds adjuvant and boosted 4 or 8 wk later with 70 µg of MNV-1 VLPs or 50 µg of UV-inactivated CsCl-purified MNV-1 in incomplete Freunds adjuvant. Serum was collected two weeks after the last boost, heat inactivated, and filtered before use.

Example 37

This example illustrates immunohistochemistry methods used in the present experiments.

In these methods, seven-week-old STAT1−/− mice were infected orally with 25 µl of brain homogenate containing MNV-1 ($6 \times 10^5$ pfu) or brain homogenate from uninfected mice. Organs were collected into 10% buffered formalin and embedded in paraffin for sectioning by standard methods. Immunohistochemistry was performed as described previously (Weck et al., Nat Med 3: 1346-1353, 1997) using tyramide signal amplification (NEN Life Science Products, Boston, Mass., United States). Slides were blocked in tyramide signal amplification blocking reagent (NEN Life Science Products) containing 10% mouse serum (IHC blocking buffer) for 30 min before adding antibodies. Serum was diluted 1:20,000 (spleen) or 1:100,000 (liver) in IHC blocking buffer, and tissue sections were incubated overnight at 4° C. Horseradish peroxidase-conjugated donkey anti-rabbit secondary antibody (Jackson ImmunoResearch Laboratories, West Grove, Pa., United States) was diluted 1:250 in IHC blocking buffer and applied to tissue sections for 1 h at room temperature. Biotin-tyramide was added at a dilution of 1:50 in 1× amplification diluent (NEN Life Science Products) for 10 min, slides were washed, and horseradish peroxidase-conjugated streptavidin (NEN Life Science Products) was added at a 1:100 dilution in tyramide signal amplification blocking reagent and incubated for 30 min at room temperature before washing. Antigen was visualized by a 3-min staining with a solution of 3,3'-diaminobenzidine (Vector Laboratories, Burlingame, Calif., United States). Slides were washed and lightly counterstained with hematoxylin, dehydrated, and covered with Cytoseal XYL (Richard Allan Scientific, Kalamazoo, Mich., United States) coverslips. No staining was observed in infected tissues incubated with pre-immune serum or mock-infected tissues incubated with immune serum.

Example 38

This example illustrates methods for infection of cells.

In these experiments, adherent cells were plated in 12-well plates and allowed to attach for several hours. Infections were carried out at a multiplicity of infection (MOI) of 0.05 or 2.0 for 30 min on ice in a volume of 0.5 ml per well. dendritic cells were infected in bulk in the same volume. Cells were then washed twice with 2 ml of ice-cold PBS per well. To allow viral entry, 1 ml of medium was added to each well, and cells were incubated at 37° C. and 5% $CO_2$ for different time periods. For growth curve samples, infected cells and media were subjected to two or three cycles of freezing and thawing before plaque titration.

Example 39

This example illustrates generation of monoclonal antibody mAb A6.2.

In these experiments, an MNV-1-seropositive 129 mouse was injected intraperitoneally with 100 µl of a brain homogenate containing MNV-1, and the spleen was harvested 3 d later. Hybridoma fusions were performed as described previously (Virgin et al., J Virol 65: 6772-6781, 1991) with the following modifications. Hybridoma supernatants were screened for binding to recombinant MNV-1 capsids by ELISA as described (Karst et al., Science 299: 1575-1578, 2003). Stable hybridomas were characterized by Western blotting and ELISA after two rounds of subcloning by limiting dilution. A6.2 was unable to detect MNV-1 capsid protein by Western blot analysis but specifically bound to recombinant MNV-1 capsids by ELISA. The A6.2 isotype is IgG2a and was determined using the mouse mAb isotyping kit (Amersham Biosciences, Amersham, United Kingdom) and following manufacturer's protocol.

Example 40

This example illustrates MNV-1 plaque assay and plaque neutralization assay methods.

In these experiments, RAW 264.7 cells were seeded into six-well plates at a density of $2 \times 106$ viable cells per well. On the following day, 10-fold dilutions of virus inoculum were prepared in complete DMEM medium and plated in duplicate wells. Plates were incubated for 1 h at room temperature on a rocking apparatus before aspirating the inoculum and overlaying the cells with 2 ml of 37-40° C. 1.5% SeaPlaque agarose in MEM supplemented with 10% low-endotoxin fetal calf serum, 1% HEPES, 1% penicillin/streptomycin, and 2% glutamine (complete MEM) per well. Plates were incubated at 37° C. and 5% CO2 for 2 d. To visualize plaques, cells were stained with 2 ml of 56° C. 1.5% SeaKem agarose in complete MEM containing 1% neutral red per well for 6-8 h.

For plaque neutralization assays, differing concentrations of purified mAb (A6.2, anti-MNV-1 capsid; isotype control, 10H2, anti-reovirus µ1c) were incubated with equal plaque-forming units of either MNV-1.CW1 or MNV-1 brain homogenate for 30 min at 37° C. prior to performing the MNV-1 plaque assay.

Example 41

This example illustrates methods of purification of virus particles.

In these experiments, RAW 264.7 cells were infected with MNV-1.CW1 for 2 d at an MOI of 0.05. Cellular debris was removed from freeze/thaw lysates by low-speed centrifugation for 20 min at 3,000 rpm. Supernatants were layered on top of a 5-ml 30% sucrose cushion and centrifuged at 4° C. for 2.5 h at 27,000 rpm (90,000 g) in a SW32 rotor. Cell pellets were then resuspended in PBS and mixed with CsCl to a final density of 1.335 g/cm3 and centrifuged for at least 18 h at 35,000 rpm (115,000 g) in a SW55 rotor. A wide lower band (1.35.+−.0.01 g/cm3) and narrow upper band (1.31.+−.0.01 g/cm3) were typically seen in the gradient. Each band was collected by puncturing the side of the tube with a needle before overnight dialysis against PBS at 4° C.

Example 42

This example illustrates protein analysis methods.

In these experiments, CsCl-purified virions were separated by SDS-PAGE gel electrophoresis using standard protocols (Sambrook et al., supra). Proteins were visualized by Coomassie blue staining using the Simply Blue safe stain (Invitrogen, Carlsbad, Calif., United States) according to manufacturer's instructions. For Western blot analysis, proteins were transferred to nitrocellulose membrane and incubated with an anti-MNV-1-capsid rabbit polyclonal antibody, followed by a peroxidase-labeled secondary antibody, and visualized by ECL (Amersham Biosciences) according to manufacturer's instructions. Immunoprecipitation of radiolabeled infected cell lysates was performed as described previously (Sosnovtsev et al., J Virol 76: 7060-7072, 2002) with serum obtained from a 129 wt mouse infected orally with MNV-1.

Example 43

This example illustrates Northern blotting methods used in the present analyses.

In these experiments, the region of the MNV-1 genome from nt 5,617 to 7,039 was amplified by RT-PCR and cloned into the pGEM-T Easy (Promega, Madison, Wis., United States) vector between the T7 and SP6 promoters. The resulting plasmid was linearized with Bsu361 and in vitro transcribed with SP6 RNA polymerase (Roche, Indianapolis, Ind., United States) to generate RNA transcript probes for detection of positive-sense viral RNA, or with T7 polymerase (Roche) to generate transcripts for detection of negative-sense viral RNA. To label probes, the transcription reaction was carried out in the presence of $P^{32}$-UTP according to manufacturer's recommendations. Total RNA from virus-infected or mock-infected cells was isolated using Trizol (Invitrogen) according to the manufacturer's recommendations. One microgram of total RNA from MNV-1- or mock-infected cells was subjected to electrophoresis on a 1% formaldehyde gel. RNA Millennium Size Markers (Ambion, Austin, Tex., United States) were used as size markers. Northern blotting was performed using standard protocols (Sambrook et al., Molecular Cloning: A Laboratory Manual, 2nd ed. Cold Spring Harbor (N.Y.): Cold Spring Harbor Laboratory Press. 3. v., 1989). Probes were hybridized overnight at 68° C. in 50% formamide containing 6×SSC, 5×Denhardt's, 0.5% SDS, and 100 µg/ml ssDNA.

Example 44

This example illustrates MNV-1 ELISA methods used in the present analyses.

In these experiments, ELISA was performed as described previously (Karst et al., Science 299: 1575-1578, 2003) with the following modifications. ELISA plates were coated overnight at 4° C. with CsCl-purified MNV-1 particles at 0.2 or 1.0 µg/well. Diluted purified anti-MNV-1-capsid (A6.2) and isotype control (reovirus 10H2) mAbs, as well as the peroxidase-labeled secondary antibodies, were incubated for 60 min at 37° C.

Example 45

This example illustrates methods of electron microscopy analysis.

In these experiments, negative staining electron microscopy of CsCl-purified virions was performed as described previously (Karst et al., Science 299: 1575-1578, 2003). For thin-section electron microscopy, RAW cells were infected with MNV-1.CW1 at an MOI of 2.0, as described above. At various times postinfection cells were washed with PBS and fixed with 3% glutaraldehyde diluted in PBS at room temperature for 2 h. Cells were pelleted and washed with buffer prior to incubation with 1% osmium tetroxide (in 0.1 M cacodylate buffer) for 40 min at room temperature. After washing, the cells were incubated overnight at 4° C. in 2% uranyl acetate/80% acetone. The pellets were then dehydrated with an acetone series and embedded in Epon before polymerization at 65° C. for 72 h. Ultrathin sections (60 nm) were cut with a Micro Star (Huntsville, Tex., United States) diamond knife, and the sections were stained and contrasted with uranyl acetate and lead citrate before viewing on a JOEL 1010 electron microscope at 80 kV. Images were captured on a MegaView III side-mounted CCD camera (Soft Imaging System, Lakewood, Colo., United States), and figures were processed using Adobe Photoshop software (Adobe Systems, San Jose, Calif., United States).

Example 46

This example illustrates methods of consensus sequence analysis of viral RNA.

In these experiments, RNA was extracted from brain tissue or cell culture material with Trizol (Invitrogen) and reverse transcribed with Superscript II enzyme (Invitrogen). Genome-specific sequences were PCR-amplified with Elongase enzyme (Invitrogen) to produce seven overlapping fragments. The DNA fragments were gel-purified and sequenced directly with reagents in the BigDye Terminator version 3.1 Cycle Sequencing Kit (Applied Biosystems, Foster City, Calif., United States) on a 3100 DNA sequencer (Applied Biosystems). Data were analyzed with the Sequencher software package (Gene Codes Corporation, Ann Arbor, Mich., United States).

Example 47

This example illustrates MNV-1 replication in murine macrophages and dendritic cells.

Figure 16:
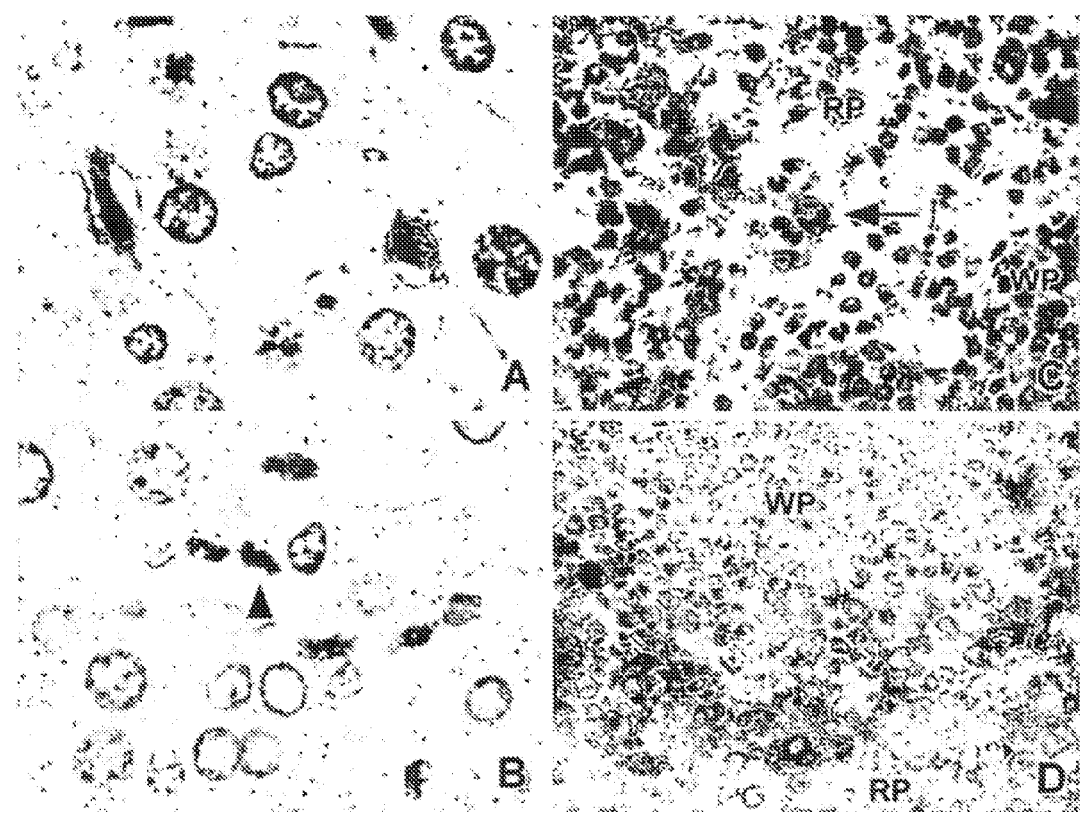
FIG. 16 illustrates MNV-1-specific staining in vivo in macrophage lineage cells.

In these experiments, STAT1−/− mice were infected with MNV-1 by the oral route and tissue sections analyzed by immunohistochemistry for the presence of MNV-1 protein. MNV-1-specific staining was observed in spleen and liver 2 d postinfection (FIG. 16). Interestingly, in the liver, Kupffer cells (resident macrophages of the liver) lining the sinusoids were specifically stained by MNV-1 immune serum (compare FIG. 16, Panels A and B). In the spleen, staining was found primarily in the red pulp and the marginal zone, but also in non-lymphoid cells within the white pulp (FIG. 16, Panels C and D). This pattern is consistent with staining of macrophages and dendritic cells (Metlay et al., J Exp Med 171: 1753-1771, 1990; Leenen et al., J Immunol 160: 2166-2173, 1998). Furthermore, in some cases virus-antigen-positive macrophages were detected (FIG. 16, Panel C).

As shown in FIG. 16, MNV-1-specific staining in vivo occurs in cells of the macrophage lineage. In these experiments, immunohistochemistry was performed on liver (FIG. 16, Panels A and B) and spleen (FIG. 16, Panels C and D) sections from STAT1−/− mice 2 d after oral infection. MNV-1-specific staining was seen in Kupffer cells of infected livers when probed with MNV-1 immune (A) but not preimmune (B) serum. A selected Kupffer cell lining the sinusoid is indicated by an arrowhead. MNV-1-specific staining consistent with macrophages was seen in red pulp (C) and marginal zone (D) in the spleen. The arrow indicates a cell with macrophage morphology. No staining was observed in tissues from mice infected for 1 d, in infected tissues incubated with preimmune serum, or in mock-infected tissues incubated with immune serum. RP, red pulp; WP, white pulp.

These experiments illustrate that MNV-1 infects macrophages in vitro.

Example 48

This example illustrates permissiveness of hematopoietic lineage cells for MNV-1 replication in vitro.

Figure 17:
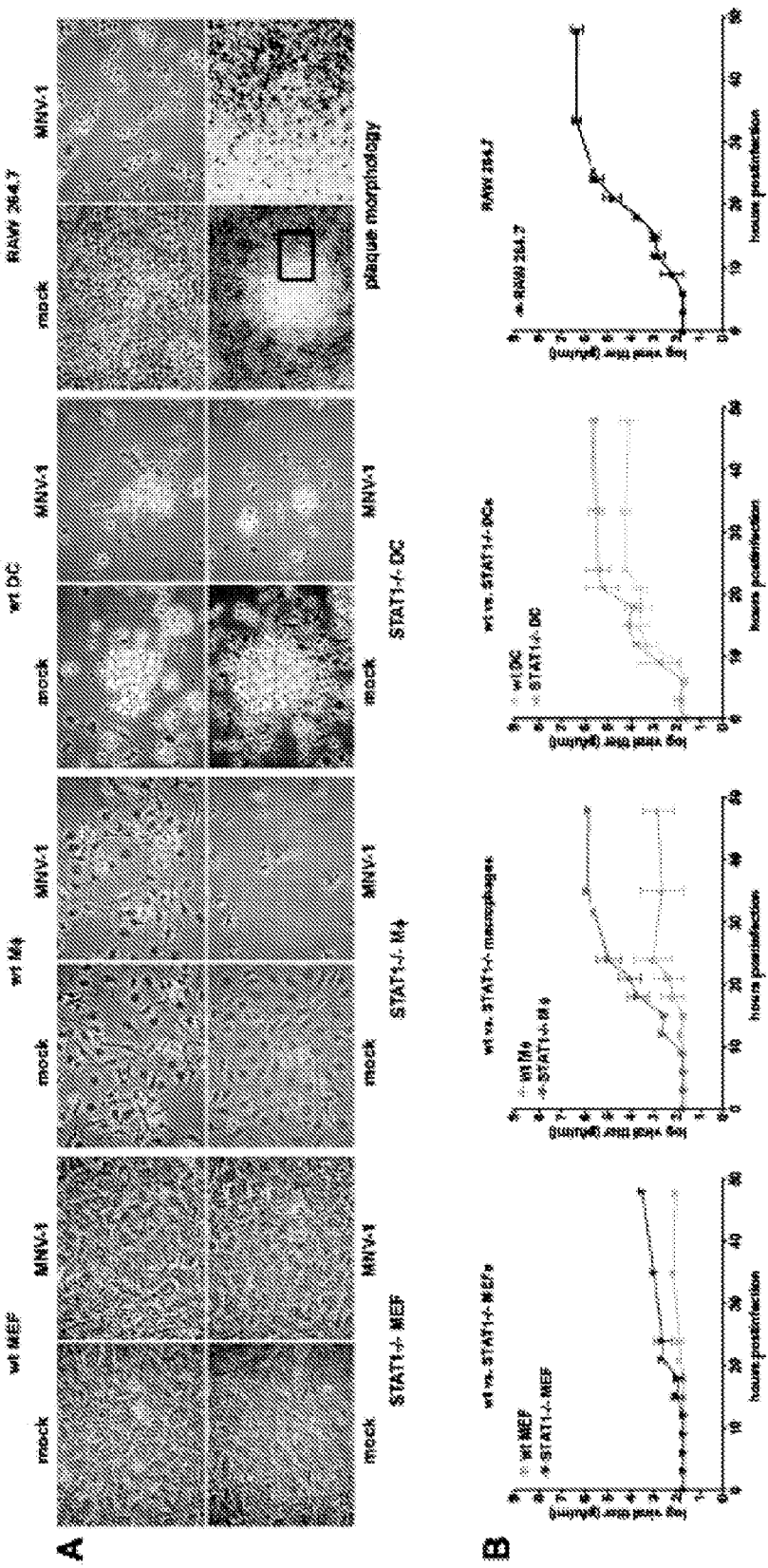
FIG. 17 illustrates replication of MNV-1 from brain homogenate in cells of the dendritic cell and macrophage lineage in vitro.

In these experiments, bone-marrow-derived macrophages (BMMΦ) and bone-marrow-derived dendritic cells (BM-DCs) were inoculated with a MNV-1 stock derived from the brain of infected IFNαβγ receptor−/− (IFNαβγR−/−) mice (Karst et al., Science 299: 1575-1578 2003). Cytopathic effect (CPE) in cell monolayers was visible within 2 d in STAT1−/− BMMΦ and BMDCs, but not STAT1−/− murine embryonic fibroblasts (MEFs)(FIG. 17, Panel A). While BMDCs showed CPE even when STAT-1 was present, wild-type (wt) BMMΦ exhibited less CPE than their STAT1−/− counterparts.

As shown in FIG. 17, MNV-1 from brain homogenate replicates in cells of the dendritic cell and macrophage lineage in vitro.

BMDCs and BMMΦ, as well as MEFs from wt or STAT1−/− mice, and RAW 264.7 cells were infected with a multiplicity of infection (MOI) of 0.05.

Panel 17A: MNV-1 causes cytopathic effect in permissive cells. MNV-1- or mock-infected cells were observed by light microscopy 2 d postinfection. The boxed area is magnified further to show the border of the plaque.

Panel 17B: Infected cell lysates were analyzed in two to four independent experiments by plaque assay at various timepoints postinfection to calculate standard deviations. For wild type BMMφ, MNV-1 growth was detected in two out of four experiments.

These data show that MNV-1 have a marked tropism for macrophages and dendritic cells but not fibroblasts.

This information was used to screen available macrophage cell lines for growth of MNV-1, including the murine lines RAW 264.7 (Raschke et al., Cell 15: 261-267, 1978) and J774A.1 (Ralph et al., J Immunol 114: 898-905, 1975), and the human/murine hybrid line WBC264-9C (Aksamit, Biochem Biophys Res Commun 138: 1001-1008, 1986). These cells also showed visible cytopathic effect (CPE) when inoculated with the MNV-1 stock (FIG. 17; data not shown). In these experiments, plaques were observed when infected RAW 264.7 monolayers were maintained under agarose (FIG. 17, Panel A), allowing us to develop a plaque assay and quantify virus titers.

STAT1−/− BMMΦ, STAT1−/− and wt BMDCs, and RAW 264.7 cells consistently supported the growth of MNV-1, while wt BMMΦ varied in their ability to support virus growth (FIG. 17, Panel B). BMMΦ and BMDCs cells lacking STAT-1 always yielded higher MNV-1 titers than their wt counterparts. Furthermore, a low level of virus replication was observed in STAT1−/− MEFs, but as reported previously, no virus growth was observed in wt MEFs (Karst et al., Science 299: 1575-1578, 2003). MNV-1 replication proceeded rapidly in permissive cells, with newly synthesized infectious virions first detected in cell lysates 9 to 12 hours postinfection (h.p.i.). Taken together, these data indicate that MNV-1 can productively infect macrophages and dendritic cells.

Example 49

This example illustrates verification of viral growth in vitro

Figure 18:
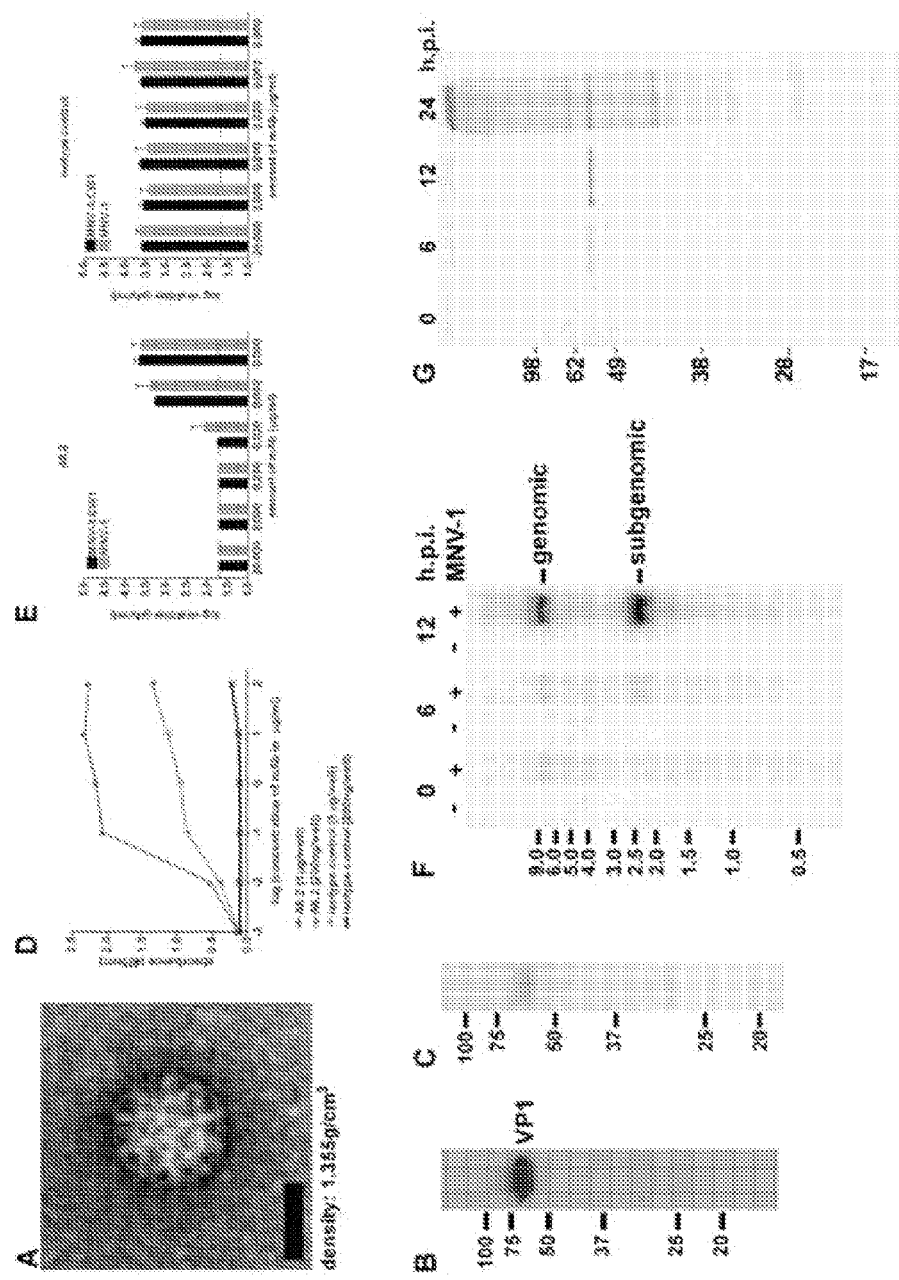
FIG. 18 illustrates characterization of a triple plaque-purified MNV-1.

In these experiments, several approaches were used to verify that the observed CPE and plaques were caused by MNV-1. We first performed a clonal selection from the MNV-1 stock (from infected brain tissue) with three rounds of plaque purification in RAW 264.7 cells to generate the MNV-1.CW1 strain. This strain was amplified in RAW 264.7 cells, after which virus particles were concentrated and subjected to purification by isopycnic centrifugation in CsCl. A distinct band was observed in CsCl gradients at a density of 1.35.+−.0.01 g/cm3, consistent with that described for noroviruses (Kapikian et al., Philadelphia: Lippincott-Raven, pp 783-810, 1996). Examination of the material in this fraction by negative staining electron microscopy showed the presence of virus particles with calicivirus morphology (FIG. 18, Panel A). Furthermore, SDS-PAGE analysis of this material revealed a major protein of approximately 59 kDa, consistent with the calculated mass of the MNV-1 capsid protein (FIG. 18 Panels B,C). Western blot analysis with antibodies generated against bacterially expressed MNV-1 capsid protein (FIG. 18, Panel B) and mass spectrometry (data not shown) confirmed its identity as the MNV-1 capsid protein. A genomic-sized RNA molecule of approximately 7.4 kb was detected in nucleic acid isolated from the purified virions with a probe specific for the MNV-1 genome in Northern blots (data not shown). Finally, a neutralization assay was performed with the monoclonal antibody (mAb) A6.2 specific for the MNV-1 capsid protein (see Materials and Methods). MAb A6.2 specifically bound to CsCl-purified MNV-1 virions in an immunoassay, while the isotype-matched mAb 10H2, an anti-reovirus μ1c mAb (Virgin et al., J Virol 65: 6772-6781, 1991), did not bind (FIG. 18, Panel D). MAb A6.2, but not the isotype control antibody 10H2, showed neutralization activity in a plaque reduction assay for both the virus in the original brain homogenate (MNV-1), and the three-times plaque-purified strain MNV-1.CW1 (FIG. 18, Panel E).

FIG. 18 illustrates characterization of the triple plaque-purified strain MNV-1.CW1.

Panel 18, Panels A-C: MNV-1.CW1 purified on CsCl density gradients was visualized by (A) negative staining electron microscopy, (C) Coomassie staining, and (B) Western blot analysis with a polyclonal anti-MNV-1-capsid antibody. Molecular weight markers are indicated in kiloDaltons.

Panel 18, Panel D: Specific binding of mAb A6.2 to two different concentrations of CsCl-purified MNV-1 particles in an enzyme-linked immunosorbent assay.

Panel 18, Panel E: Neutralization of MNV-1 from brain homogenate and MNV-1.CW1 by mAb A6.2 but not the isotype control (10H2) mAb in a plaque neutralization assay. The assay was repeated three times to calculate standard deviations. The limit of detection is indicated by the dashed line.

Panel 18, Panel F: Timecourse of viral RNA synthesis in RAW 264.7 cells. Northern blot analysis of viral RNA from cells infected with MNV-1.CW1 (MOI of 2.0) or mock-infected cells. The size of RNA markers in kilobases is shown on the left. The positions of subgenomic- and genomic-length RNA are indicated on the right. This timecourse is a representative of two independent experiments.

Panel 18, Panel G: Timecourse of viral protein synthesis in infected RAW 264.7 cells. MNV-1-specific proteins were precipitated from radiolabeled cell lysates of MNV-1.CW1-infected RAW 264.7 cells (MOI of 2.0) at indicated times after infection. The size of the proteins in kiloDaltons is indicated.

Together these data confirm that MNV-1 was the infectious agent associated with viral growth observed in the infected cell cultures.

Example 50

This example illustrates MNV-1 RNA and protein production in permissive cells.

In these experiments, viral RNA and protein synthesis in MNV-1.CW1-infected RAW 264.7 cells were analyzed to compare MNV-1 replication in cells with that of other caliciviruses. Northern blot analysis using a probe specific for the positive strand of the MNV-1 genome showed an increase in the accumulation of full-length (7.4 kb) and subgenomic-length (2.3 kb) MNV-1 genome over time (FIG. 18, Panel F). Radiolabeled MNV-1-infected RAW 264.7 cell lysates were analyzed by immunoprecipitation with serum from a MNV-1 infected mouse, and a 59-kDa protein consistent with the capsid protein was detected as early as 6 h.p.i. (FIG. 18, Panel G). Additional proteins accumulated over time that corresponded in size to expected calicivirus nonstructural proteins such as the 76-kDa proteinase-polymerase precursor and an approximately 40-kDa NTPase protein (Sosnovtsev et al., J Virol 76, 7060-7072, 2002). These data show that the viral RNA and proteins synthesized in infected cells are consistent with calicivirus replication (Green et al., In: Knipe D M, Howley P M, editors Fields Virology, Philadelphia: Lippincott Williams and Wilkins, pp 841-874, 2001).

Example 51

Figure 19:
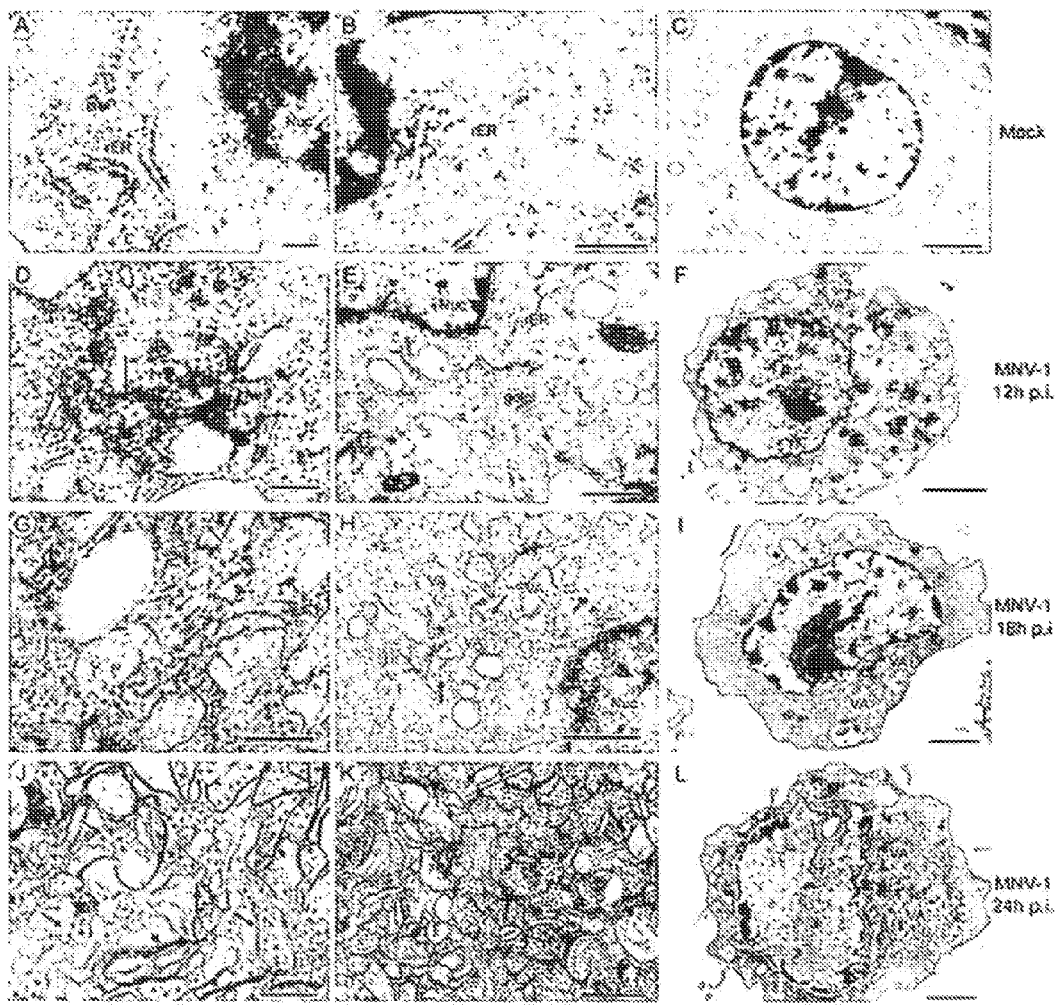
FIG. 19 illustrates ultrastructure of MNV-1.CW1-infected RAW 264.7 cells.

This example illustrates ultrastructural examination of MNV-1-infected RAW 264.7 cells Positive-strand RNA viruses (Dales et al., Virol 26: 379-389, 1965; Mackenzie et al., J Virol 73: 9555-9567, 1999; Pedersen et al., J Virol 73: 2016-2026, 1999), including caliciviruses (Love et al., Arch Virol 48: 213-228, 1975; Studdert and O'Shea, Arch Virol 48: 317-325, 1975; Green et al., J Virol 76: 8582-8595, 2002), are known to replicate in association with intracellular membranes. Therefore, we examined the ultrastructural morphology of MNV-1.CW1-infected RAW 264.7 cells (FIG. 19). Over time, virus-infected cells showed a striking change in overall morphology and intracellular organization (FIG. 19 Panels D-4L) compared to mock-infected cells (FIG. 19, Panels A-C). Structures resembling virus particles were observed within or next to single- or double-membrane vesicles in the cytoplasm by 12 hours post infection (h.p.i.) (FIG. 19, Panel D). The vesiculated areas increased in size with time (FIG. 19, Panels G-I), and by 24 h.p.i., large numbers of these vesicles and viral particles occupied most of the cytoplasm, displacing the nucleus (FIG. 19, Panels J-L). In addition, a complete rearrangement of intracellular membranes with some confronting membranes occurred (FIG. 19, Panel J), leading to a rearrangement of the endoplasmic reticulum and loss of an intact Golgi apparatus (FIG. 19, Panel E; data not shown). Interestingly, these smooth-membrane vesicles were often surrounded by mitochondria. A small proportion of cells also showed crystalline arrays of cytoplasmic virus particles (data not shown).

FIG. 19 illustrates ultrastructural studies of MNV-1.CW1-infected RAW 264.7 cells.

As shown in FIG. 19, cells were infected with MNV-1.CW1 (P3) (MOI of 2.0) (Panels D-L) or mock-infected (Panels A-C) and processed for electron microscopy 12 hours post infection (h.p.i.) (FIG. 19, Panels D-F), 18 h.p.i. (FIG. 21 Panels G-I, or 24 h.p.i. (FIG. 21A-C; J-L). MNV-1 particles are indicated by arrows and confronting membranes by arrowheads. VA, vesiculated areas; Nuc, nucleus; rER, rough endoplasmic reticulum. Scale bars, 200 nm for (A), (D), (G), and (J); 500 nm for (B), (E), (H), and (K); 2 µm for (C), (F), (I), and (L).

These observations indicate that like other positive-strand RNA viruses, norovirus RNA replication likely occurs in association with intracellular membranes.

Example 52

This example illustrates characterization of the plaque-purified strain MNV-1.CW1 in vitro In these experiments, to determine whether the plaque purification and sequential amplification of MNV-1 in RAW 264.7 cells had altered its growth characteristics, different cell types were infected with passage P3 of MNV-1.CW1. In general, the growth of MNV-1.CW1 (P3) in wild type (wt) or STAT1−/− macrophages and MEFs (FIG. 20, Panel A) as well as RAW 264.7 cells (data not shown) was similar to that observed for the original parental MNV-1 virus stock (compare FIG. 17 Panel B and FIG. 20 Panel A). Virus titers were reproducibly higher in STAT1−/− cells compared to wt cells, and MNV-1.CW1 (P3) growth was consistently observed in wt BMMΦ.

Figure 20:
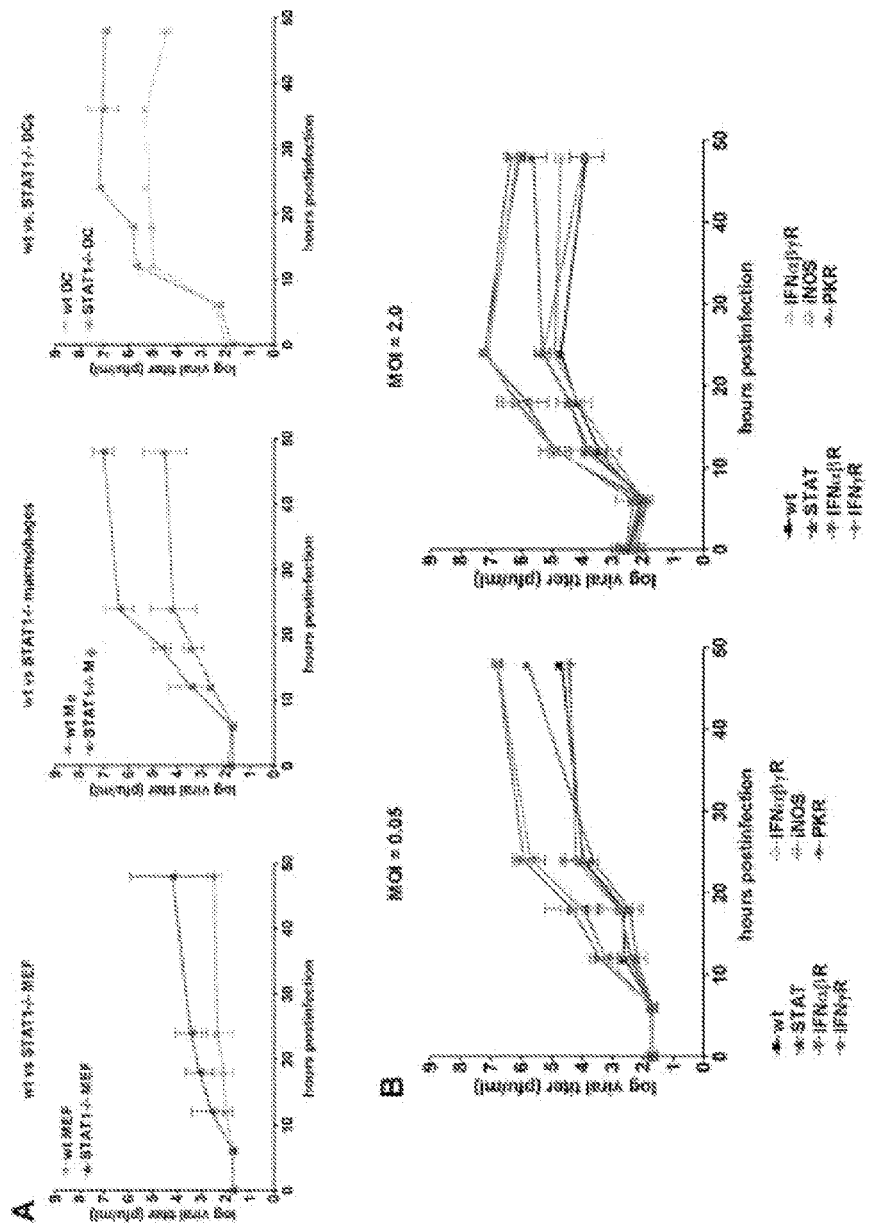
FIG. 20 illustrates a role for STAT-1 in limiting MNV-1 growth in vitro.

FIG. 20 illustrates a critical role for STAT-1 in limiting MNV-1 growth in vitro.

Panel 20, Panel A illustrates that MNV-1.CW1 has no defect in viral growth in vitro. Growth curves (MOI of 0.05) were performed two or three times with MNV-1.CW1 (P3) on indicated cells to calculate standard deviations.

Panel 20, Panel B illustrates that MNV-1 growth in macrophages is controlled by STAT-1 and Type I IFNs. BMMΦ of the indicated genotype were infected with MNV-1.CW1 (P3) at the indicated MOI. The experiment was performed twice to calculate standard deviations. The p-values for PKR versus wt infection at MOI 0.05 and 2.0, 0.8867 and 0.1616, respectively, are not significant. Statistical analysis was performed using the paired t-test (GraphPad Prism, version 3.03).

These data demonstrate that our plaque purification and serial passage in RAW 264.7 cells does not change the tropism of the virus for primary dendritic cells and macrophages and confirms the importance of STAT-1 in controlling MNV-1 growth at the cellular level.

Example 53

This example illustrates cellular factors controlling MNV-1 growth in vitro

Previous studies demonstrated that a lack of STAT-1 or both IFNαβR and IFNγR increases susceptibility to MNV-1 infection. However, mice lacking individual IFNR, inducible nitric oxide (iNOS)−/−, or protein kinase R (PKR)−/− are not susceptible (Karst at al. 2003). Therefore, we determined whether molecules other than STAT-1 exhibited antiviral effects at the level of the infected cell. Primary BMMΦ from wt mice or mouse strains deficient in STAT-1, IFNαβR, IFNγR, IFNαβγR, iNOS, or PKR were directly compared for their ability to support virus replication at two different multiplicities of infection (MOIs) (FIG. 20, Panel B). Again, BMMΦ cells from both wt and STAT1−/− mice supported MNV-1 virus replication, with higher titers observed in cells deficient in STAT-1. Cells obtained from mice lacking both Type 1 and II IFNR (IFNαβγR−/−) or Type I IFNR alone (IFNαβR−/−) supported replication of virus as efficiently as STAT 1−/− cells. In addition, wt BMMΦ and wt BMDCs secrete IFNα after MNV-1-infection, as determined by IFNα enzyme-linked immunosorbent assay (ELISA) (data not shown). This is consistent with a direct role for IFN signaling in MNV-1 growth but does not rule out the possibility that effects of STAT-1 and IFNαβR occur in vivo prior to explantation of the bone marrow. Absence of IFNγR, iNOS, or PKR did not have a statistically significant effect on MNV-1 growth in BMMΦ. Together, these data demonstrate that the antiviral molecules STAT-1 and IFNαβ are part of a cellular response that limits norovirus growth.

Example 54

Figure 21:
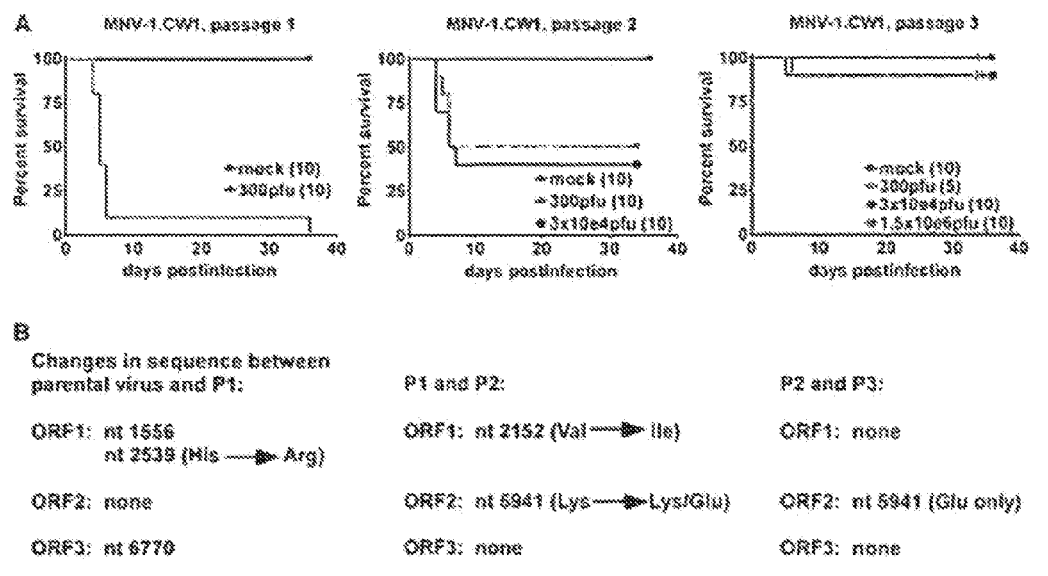

This example illustrates characterization of Plaque-Purified Strain MNV-1.CW1 In Vivo In these experiments, to address the effects of cell culture adaptation on virulence, STAT1−/− mice were infected orally with MNV-1.CW1 from three successive passages (P1, P2, and P3)(FIG. 21, Panel A). Oral administration of MNV- 1.CW1 (P1) resulted in lethal infection, similar to that previously reported for the parental MNV-1 brain tissue stock (Karst et al., Science 299: 1575-1578, 2003). These data fulfill a Koch's postulate with regard to MNV-1 infection and are consistent with the identification of MNV-1 as the infectious agent that was passaged in animals in our initial studies (Karst et al., Science 299: 1575-1578, 2003). In contrast, MNV-1.CW1 (P3) failed to cause a lethal infection in STAT1−/− mice after oral inoculation, even when administered a dose of 1.5×106 plaque-forming units (pfu), 5,000 times greater than the lethal dose for P1. In addition, immunohistochemical analysis of sectioned spleen and liver from STAT1−/− mice infected orally with 1.5×106 pfu of MNV-1.CW1 (P3) did not reveal any MNV-1-specific staining, unlike the parental virus (see FIG. 18, data not shown). This striking difference in virulence and decrease of viral antigen in infected mice, coupled with an intermediate lethality phenotype of the MNV-1.CW1 (P2) virus, show that serial passage of the virus in cell culture can attenuate MNV-1 virulence in vivo.

FIG. 21 illustrates that changes in virulence of plaque-purified MNV-1 over multiple passages are associated with limited amino acid changes.

Panel 21, Panel A illustrates that serial passage of MNV-1.CW1 in cell culture causes attenuation. In these experiments, STAT1−/− mice were infected orally with the indicated virus dose. The number of mice analyzed is indicated in parentheses.

Panel 21, Panel B presents a summary of sequence analysis of MNV-1 over several passages. The nucleotide and amino acid differences between the indicated viruses are shown (for details see Table 1).

Example 55

This example illustrates molecular analysis of serially passaged MNV-1.CW1

In these experiments, consensus sequence analysis was performed on the RNA genome of MNV-1 present in the original brain tissue stock (parental virus), and in viruses from each subsequent cell culture passage of MNV-1.CW1 (P1 through P3) to examine the molecular basis for the attenuation (FIG. 21 Panel B; Table 1). The analysis reveals that three nucleotide changes occurred between the parental virus and PI, with one of these resulting in an amino acid substitution (histidine to arginine) at residue 845, located within the predicted "3A-like" region of the nonstructural polyprotein. In the P2 virus, which retained virulence but at a reduced level compared to the parental and P1 viruses, a second nucleotide substitution within the predicted "3A-like" coding region was observed that caused an amino acid change (valine to isoleucine) at residue 716. The partial attenuation of virulence of the P2 virus in vivo is of interest since the homologous protein in poliovirus, the 3A protein, alters the amount of cytokines secreted from cells, with likely effects on viral pathogenesis (Dodd et al., J Virol 75: 8158-8165, 2001). Of note, a mixed population of A and G nucleotides was detected at position 5,941 of the P2 viral genome that could potentially yield two populations of virus with either amino acid lysine or glutamic acid at residue 296 of the capsid protein. In the P3 virus, which was avirulent in mice, the G nucleotide sequence at position 5,941 emerged as the predominant sequence. These experiments illustrate that nucleotide changes can account for the differences in virulence of serially-passaged MNV virus.

TABLE 1

| Open Reading Frame (ORF) | Genomic Position of Nucleotide | Position of Amino Acid | Parental MNV-1 | MNV-1.CW1 (P1) | MNV-1.CW1 (P2) | MNV-1.CW1 (P3) |
|---|---|---|---|---|---|---|
| ORF1 | 581 | 192 | CAA/CAT (Gln/His) | CAT | CAT | CAT |
|  | 986 | 327 | GTA/GTG (Val) | GTG | GTG | GTG |
|  | 1,283 | 426 | CTG/CTA (Leu) | CTG | GTG | CTG |
|  | 1,556 | 517 | CTA (Leu) | CTG | CTG | CTG |
|  | 2,151 | 716 | GTC (Val) | GTC | ATC (Val→Ile) | ATC |
|  | 2,539 | 845 | CAT (His) | CGT (His→Arg) | CGT | CGT |
|  | 2,816 | 937 | GAC/GAT (Asp) | GAT | GAT | GAT |
|  | 2,996 | 997 | GTT/GTC (Val) | GTC | GTC | GTC |
|  | 3,902 | 1,299 | AGT/AGC (Ser) | AGT | AGT | AGT |
|  | 4,322 | 1,439 | GGC/GGT (Gly) | GGC | GGC | GGC |
| ORF2 | 5,262 | 69 | ATT/ATC (Ile) | ATC | ATC | ATC |
|  | 5,446 | 137 | ACC/ACT (Thr) | ACT | ACT | ACT |
|  | 5,941 | 296 | AAG (Lys) | AAG | AAG/GAG (Lys→Lys/Lys→Glu) | GAG (Lys→Glu) |
| ORF3 | 6,770 | 30 | AAC (Asn) | AAT | AAT | AAT |

Nucleotides are numbered according to consensus sequence of the parental MNV-1 virus genome (in brain tissue stock) as follows: ORF1 (nt 6-5,069), ORF2 (nt 5,056-6,681), and ORF3 (nt 6,681-7,307), encoding a large polyprotein (viral nonstructural proteins), VP1 (major capsid structural protein), and VP2 (minor capsid structural protein), respectively. Amino acid residues are numbered according to location in the corresponding ORF. # The nucleotide position of interest is underlined and its location in the codon of the translated ORF is shown. Sequence heterogeneity at a particular residue was determined from the sequence chromatogram, and the data shown represent direct sequence analysis of PCR-amplified cDNA products. A change in deduced amino acid sequence from the previous passage is indicated in parentheses. DOI: 10.1371/journal.pbio.020432.t001

All references cited in this specification are hereby incorporated by reference in their entireties. Any discussion of references cited herein is intended merely to summarize the assertions made by their authors and no admission is made that any reference or portion thereof constitutes relevant prior art. Applicants reserve the right to challenge the accuracy and pertinency of the cited references.

The norovirus described above assigned ATCC Accession Number PTO-5935 is on deposit under the terms of the Budapest Treaty with the American Type Culture Collection, 10801 University Boulevard, Manassas, Va. 20110-2209. The strain was deposited on Apr. 27, 2004 and the requisite fees were paid. The accession number indicated is assigned after successful viability testing. Access to the culture will be available during pendency of the patent application to one determined by the Commissioner to be entitled thereto under 37 C.F.R. §1.14 and 35 U.S.C. §122. All restriction on availability of said culture to the public will be irrevocably removed upon the granting of a patent based upon the application. Moreover, the designated deposit will be maintained for a period of thirty (30) years from the date of deposit, or for five (5) years after the last request for the deposit, or for the enforceable life of the U.S. patent, whichever is longer. Should a culture become nonviable or be inadvertently destroyed, or, in the case of plasmid-containing strains, lose its plasmid, it will be replaced with a viable culture. The deposited material mentioned herein is intended for convenience only, and is not required to practice the present invention in view of the description herein, and in addition, this material is incorporated herein by reference.

The descriptions set forth herein are merely exemplary in nature and, thus, variations that do not depart from the gist of the invention are intended to be within the scope of the invention. Such variations are not to be regarded as a departure from the spirit and scope of the invention.

SEQUENCE LISTING

<160> NUMBER OF SEQ ID NOS: 40

<210> SEQ ID NO 1
<211> LENGTH: 7382
<212> TYPE: RNA
<213> ORGANISM: Mouse norovirus

<400> SEQUENCE: 1

```
gugaauucua gaaggcaacg ccaucuucug cgcccucugu gcgcaacaca gagaaacgca      60
aaaacaagaa ggcuucgycu aaagcuagug ucuccuuugg agcaccuagc ccccucucuu     120
cggagagcga agacgaaruu aauuacauga ccccuccuga gcaggaagcu cagcccggcg     180
cccuugcggc ccuucaugcg gaagggccgc uugccgggcu ccccgugacg cguagugaug     240
cacgcgugcu gaucuucaau gaguggagg agaggaagaa gucugauccg uggcuacggc     300
uggacauguc ugauaaggcu aucuuccgcc guuaccccca ucugcggccu aaggaggaua     360
ggccugacgc gcccucccau gcggaggacg cuauggaugc caaggagccu gugaucggcu     420
cuaucuugga gcaggaugau cacaaguuuu accauuacuc ugucuacauc ggggcggcc     480 uugugauggg ggucaacaac cccagugcug cggucugcca ggcaacgauu gauguggaga     540
agcuacaccu cugguggcgg ccugucuggg agccccgcca wccccuugac ucggcugagu     600
ugaggaagug cgugggcaug acugucccu acguggccac caccgucaac uguuaucagg     660
ucugcugcug gauuguugc aucaaggaca ccuggcugaa gagggcgaag aucucuagag     720
aucugcccuu cuacagcccc guccaggacu ggaacgucga ccccccaggag cccuucauuc     780 cauccaagcu caggaugguc ucggauggca uccuggugc cuugucggca gugauuggcc     840
ggccaauuaa gaaccuacug gccucaguua agccgcucaa cauucucaac aucgugcuga     900
gcugugauug gaccuuuucg ggcauuguca augcccugau cuugcuugcu gagcucuuug     960 acaucuuug gaccccccu gauguracca rcuggaugau cucuaucuuc ggggaauggc    1020
aggccgaagg gcccuucgac cyugcucuug acguggugcc caccccuguug ggcgggaucg    1080 ggauggcuuu uggccucrcc ucugagacca ucgggcgcaa gcucdcuucc accaacucgg    1140
cucucaaggc cgcccaagag auggagcaagu ucgccauaga ggucuucaag caaauuuaugg    1200 ccuggaucug gcccucugag gacccagugc cagcccucuu auccaacaug gagcaggcca    1260
ucauuaagaa ugaguguucaa cudgagaacc aacucacggc cauguugcgg gaucgcaacg    1320 cagggggcuga auuccuvagg ucccuugaug aggaggagca ggaagccgc aagaucgcag    1380 cuaagugcgg caacucggcc accacuggaa ccaccaacgc ucugcuggcc aggaucagca    1440 uggccccgcgc ggccuuugag aaagcucgcg cugaacagac cucccgaguc cgcccugugg    1500
ugducauggu cucaggcagg cccggggaucg ggaaaaccug cuuugccaa aaccuagcca    1560
```

```
agaggauugc ugcgucccug ggugaugaga ccucuguugg caucauacca cgcgcugaug    1620
ucgaccacug ggaugcuuac aagggagcca gagugguucu cugggaugau ucggcaugg     1680 acaacguggu gaaggaugca cugaggcuuc agaugcuugc cgacacgugc ccagugacac    1740 ucaauguga caggauugag aacaagggaa agaugyuuga cucucagguc auuaucauca    1800
ccacaaauca acaaaccccc gygcccugg acuaugucaa ccuggaggcg ucucgccgcc    1860
gcauagauuu ccugguuuau gmugagagcc cuguuguuga ugaugcucgg gccagagccc   1920
cuggcgaugu gaaugcagug aaagcugcca ugaggcccga uuacagccac aucaauuuca   1980
ucuuggcacc gcagggcggc uuugaccguc gggaaacacc cccuacggua agggcgucac   2040
caagaucauu ggcgccacug cucuuugcgc gagagcgguu gcucuugucc augagcgcca   2100
ugaugauuuc ggccuccaga acaaggucya ugacuuugau gcgcgcaarg ucaccgccuu   2160
caaagccaug gcggcugacg ccggcauucc augguacaaa auggcagcua uggggugcaa   2220
agcaaugggg gugcaccugu guagaggagg ccaugcauuu acuuaaggau auqaqquqq    2280 cucccuguca ggugaucuac aauggugcca ccauaauugu gagcugcauc aagggugccc   2340
caaugguuga aaaggucaag gagccugaau ugcccaaaac acuugucaac ugugucagaa   2400
ggauaaagga ggcccgccuc cgcugcuacu guaggauggc ugcugacguc aucacgucca   2460
uucugcaggc ggccggcacg gccuucucua uuuaccacca gauugagaag ggucuagac    2520 cauccuuuua uugggaucau ggauacaccu accgugacgg accuggaucc uuugacaucu   2580
uugaggauga cgaugauggg ugguaccacu cugagggaaa gaagggcaag aacaagaagg   2640 gccggggcg acccggaguc uucagaaccc gugggcucac ggaugaggag uacgaugaau    2700
ucaagaagcg ccgcgagucu aggggcggca aguacccau ugaugauuac cucgcugrcc    2760
gcgagcgaga agaagaacuc cuggagcggg acgaggagga ggcuaucuuc ggggayggcu   2820 ucgguggaa ggccaccgc cguuccgca aggcagagag agccaaacug ggccugguuu      2880
cugguggcga cauccgcgcc cgcaagccga ucgacuggaa uguggguuggc ccucccuggg  2940 cugacgauga ccgccaggue gcuacggcga gaagaucaac uuugaggccc cagyuyccau   3000 cuggcccgu guugugcagu ucggcacggg gugggcuuu uggggugagc ggccacgucu    3060
ucaucaccgc caagcaugug gcgcccccca agggcacgga gaucuuuggg cgcaagccg    3120 gggacuucac ugucrcuucc agcggggacu ucuugaagua cuacuucacc agcgccguca   3180
ggccugacru ucccgccaug guccuggaga augggugcca ggaggcguc gucgccucgg    3240 uccuugucaa gagagccucc ggcgagaugc uugcccuggc ugucaggaug gguucacagg   3300
ccgccaucaa gauugguagu gccguugugc augggcaaac uggcaugcuc cugacuggcu   3360
cuaaugccaa ggcccaggac cucgggacca ucccgggcga cuguggcugu cccuauguuu  3420
auaagaaggg uaacaccugg guugugauug gggugcacgu ggcggccacu aggucuggua   3480
acacagucau ugccgccacu cacgagaac ccacacuuga ggcucuggag uuccagggac    3540
cccccaugcu ucccogcccc ucaggcaccu augcaggccu ccccaucgcc gauuacgcg    3600 acgcucccc cuugagcacc aagaccaugu ucugccguac cucgccagag aagcuucccc    3660
cuggggcuug ggagccagcc uaucucggcu cuaaagauga gaggugggac gguccuuccc   3720
uucagcaggu caugcgagau cagcuuaagc ccuauucaga accacgcggu cugcuucccc   3780
cucaagaaau ccuugaugca gucugcgacg ccauugagaa ccgccuugag aacaccccuug  3840 aaccacagaa gcccggaca uuuaagaagg cuugugagag cuuggacaag aacaccagya   3900
gygggauacc cuaucacaag cagaagagca aggacuggac gggaagcgcu uuuauuggcg   3960
```

-continued

| | |
|---|---|
| rucuuggluga ccaggccacc cacgccaaca acauguauga gaugguaaa uccaugcgac | 4020 |
| ccauuuauac agcugcccuc aaggaugaac ugguuaagcc agacaagauc uacgggaaga | 4080 |
| uaaagaagag gcuucucugg ggcucugacc uugrcaccau gauucgcgcu gcccgugcyu | 4140 |
| uuggcccuuu cugugaugcu cugaaagaar ccugcauuuu caaccccauc agaguggca | 4200 |
| ugucgaugaa cgaagauggc cccuucaucu ucgcaagaca cgccaauuuc agguaccaca | 4260 |
| uggaugcuga cuauaccagg ugggacucca cccaacagag agccauccua aagcgcgcug | 4320 |
| gygacaucau ggygcgccuc uccccugagc cagacuuggc ucggguuguc auggaugauc | 4380 |
| uccuggcccc cucgcuguug gacgucggcg acuruaagau cguugucgag gaggggcucc | 4440 |
| cauccggcug cccuugcacc acacagcuga auaguuuggc ucacuggauu ugacccuuu | 4500 |
| gugcaauggu ugagguaacc cgaguugacc cugacauugu gaugcaagaa ucugaguuyu | 4560 |
| ccuucuaugg ugaugacgag guggguucga ccaaccucga guuggauaug guuaaguaca | 4620 |
| ccauggcuuu gaggcgguac ggucuccucc cgacucgcgc ggacaaggag gagggaccuc | 4680 |
| uggagcgucg ccagacgcug cagggcaucu ccuuccugcg ccgugcgaua guuggugacc | 4740 |
| aguuugggug guacggucgu cuugaucgug ccagcaucga ccgccagcuc cucuggacua | 4800 |
| aaggaccuaa ccaccagaac cccuuugaga cucccccugg acaugcucag agacccuccc | 4860 |
| aacuaauggc ccugcucggu gaggcugcca ugcaugguga aaaguauuac aggacugugg | 4920 |
| cuucccgugu cuccaaggag gccgcccaaa gugggauara aauggguaguc cccacgccac | 4980 |
| cgaucuguuu ugcgcugggu gcgcuuugga aaauggaugc ugagaccccg caggaacgcu | 5040 |
| cagcagucuu ugugaaugag gaugagugau ggcgcagcgc caaaagccaa uggcucugag | 5100 |
| gccagcggcc aggaucuugu uccugccgcc guugaacagg ccgucccccay ucaacccgug | 5160 |
| gcuggcgcgg cucuugccgc cccgccgcc gggcaaauua ccaaaauugr ccccuggauc | 5220 |
| uuccaaaauu uugccagug cccccuuggu gaguuuucca uuucgccucg aaacaccccca | 5280 |
| ggugaaauac uguuugauuu ggcccucggg ccagggcuua accccuaccu ugcccaccuc | 5340 |
| ucagccaugu acaccggcug gguugggaac ruggagguuc agcuggucu cgccggcaau | 5400 |
| gccuuuacug cuggcaaggu gguuguugcc cuuguaccac ccuauuuucc caaggggguca | 5460 |
| cucaccacug cccagaucac augcuuccca caugucaugu gugaugugcg cacccuggag | 5520 |
| cccauucaac ucccucuucu ugaugugcgu cgagucccuu ggcaugcuac ccaggaucaa | 5580 |
| gaggaaucua ugcgccuggu uugcaugcug uacgccac uccgcacaaa cagcccgggu | 5640 |
| gaugagucuu uuguggucuc uggccgccuu cuuucuaagc cggcggcuga uuucaauuuu | 5700 |
| gucuaccuaa cucccccau agagagaacc aucuaccgga uggucgacuu gcccgugaua | 5760 |
| cagccgcggc ugugcacgca cgcacguugg ccugcccgg ucuaugucu cuuggguggac | 5820 |
| ccaucccucc ccucaaauuc ccagguggcag aauggaaggg ugcacguuga uggggacccug | 5880 |
| cuuguacca ccccaaucuc cgguucaugg guguccugcu uugcgkcgga ggcugccuau | 5940 |
| aaguccaau cgggcaccgg ugagguggcg acauucaccc ugauugagca ggauggaucu | 6000 |
| gccuacgucc ccggugacag ggcagcacca cucggguuac cccgauuucu cugggcaacu | 6060 |
| ggagaucgag guccagaccg agaccaccaa gacuggagac aagcucaagg ucaccacuuu | 6120 |
| gagaugauuc uuggcccaac gaccaacgcg gaccaggccc cuaccaggg cagggguuc | 6180 |
| gccagcguca cugcugcggc cucucuuugac ugguggaug gcaggguucg ugcgguccca | 6240 |
| agauccaucu acgguuuuca ggacaccauc ccugaauaca acgauggcu acuguuccc | 6300 |

```
cuugccccc  caauugguc  cuuucuccc  ggcgaggucc  uccugagguu  ccggaccuac   6360
augcgucaga  ucgacaccgc  ugacgccgca  gcagaggcga  uagacugugc  acuccccag   6420 gaguuugucu  ccugguucgc  gucuaacgcg  uucaccgugc  aguccgaggc  ccugcuccuu  6480
agauacagga  acacccugac  ugggcaacug  cuguucgagu  gcaagcucua  caacgaaggu  6540
uacaucgccu  ugucuuauuc  cggcucagga  ccccucaccu  ucccgaccga  uggcaucuuu  6600
gaggucguca  guugggguucc  ucgccuuuac  caauuggccu  cugugggaag  uuggcaaca   6660 ggccgaaugc  ucaaacaaua  auggcuggug  cucuuuuugg  agcgauugga  gguggccuga   6720
ugggcauaau  uggcaauucc  aucucaaaug  uucaaaaccu  ucaggcaaac  aaacaauugg   6780
cagcucagca  auuugguuau  aauucuuccc  ugcuugcaac  gcaaauucaa  gcccagaagg   6840
aucucacucu  gauggggcag  caauucaacc  agcagcucca  aaccaacucu  uucaagcacg   6900
acuuggaaau  gcuuggcgcu  caggugcaag  cccaggcgca  ggcccaggag  aacgccauca   6960
auaucaaaac  ggcgcagcuc  caggccgcag  gcuuuucaaa  gacagaugcc  acacgccuug   7020
ccuuggggca  gcagcccacg  agggccgugg  auuggucugg  gacgcgguac  uacaccgcua   7080
accagccagu  cacgggcuuc  ucggguggcu  uuaccccaac  cuacacucca  gguaggcaag   7140 ugacauccccg  cccuguggac  acaucccccuc  uaccgaucuc  ggguggacgc  uugcccucc   7200 uucguggagg  uuccuggucc  ccgcgcgacc  auacgccggc  gacucaaggc  accuacacga   7260
acggacgguu  cgucucucuc  ccuaagaucg  ggaguagcag  ggcauagguu  ggaagagaaa   7320
ccuuuuguga  aaaugauuuc  ugcuuacugc  uuucuuuucu  uugugguagu  uagaugcauu   7380
uc                                                                    7382

<210> SEQ ID NO 2
<211> LENGTH: 9
<212> TYPE: DNA
<213> ORGANISM: Mouse norovirus

<400> SEQUENCE: 2 gtgaaatga                                                                9

<210> SEQ ID NO 3
<211> LENGTH: 11
<212> TYPE: DNA
<213> ORGANISM: Mouse norovirus

<400> SEQUENCE: 3
gtgaaatgag g                                                            11

<210> SEQ ID NO 4
<211> LENGTH: 9
<212> TYPE: DNA
<213> ORGANISM: Mouse norovirus

<400> SEQUENCE: 4 taccgatct                                                                9

<210> SEQ ID NO 5
<211> LENGTH: 14
<212> TYPE: DNA
<213> ORGANISM: Mouse norovirus

<400> SEQUENCE: 5
ctaccgatct cggg                                                         14
```

<210> SEQ ID NO 6
<211> LENGTH: 18
<212> TYPE: DNA
<213> ORGANISM: Mouse norovirus

<400> SEQUENCE: 6
gtgaaatgag gtaccgat                                                    18

<210> SEQ ID NO 7
<211> LENGTH: 9
<212> TYPE: DNA
<213> ORGANISM: Mouse norovrius

<400> SEQUENCE: 7 taccgatcg                                                               9

<210> SEQ ID NO 8
<211> LENGTH: 47
<212> TYPE: DNA
<213> ORGANISM: Mouse norovirus

<400> SEQUENCE: 8
atcaatatca aaacggcgca gctccaggcc gcaggctttt caaagac                    47

<210> SEQ ID NO 9
<211> LENGTH: 10
<212> TYPE: DNA
<213> ORGANISM: Mouse norovirus

<400> SEQUENCE: 9
gtgaaatgag                                                             10

<210> SEQ ID NO 10
<211> LENGTH: 213
<212> TYPE: DNA
<213> ORGANISM: Mouse norovirus

<400> SEQUENCE: 10
cagctccagg ccgcaggctt ttcaaagacg gatgccgcac gccttgcctt ggggcagcag      60
cccacgaggg ccgtggattg gtctgggacg cggtactaca ccgctaacca gccagtcacg     120
ggcttctcgg gtggctttac cccaacctac actccaggta ggcaagtgac atcccgccct     180
gtggacacat cccctctacc gatctgtgaa atg                                  213

<210> SEQ ID NO 11
<211> LENGTH: 203
<212> TYPE: DNA
<213> ORGANISM: Mouse norovirus

<400> SEQUENCE: 11
ccgcaggctt ttcaaagacg gatgccgcac gccttgcctt ggggcagcag cccacgaggg      60
ccgtggattg gtctgggacg cggtactaca ccgctaacca gccagtcacg ggcttctcgg     120
gtggctttac cccaacctac actccaggta ggcaagtgac atcccgccct gtggacacat     180
cccctctacc gatctgtgaa atg                                             203

<210> SEQ ID NO 12
<211> LENGTH: 193
<212> TYPE: DNA
<213> ORGANISM: Mouse norovirus

<400> SEQUENCE: 12

```
ttcaaagacg gatgccgcac gccttgcctt ggggcagcag cccacgaggg ccgtggattg    60
gtctgggacg cggtactaca ccgctaacca gccagtcacg ggcttctcgg gtggctttac   120
cccaacctac actccaggta ggcaagtgac atcccgccct gtggacacat cccctctacc   180
gatctgtgaa atg                                                      193

<210> SEQ ID NO 13
<211> LENGTH: 183
<212> TYPE: DNA
<213> ORGANISM: Mouse norovirus

<400> SEQUENCE: 13
gatgccgcac gccttgcctt ggggcagcag cccacgaggg ccgtggattg gtctgggacg    60
cggtactaca ccgctaacca gccagtcacg ggcttctcgg gtggctttac cccaacctac   120
actccaggta ggcaagtgac atcccgccct gtggacacat cccctctacc gatctgtgaa   180
atg                                                                 183

<210> SEQ ID NO 14
<211> LENGTH: 173
<212> TYPE: DNA
<213> ORGANISM: Mouse norovirus

<400> SEQUENCE: 14
gccttgcctt ggggcagcag cccacgaggg ccgtggattg gtctgggacg cggtactaca    60
ccgctaacca gccagtcacg ggcttctcgg gtggctttac cccaacctac actccaggta   120
ggcaagtgac atcccgccct gtggacacat cccctctacc gatctgtgaa atg          173

<210> SEQ ID NO 15
<211> LENGTH: 163
<212> TYPE: DNA
<213> ORGANISM: Mouse norovirus

<400> SEQUENCE: 15
ggggcagcag cccacgaggg ccgtggattg gtctgggacg cggtactaca ccgctaacca    60
gccagtcacg ggcttctcgg gtggctttac cccaacctac actccaggta ggcaagtgac   120
atcccgccct gtggacacat cccctctacc gatctgtgaa atg                     163

<210> SEQ ID NO 16
<211> LENGTH: 153
<212> TYPE: DNA
<213> ORGANISM: Mouse norovirus

<400> SEQUENCE: 16
cccacgaggg ccgtggattg gtctgggacg cggtactaca ccgctaacca gccagtcacg    60
ggcttctcgg gtggctttac cccaacctac actccaggta ggcaagtgac atcccgccct   120
gtggacacat cccctctacc gatctgtgaa atg                                153

<210> SEQ ID NO 17
<211> LENGTH: 143
<212> TYPE: DNA
<213> ORGANISM: Mouse norovirus

<400> SEQUENCE: 17
ccgtggattg gtctgggacg cggtactaca ccgctaacca gccagtcacg ggcttctcgg    60
gtggctttac cccaacctac actccaggta ggcaagtgac atcccgccct gtggacacat   120
cccctctacc gatctgtgaa atg                                           143
```

<210> SEQ ID NO 18
<211> LENGTH: 133
<212> TYPE: DNA
<213> ORGANISM: Mouse norovirus

<400> SEQUENCE: 18
gtctgggacg cggtactaca ccgctaacca gccagtcacg ggcttctcgg gtggctttac      60
cccaacctac actccaggta ggcaagtgac atcccgccct gtggacacat cccctctacc    120
gatctgtgaa atg                                                       133

<210> SEQ ID NO 19
<211> LENGTH: 123
<212> TYPE: DNA
<213> ORGANISM: Mouse norovirus

<400> SEQUENCE: 19
cggtactaca ccgctaacca gccagtcacg ggcttctcgg gtggctttac cccaacctac      60
actccaggta ggcaagtgac atcccgccct gtggacacat cccctctacc gatctgtgaa    120
atg                                                                  123

<210> SEQ ID NO 20
<211> LENGTH: 113
<212> TYPE: DNA
<213> ORGANISM: Mouse norovirus

<400> SEQUENCE: 20
ccgctaacca gccagtcacg ggcttctcgg gtggctttac cccaacctac actccaggta      60
ggcaagtgac atcccgccct gtggacacat cccctctacc gatctgtgaa atg           113

<210> SEQ ID NO 21
<211> LENGTH: 103
<212> TYPE: DNA
<213> ORGANISM: Mouse norovirus

<400> SEQUENCE: 21
gccagtcacg ggcttctcgg gtggctttac cccaacctac actccaggta ggcaagtgac      60
atcccgccct gtggacacat cccctctacc gatctgtgaa atg                      103

<210> SEQ ID NO 22
<211> LENGTH: 93
<212> TYPE: DNA
<213> ORGANISM: Mouse norovirus

<400> SEQUENCE: 22
ggcttctcgg gtggctttac cccaacctac actccaggta ggcaagtgac atcccgccct      60
gtggacacat cccctctacc gatctgtgaa atg                                  93

<210> SEQ ID NO 23
<211> LENGTH: 83
<212> TYPE: DNA
<213> ORGANISM: Mouse norovirus

<400> SEQUENCE: 23
gtggctttac cccaacctac actccaggta ggcaagtgac atcccgccct gtggacacat      60
cccctctacc gatctgtgaa atg                                             83

<210> SEQ ID NO 24

-continued

```
<211> LENGTH: 73
<212> TYPE: DNA
<213> ORGANISM: Mouse norovirus

<400> SEQUENCE: 24
cccaacctac actccaggta ggcaagtgac atcccgccct gtggacacat ccctctacc     60 gatctgtgaa atg                                                       73

<210> SEQ ID NO 25
<211> LENGTH: 63
<212> TYPE: DNA
<213> ORGANISM: Mouse norovirus

<400> SEQUENCE: 25
actccaggta ggcaagtgac atcccgccct gtggacacat ccctctacc gatctgtgaa     60 atg                                                                  63

<210> SEQ ID NO 26
<211> LENGTH: 53
<212> TYPE: DNA
<213> ORGANISM: Mouse norovirus

<400> SEQUENCE: 26
ggcaagtgac atcccgccct gtggacacat ccctctacc gatctgtgaa atg            53

<210> SEQ ID NO 27
<211> LENGTH: 33
<212> TYPE: DNA
<213> ORGANISM: Mouse norovirus

<400> SEQUENCE: 27
gtggacacat ccctctacc gatctgtgaa atg                                  33

<210> SEQ ID NO 28
<211> LENGTH: 93
<212> TYPE: DNA
<213> ORGANISM: Mouse norovirus

<400> SEQUENCE: 28
tagtccccac gccaccgatc tgttttgcgc tgggtgcgct ttggaaaatg gatgctgaga    60
ccccgcagga acgctcagca gtctttgtga atg                                 93

<210> SEQ ID NO 29
<211> LENGTH: 83
<212> TYPE: DNA
<213> ORGANISM: Mouse norovirus

<400> SEQUENCE: 29
gccaccgatc tgttttgcgc tgggtgcgct ttggaaaatg gatgctgaga ccccgcagga    60
acgctcagca gtctttgtga atg                                            83

<210> SEQ ID NO 30
<211> LENGTH: 73
<212> TYPE: DNA
<213> ORGANISM: Mouse norovirus

<400> SEQUENCE: 30
tgttttgcgc tgggtgcgct ttggaaaatg gatgctgaga ccccgcagga acgctcagca    60
gtctttgtga atg                                                       73
```

```
<210> SEQ ID NO 31
<211> LENGTH: 63
<212> TYPE: DNA
<213> ORGANISM: Mouse norovirus

<400> SEQUENCE: 31
tgggtgcgct tggaaaatg gatgctgaga ccccgcagga acgctcagca gtctttgtga    60
atg                                                                 63

<210> SEQ ID NO 32
<211> LENGTH: 53
<212> TYPE: DNA
<213> ORGANISM: Mouse norovirus

<400> SEQUENCE: 32
ttggaaaatg gatgctgaga ccccgcagga acgctcagca gtctttgtga atg          53

<210> SEQ ID NO 33
<211> LENGTH: 43
<212> TYPE: DNA
<213> ORGANISM: Mouse norovirus

<400> SEQUENCE: 33
gatgctgaga ccccgcagga acgctcagca gtctttgtga atg                     43

<210> SEQ ID NO 34
<211> LENGTH: 20
<212> TYPE: DNA
<213> ORGANISM: Mouse norovirus

<400> SEQUENCE: 34
ctaccgatct gtgaaatgag                                               20

<210> SEQ ID NO 35
<211> LENGTH: 11
<212> TYPE: DNA
<213> ORGANISM: Mouse norovirus

<400> SEQUENCE: 35
atgaagatgg c                                                        11

<210> SEQ ID NO 36
<211> LENGTH: 9
<212> TYPE: DNA
<213> ORGANISM: Mouse norovirus

<400> SEQUENCE: 36 gtgaaatga                                                            9

<210> SEQ ID NO 37
<211> LENGTH: 11
<212> TYPE: DNA
<213> ORGANISM: Mouse norovirus

<400> SEQUENCE: 37
gtgaaatgag g                                                        11

<210> SEQ ID NO 38
<211> LENGTH: 9
<212> TYPE: DNA
<213> ORGANISM: Mouse norovirus

<400> SEQUENCE: 38
```

-continued

```
taccgatct                                                          9

<210> SEQ ID NO 39
<211> LENGTH: 14
<212> TYPE: DNA
<213> ORGANISM: Mouse norovirus

<400> SEQUENCE: 39
ctaccgatct cggg                                                   14

<210> SEQ ID NO 40
<211> LENGTH: 18
<212> TYPE: DNA
<213> ORGANISM: Mouse norovirus

<400> SEQUENCE: 40
gtgaaatgag gtaccgat                                               18
```

What is claimed is:

1. A method of detecting a norovirus in a biological sample, the method comprising contacting a cell culture comprising norovirus-permissive cells with the sample, and detecting norovirus viral replication in the cell culture, wherein the norovirus-permissive cells are selected from the group consisting of macrophage-lineage cells and dendritic cell-lineage cells.

2. A method according to claim 1, wherein the biological sample is a diagnostic sample from a mammal suspected of infection with the norovirus.

3. A method according to claim 2, wherein the mammal is a human.

4. A method according to claim 2, wherein the mammal is a rodent.

5. A method according to claim 2, wherein the diagnostic sample is selected from the group consisting of a stool sample, a vomitus sample, a tissue sample and a blood sample.

6. A method according to claim 1, wherein the macrophage-lineage cells are macrophages deficient in a cellular anti-viral pathway selected from the group consisting of a STAT-1-dependent anti-viral pathway, an interferon receptor-dependent anti-viral pathway, a double-stranded RNA-dependent serine/threonine protein kinase-dependent antiviral pathway, and combinations thereof.

7. A method according to claim 6, wherein the macrophage-lineage cells are transformed macrophages selected from the group consisting of RAW 264.7 cells, J774A.1 cells and WBC264-9C cells.

8. A method according to claim 1, wherein the norovirus is selected from the group consisting of a murine norovirus and a human norovirus.

9. A method according to claim 1, wherein detecting norovirus viral replication comprises performing a virus detection assay selected from the group consisting of a cytopathic assay, an antibody assay, a nucleic acid detection assay and a protein detection assay.

10. A method according to claim 9, wherein the cytopathic assay is selected from the group consisting of a dye exclusion assay, an enzyme release assay and an apoptosis assay.

11. A method according to claim 9, wherein the antibody assay is selected from the group consisting of a Western blot assay, an ELISA assay, an immunofluorescence assay, an immunoprecipitation assay and a radioimmunoassay.

12. A method according to claim 9, wherein the nucleic acid detection assay is selected from the group consisting of a polymerase chain reaction assay and a hybridization assay.

* * * * *